United States Patent
Sokolovskii et al.

(10) Patent No.: US 10,851,074 B2
(45) Date of Patent: *Dec. 1, 2020

(54) PROCESSES FOR THE PREPARATION OF 2,5-FURANDICARBOXYLIC ACID AND INTERMEDIATES AND DERIVATIVES THEREOF

(71) Applicant: Stora Enso Oyj, Helsinki (FI)

(72) Inventors: Valery Sokolovskii, Santa Clara, CA (US); Vincent J. Murphy, San Jose, CA (US); Thomas R. Boussie, Menlo Park, CA (US); Gary M. Diamond, Menlo Park, CA (US); Eric L. Dias, Belmont, CA (US); Guang Zhu, Union City, CA (US); James M. Longmire, Sunnyvale, CA (US); Stanley Herrmann, Oakland, CA (US); Staffan Torssell, Bromma (SE); Mayya Lavrenko, Campbell, CA (US)

(73) Assignee: Stora Enso Oyj, Helsinki (FI)

( * ) Notice: Subject to any disclaimer, the term of this patent is extended or adjusted under 35 U.S.C. 154(b) by 0 days.

This patent is subject to a terminal disclaimer.

(21) Appl. No.: 16/841,478

(22) Filed: Apr. 6, 2020

(65) Prior Publication Data

US 2020/0231558 A1     Jul. 23, 2020

Related U.S. Application Data

(63) Continuation of application No. 16/552,096, filed on Aug. 27, 2019, which is a continuation of application
(Continued)

(51) Int. Cl.
*C07D 307/68* (2006.01)
*B01J 8/02* (2006.01)

(52) U.S. Cl.
CPC .............. *C07D 307/68* (2013.01); *B01J 8/02* (2013.01); *B01J 2208/00893* (2013.01); *Y02P 20/582* (2015.11)

(58) Field of Classification Search
CPC . C07D 307/68; B01J 8/02; B01J 2208/00893; Y02P 20/582
(Continued)

(56) References Cited

U.S. PATENT DOCUMENTS 2,673,860 A     3/1954   Kuhn et al.
2,750,394 A     6/1956   Peniston
(Continued)

FOREIGN PATENT DOCUMENTS

AU    2011205116 A1    8/2011
BR    PI1106661        8/2013
(Continued)

OTHER PUBLICATIONS

Abbadi et al., 1995, Effect of pH in the Pt-catalyzed oxidation of D-glucose to D-gluconic acid, J Mol Catalysis A: Chem 97:111-118.
(Continued)

*Primary Examiner* — Taylor V Oh
(74) *Attorney, Agent, or Firm* — Knobbe, Martens, Olson & Bear, LLP

(57) ABSTRACT

The present disclosure provides processes for the production of 2-5-furandicarboxylic acid (FDCA) and intermediates thereof by the chemocatalytic conversion of a furanic oxidation substrate. The present disclosure further provides processes for preparing derivatives of FDCA and FDCA-based polymers. In addition, the present disclosure provides crystalline preparations of FDCA, as well as processes for making the same.

37 Claims, 16 Drawing Sheets

Related U.S. Application Data

No. 16/264,188, filed on Jan. 31, 2019, now Pat. No. 10,442,780, which is a continuation of application No. 15/404,996, filed on Jan. 12, 2017, now Pat. No. 10,208,006.

(60) Provisional application No. 62/278,332, filed on Jan. 13, 2016.

(58) Field of Classification Search
USPC .................................................... 549/485
See application file for complete search history.

(56) References Cited

U.S. PATENT DOCUMENTS

| | | |
|---|---|---|
| 2,754,330 A | 7/1956 | Schreyer |
| 2,829,823 A | 4/1958 | Fedder |
| 2,917,529 A | 12/1959 | Drysdale |
| 2,929,823 A | 3/1960 | Garber et al. |
| 3,118,912 A | 1/1964 | Smith |
| 3,184,479 A | 5/1965 | Matter et al. |
| 3,290,263 A | 12/1966 | Smythe et al. |
| 3,326,944 A | 6/1967 | Lew |
| 3,329,626 A | 7/1967 | Teter et al. |
| 3,483,228 A | 12/1969 | Garber et al. |
| 4,005,178 A | 1/1977 | Bennett et al. |
| 4,339,387 A | 7/1982 | Fleche et al. |
| 4,400,468 A | 8/1983 | Faber |
| 4,438,082 A | 3/1984 | Dettling et al. |
| 4,533,743 A | 8/1985 | Medeiros et al. |
| 4,590,283 A | 5/1986 | Gaset et al. |
| 4,740,605 A | 4/1988 | Rapp et al. |
| 4,912,237 A | 3/1990 | Zeitsch et al. |
| 4,971,657 A | 11/1990 | Avignon et al. |
| 4,977,283 A | 12/1990 | Leupold et al. |
| 5,296,639 A | 3/1994 | Klug et al. |
| 5,312,967 A | 5/1994 | Kiely et al. |
| 5,472,648 A | 12/1995 | Alisch et al. |
| 5,474,965 A | 12/1995 | Nakatsuji |
| 5,639,929 A | 6/1997 | Bharadwaj et al. |
| 6,337,302 B1 | 1/2002 | Teng et al. |
| 6,500,969 B1 | 12/2002 | Zhou et al. |
| 6,518,440 B2 | 2/2003 | Lightner et al. |
| 6,534,680 B1 | 3/2003 | Rauls et al. |
| 6,599,723 B1 | 7/2003 | Hembre et al. |
| 6,743,928 B1 | 6/2004 | Hanna |
| 6,861,387 B2 | 3/2005 | Ruth et al. |
| 7,109,145 B2 | 9/2006 | Ruth et al. |
| 7,208,439 B2 | 4/2007 | Zhong et al. |
| 7,317,116 B2 | 1/2008 | Sanborn |
| 7,385,081 B1 | 6/2008 | Gong |
| 7,411,078 B2 | 8/2008 | Miura et al. |
| 7,566,681 B2 | 7/2009 | Bock et al. |
| 7,572,925 B2 | 8/2009 | Dumesic et al. |
| 7,579,490 B2 | 8/2009 | Sanborn et al. |
| 7,700,788 B2 | 4/2010 | Lilga et al. |
| 7,939,681 B2 | 5/2011 | Zhao et al. |
| 8,038,763 B2 | 10/2011 | Eichhorn et al. |
| 8,058,458 B2 | 11/2011 | Sanborn |
| 8,071,504 B2 | 12/2011 | Ragle et al. |
| 8,133,289 B2 | 3/2012 | Gruter et al. |
| 8,183,020 B2 | 5/2012 | Hanke |
| 8,193,381 B2 | 6/2012 | Lilga et al. |
| 8,193,382 B2 | 6/2012 | Lilga et al. |
| 8,231,693 B2 | 7/2012 | Gruter |
| 8,236,261 B2 | 8/2012 | Ragle et al. |
| 8,242,292 B2 | 8/2012 | Yutaka et al. |
| 8,242,293 B2 | 8/2012 | Gruter et al. |
| 8,273,504 B2 | 9/2012 | Goia et al. |
| 8,277,521 B2 | 10/2012 | Gruier |
| 8,314,260 B2 | 11/2012 | Gruter et al. |
| 8,314,267 B2 | 11/2012 | Brandvold |
| 8,324,409 B2 | 12/2012 | Rauchfuss et al. |
| 8,338,626 B2 | 12/2012 | Gruter et al. |
| 8,455,668 B2 | 6/2013 | Fu et al. |
| 8,501,989 B2 | 8/2013 | Boussie et al. |
| 8,519,167 B2 | 8/2013 | Muñoz de Diego et al. |
| 8,524,923 B2 | 9/2013 | Grushin et al. |
| 8,546,288 B2 | 10/2013 | Pulskamp et al. |
| 8,558,018 B2 | 10/2013 | Sanborn |
| 8,568,680 B2 | 10/2013 | Hui et al. |
| 8,604,225 B2 | 12/2013 | Pedersen et al. |
| 8,658,810 B2 | 2/2014 | Partin et al. |
| 8,669,383 B2 | 3/2014 | Howard et al. |
| 8,669,397 B2 | 3/2014 | Boussie et al. |
| 8,709,286 B2 | 4/2014 | Bloom et al. |
| 8,729,256 B2 | 5/2014 | Moliner-marin et al. |
| 8,748,479 B2 | 6/2014 | Shaikh et al. |
| 8,754,000 B2 | 6/2014 | Chan et al. |
| 8,772,513 B2 | 7/2014 | Janka et al. |
| 8,772,515 B2 | 7/2014 | Dumesic et al. |
| 8,785,667 B2 | 7/2014 | Grushin et al. |
| 8,785,668 B2 | 7/2014 | Du et al. |
| 8,791,277 B2 | 7/2014 | Janka et al. |
| 8,791,278 B2 | 7/2014 | Shaikh et al. |
| 8,796,477 B2 | 8/2014 | Janka et al. |
| 8,809,556 B2 | 8/2014 | Janka et al. |
| 8,846,960 B2 | 9/2014 | Janka et al. |
| 8,846,984 B2 | 9/2014 | Allgeier et al. |
| 8,846,985 B2 | 9/2014 | Allgeier et al. |
| 8,859,788 B2 | 10/2014 | Partin et al. |
| 8,859,826 B2 | 10/2014 | Allgeier et al. |
| 8,865,921 B2 | 10/2014 | Muñoz de Diego et al. |
| 8,877,950 B2 | 11/2014 | Gruter et al. |
| 8,901,326 B2 | 12/2014 | Howard et al. |
| 8,912,349 B2 | 12/2014 | Shaikh et al. |
| 8,916,719 B2 | 12/2014 | Shaikh et al. |
| 8,916,720 B2 | 12/2014 | Shaikh et al. |
| 8,927,768 B2 | 1/2015 | Boussie et al. |
| 8,969,404 B2 | 3/2015 | Janka et al. |
| 9,006,470 B2 | 4/2015 | Janka et al. |
| 9,018,423 B2 | 4/2015 | Allgeier et al. |
| 9,023,751 B2 | 5/2015 | Mizutani |
| 9,028,580 B1 | 5/2015 | Andrews |
| 9,029,579 B2 | 5/2015 | Janka et al. |
| 9,029,580 B2 | 5/2015 | Janka et al. |
| 9,029,581 B2 | 5/2015 | Partin et al. |
| 9,032,355 B2 | 5/2015 | Bantas et al. |
| 9,035,094 B2 | 5/2015 | Dias et al. |
| 9,035,109 B2 | 5/2015 | Dias et al. |
| 9,045,787 B2 | 6/2015 | Ruijssenaars et al. |
| 9,090,550 B2 | 7/2015 | Howard et al. |
| 9,090,581 B2 | 7/2015 | De Sousa Dias et al. |
| 9,108,979 B2 | 8/2015 | Davis et al. |
| 9,145,805 B2 | 9/2015 | Sato et al. |
| 9,156,766 B2 | 10/2015 | Boussie et al. |
| 9,156,805 B2 | 10/2015 | Shaikh et al. |
| 9,156,806 B2 | 10/2015 | Shaikh et al. |
| 9,162,998 B2 | 10/2015 | Backes et al. |
| 9,169,229 B2 | 10/2015 | Parker et al. |
| 9,181,157 B2 | 11/2015 | Allgeier et al. |
| 9,199,957 B2 | 12/2015 | Siqueira et al. |
| 9,199,958 B2 | 12/2015 | Janka et al. |
| 9,206,148 B2 | 12/2015 | Cho et al. |
| 9,206,149 B2 | 12/2015 | Janka et al. |
| 9,227,904 B1 | 1/2016 | Hong et al. |
| 9,228,051 B2 | 1/2016 | Carman, jr. et al. |
| 9,238,635 B2 | 1/2016 | Essayem et al. |
| 9,249,118 B2 | 2/2016 | Janka et al. |
| 9,260,403 B2 | 2/2016 | Yoshikuni et al. |
| 9,266,850 B2 | 2/2016 | Janka et al. |
| 9,309,181 B2 | 4/2016 | Chwae et al. |
| 9,321,744 B1 | 4/2016 | Hsu et al. |
| 9,376,414 B2 | 6/2016 | Van haveren et al. |
| 9,388,116 B2 | 7/2016 | Stensrud et al. |
| 9,388,152 B2 | 7/2016 | Ibert et al. |
| 9,416,119 B2 | 8/2016 | Bloom et al. |
| 9,422,258 B2 | 8/2016 | Bloom et al. |
| 9,428,480 B2 | 8/2016 | Janka et al. |
| 9,458,122 B2 | 10/2016 | Shaikh et al. |
| 9,464,026 B2 | 10/2016 | Stensrud et al. |
| 9,468,908 B2 | 10/2016 | Salem et al. |
| 9,475,787 B2 | 10/2016 | Mihovilovic et al. |
| 9,499,506 B2 | 11/2016 | Besson et al. |

(56) References Cited

U.S. PATENT DOCUMENTS

| | | |
|---|---|---|
| 9,506,060 B2 | 11/2016 | Bandaru et al. |
| 9,506,090 B2 | 11/2016 | Kambourakis et al. |
| 9,528,133 B2 | 12/2016 | Kambourakis et al. |
| 9,586,923 B2 | 3/2017 | Subramaniam et al. |
| 9,611,241 B2 | 4/2017 | Boussie et al. |
| 9,617,234 B1 | 4/2017 | Dumesic et al. |
| 9,643,945 B2 | 5/2017 | Mazoyer et al. |
| 9,670,118 B2 | 6/2017 | Allgeier et al. |
| 9,682,368 B2 | 6/2017 | Dias et al. |
| 9,701,652 B2 | 7/2017 | Miller et al. |
| 9,765,045 B2 | 9/2017 | Stensrud et al. |
| 9,783,516 B2 | 10/2017 | Bloom et al. |
| 10,017,486 B2 | 7/2018 | Boussie et al. |
| 10,093,638 B2 | 10/2018 | Masuno et al. |
| 10,208,006 B2 | 2/2019 | Sokolovskii et al. |
| 10,351,544 B2 | 7/2019 | Almeida et al. |
| 10,385,033 B2 | 8/2019 | Gordillo et al. |
| 10,442,780 B2 | 10/2019 | Sokolovskii et al. |
| 10,457,657 B2 | 10/2019 | Metkar et al. |
| 10,464,913 B2 | 11/2019 | Almeida et al. |
| 10,538,499 B2 | 1/2020 | Howard et al. |
| 10,654,819 B2 | 5/2020 | Sokolovskii et al. |
| 2006/0084800 A1 | 4/2006 | Chenault |
| 2007/0027341 A1 | 2/2007 | Rossi et al. |
| 2007/0179312 A1 | 8/2007 | O'Meadhra et al. |
| 2008/0081883 A1 | 4/2008 | King et al. |
| 2009/0030215 A1 | 1/2009 | Dignan et al. |
| 2009/0131690 A1 | 5/2009 | Gruter et al. |
| 2009/0156841 A1 | 6/2009 | Sanborn et al. |
| 2009/0306415 A1 | 12/2009 | Gruter et al. |
| 2009/0311568 A1 | 12/2009 | Yamada |
| 2010/0004437 A1 | 1/2010 | Binder et al. |
| 2010/0052469 A1 | 3/2010 | Naruse et al. |
| 2010/0058650 A1 | 3/2010 | Gruter et al. |
| 2010/0081833 A1 | 4/2010 | Gruter et al. |
| 2010/0083565 A1 | 4/2010 | Gruter et al. |
| 2010/0178584 A1 | 7/2010 | Hibino et al. |
| 2010/0196802 A1 | 8/2010 | Tabata et al. |
| 2010/0212217 A1 | 8/2010 | Gruter et al. |
| 2010/0212218 A1 | 8/2010 | Gruter |
| 2010/0218415 A1 | 9/2010 | Gruter et al. |
| 2010/0218416 A1 | 9/2010 | Gruter |
| 2010/0299991 A1 | 12/2010 | Gruter |
| 2010/0317822 A1 | 12/2010 | Boussie et al. |
| 2010/0317879 A1 | 12/2010 | Zhao et al. |
| 2011/0082304 A1 | 4/2011 | Gruter et al. |
| 2011/0282020 A1 | 11/2011 | Sipos |
| 2011/0302826 A1 | 12/2011 | Gruter |
| 2011/0306790 A1 | 12/2011 | Murphy et al. |
| 2012/0083610 A1 | 4/2012 | Gruter et al. |
| 2012/0237855 A1 | 9/2012 | Hucul et al. |
| 2012/0271060 A1 | 10/2012 | Muñoz de Diego et al. |
| 2012/0282352 A1 | 11/2012 | Lewis et al. |
| 2012/0302768 A1 | 11/2012 | Janka et al. |
| 2012/0302773 A1 | 11/2012 | Janka et al. |
| 2013/0095263 A1 | 4/2013 | Carman, jr. et al. |
| 2013/0137882 A1 | 5/2013 | Borsotti et al. |
| 2013/0171397 A1 | 7/2013 | Ghosh et al. |
| 2013/0184495 A1 | 7/2013 | Dias et al. |
| 2013/0295485 A1 | 11/2013 | Gottesfeld et al. |
| 2013/0324708 A1 | 12/2013 | De Sousa Dias et al. |
| 2014/0024844 A1 | 1/2014 | Janka et al. |
| 2014/0073805 A1 | 3/2014 | Franke et al. |
| 2014/0121389 A1 | 5/2014 | Essayem et al. |
| 2014/0142328 A1 | 5/2014 | Shaikh et al. |
| 2014/0205786 A1 | 7/2014 | Nederberg et al. |
| 2014/0235880 A1 | 8/2014 | Shaikh et al. |
| 2014/0271446 A1 | 9/2014 | Desmedt et al. |
| 2014/0295508 A1 | 10/2014 | Yoshikuni et al. |
| 2014/0302982 A1 | 10/2014 | Liu et al. |
| 2014/0315262 A1 | 10/2014 | Sanborn et al. |
| 2014/0343305 A1 | 11/2014 | Subramaniam et al. |
| 2014/0349351 A1 | 11/2014 | Jensen et al. |
| 2014/0364631 A1 | 12/2014 | Davis et al. |
| 2014/0371413 A1 | 12/2014 | Miura et al. |
| 2015/0010965 A1 | 1/2015 | Ertl et al. |
| 2015/0031904 A1 | 1/2015 | Cho et al. |
| 2015/0045576 A1 | 2/2015 | Benecke et al. |
| 2015/0048274 A1 | 2/2015 | Eyal et al. |
| 2015/0051412 A1 | 2/2015 | Janka et al. |
| 2015/0087848 A1 | 3/2015 | Oyola et al. |
| 2015/0110983 A1 | 4/2015 | Kriegel et al. |
| 2015/0119588 A1 | 4/2015 | van Haveren et al. |
| 2015/0126731 A1 | 5/2015 | Essayem et al. |
| 2015/0141584 A1 | 5/2015 | Saywell et al. |
| 2015/0183755 A1 | 7/2015 | Subramaniam et al. |
| 2015/0218118 A1 | 8/2015 | Mihovilovic et al. |
| 2015/0232498 A1 | 8/2015 | Riisager et al. |
| 2015/0274687 A1 | 10/2015 | Ibert et al. |
| 2015/0299095 A1 | 10/2015 | Stensrud et al. |
| 2015/0321119 A1 | 11/2015 | Parker et al. |
| 2015/0321180 A1 | 11/2015 | Parker et al. |
| 2015/0322028 A1 | 11/2015 | Janka et al. |
| 2015/0322029 A1 | 11/2015 | Janka et al. |
| 2015/0329927 A1 | 11/2015 | Parekh |
| 2015/0336090 A1 | 11/2015 | Kanna et al. |
| 2015/0193364 A1 | 12/2015 | Blocksome et al. |
| 2015/0376154 A1 | 12/2015 | Besson et al. |
| 2016/0009015 A1 | 1/2016 | Bouffand et al. |
| 2016/0016926 A1 | 1/2016 | Sanborn |
| 2016/0024039 A1 | 1/2016 | Mazoyer et al. |
| 2016/0028093 A1 | 1/2016 | Pietrasz et al. |
| 2016/0075672 A1 | 3/2016 | Van Haveren et al. |
| 2016/0130244 A1 | 5/2016 | Janka et al. |
| 2016/0145662 A1 | 5/2016 | Van Spronsen et al. |
| 2016/0207898 A1 | 7/2016 | Singh et al. |
| 2016/0207899 A1 | 7/2016 | Yi et al. |
| 2016/0221979 A1 | 8/2016 | Yashiro et al. |
| 2016/0221980 A1 | 8/2016 | Parker et al. |
| 2016/0289161 A1 | 10/2016 | Stensrud et al. |
| 2016/0311790 A1 | 10/2016 | Janka et al. |
| 2016/0332979 A1 | 11/2016 | Fontenot et al. |
| 2017/0015643 A1 | 1/2017 | Venkitasubramanian et al. |
| 2017/0050119 A1 | 2/2017 | Roa Engel et al. |
| 2017/0050944 A1 | 2/2017 | Kambourakis et al. |
| 2017/0088865 A1 | 3/2017 | Kambourakis et al. |
| 2017/0137363 A1 | 5/2017 | Asikainen et al. |
| 2017/0144982 A1 | 5/2017 | Miller et al. |
| 2017/0157530 A1 | 6/2017 | Parker et al. |
| 2017/0197930 A1 | 7/2017 | Sokolovskii et al. |
| 2017/0226144 A1 | 8/2017 | Kuo et al. |
| 2017/0260154 A1 | 9/2017 | Janka et al. |
| 2017/0305873 A1 | 10/2017 | Miller et al. |
| 2017/0313670 A1 | 11/2017 | De Sousa Dias et al. |
| 2018/0093894 A1 | 4/2018 | Smith et al. |
| 2018/0222877 A1 | 8/2018 | Metkar et al. |
| 2019/0016658 A1 | 1/2019 | Mullen et al. |
| 2019/0031797 A1 | 1/2019 | Dyson et al. |
| 2019/0083960 A1 | 3/2019 | Kim et al. |
| 2019/0119238 A1 | 4/2019 | Metkar et al. |
| 2019/0233386 A1 | 8/2019 | Sokolovskii et al. |
| 2019/0270717 A1 | 9/2019 | Masuno et al. |
| 2019/0300494 A1 | 10/2019 | Metkar et al. |
| 2019/0389826 A1 | 12/2019 | Metkar et al. |
| 2020/0002300 A1 | 1/2020 | Kunz et al. |
| 2020/0010441 A1 | 1/2020 | Sokolovskii et al. |
| 2020/0223812 A1 | 7/2020 | den Ouden et al. |

FOREIGN PATENT DOCUMENTS

| | | |
|---|---|---|
| CA | 2097821 | 1/1997 |
| CN | 102190785 | 9/2001 |
| CN | 101899145 | 12/2010 |
| CN | 102827361 | 12/2012 |
| CN | 103570926 | 2/2014 |
| CN | 103965146 | 8/2014 |
| EP | 1834950 A1 | 9/2007 |
| EP | 2053047 A1 | 4/2009 |
| EP | 2103606 A1 | 9/2009 |
| EP | 2105438 A1 | 9/2009 |
| EP | 2050742 B1 | 7/2010 |
| EP | 2105439 B1 | 10/2011 |
| EP | 2390247 A1 | 11/2011 |
| EP | 2455373 A1 | 5/2012 |

(56) References Cited

FOREIGN PATENT DOCUMENTS

| | | |
|---|---|---|
| EP | 2487170 A1 | 8/2012 |
| EP | 2565189 A1 | 3/2013 |
| EP | 2703395 A1 | 3/2014 |
| EP | 2864302 B1 | 4/2015 |
| EP | 2864304 | 4/2015 |
| EP | 2864305 | 4/2015 |
| EP | 2864306 | 4/2015 |
| EP | 3015463 A1 | 5/2016 |
| EP | 2784069 B1 | 7/2016 |
| EP | 2714671 B1 | 9/2016 |
| EP | 2423205 B1 | 10/2016 |
| EP | 3137184 | 3/2017 |
| EP | 2953937 | 9/2017 |
| FR | 2663933 A1 | 1/1992 |
| FR | 2664273 A1 | 1/1992 |
| FR | 2669634 | 5/1992 |
| FR | 2669635 B1 | 6/1994 |
| FR | 2723946 | 3/1996 |
| GB | 591858 A1 | 9/1947 |
| GB | 600871 A1 | 4/1948 |
| GB | 876463 A1 | 9/1961 |
| JP | 2006-328374 | 12/2006 |
| JP | 2012-144744 | 8/2012 |
| JP | 5120944 B2 | 1/2013 |
| JP | 2013-155388 | 8/2013 |
| JP | 5311778 B2 | 10/2013 |
| JP | 5446121 B2 | 3/2014 |
| KR | 2012107573 | 10/2012 |
| WO | WO 1992/10486 | 6/1992 |
| WO | WO 2007/104514 | 9/2007 |
| WO | WO 2007/104515 | 9/2007 |
| WO | WO 2008/054804 | 5/2008 |
| WO | WO 2009/030504 | 3/2009 |
| WO | WO 2009/030506 | 3/2009 |
| WO | WO 2009/030507 | 3/2009 |
| WO | WO 2009/030508 | 3/2009 |
| WO | WO 2009/030509 | 3/2009 |
| WO | WO 2009/030511 | 3/2009 |
| WO | WO 2009/141166 | 11/2009 |
| WO | WO 2010/077133 | 7/2010 |
| WO | WO 2010/132740 | 11/2010 |
| WO | WO 2011/043660 | 4/2011 |
| WO | WO 2011/043661 | 4/2011 |
| WO | WO 2011/149339 | 12/2011 |
| WO | WO 2011/155964 | 12/2011 |
| WO | WO 2012/015616 | 2/2012 |
| WO | WO 2012/091570 | 7/2012 |
| WO | WO 2012/091573 | 7/2012 |
| WO | WO 2012/156479 | 11/2012 |
| WO | WO 2012/161967 | 11/2012 |
| WO | WO 2012/161970 | 11/2012 |
| WO | WO 2013/034763 | 3/2013 |
| WO | WO 2013/048248 | 4/2013 |
| WO | WO 2013/053816 | 4/2013 |
| WO | WO 2013/062408 | 5/2013 |
| WO | WO 2013/095263 | 6/2013 |
| WO | WO 2013/100768 | 7/2013 |
| WO | WO 2013/103574 | 7/2013 |
| WO | WO 2013/106136 | 7/2013 |
| WO | WO 2013/117585 | 8/2013 |
| WO | WO 2013/120989 | 8/2013 |
| WO | WO 2013/133489 | 9/2013 |
| WO | WO 2013/144525 | 10/2013 |
| WO | WO 2013/191944 | 12/2013 |
| WO | WO 2014/032731 | 3/2014 |
| WO | WO 2014/033289 | 3/2014 |
| WO | WO 2014/037560 | 3/2014 |
| WO | WO 2014/058859 | 4/2014 |
| WO | WO 2014/074482 | 5/2014 |
| WO | WO 2014/100254 | 6/2014 |
| WO | WO 2014/100256 | 6/2014 |
| WO | WO 2014/100257 | 6/2014 |
| WO | WO 2014/100265 | 6/2014 |
| WO | WO 2014/102413 | 7/2014 |
| WO | WO 2014/122319 | 8/2014 |
| WO | WO 2014/152366 | 9/2014 |
| WO | WO 2014/158838 | 10/2014 |
| WO | WO 2014/163500 | 10/2014 |
| WO | WO 2014/173973 | 10/2014 |
| WO | WO 2014/182171 | 11/2014 |
| WO | WO 2014/204296 | 12/2014 |
| WO | WO 2014/204313 | 12/2014 |
| WO | WO 2014/209112 | 12/2014 |
| WO | WO 2015/015243 | 2/2015 |
| WO | WO 2015/030590 | 3/2015 |
| WO | WO 2015/031910 | 3/2015 |
| WO | WO 2015/041601 | 3/2015 |
| WO | WO 2015/056270 | 4/2015 |
| WO | WO 2015/066570 | 5/2015 |
| WO | WO 2015/088341 | 6/2015 |
| WO | WO 2015/113060 | 7/2015 |
| WO | WO 2015/168327 | 11/2015 |
| WO | WO 2015/171704 | 11/2015 |
| WO | WO 2015/189481 | 12/2015 |
| WO | WO 2015/197699 | 12/2015 |
| WO | WO 2019/229077 | 12/2015 |
| WO | WO 2016/053186 | 4/2016 |
| WO | WO 2016/057628 | 4/2016 |
| WO | WO 2016/057673 | 4/2016 |
| WO | WO 2016/057676 | 4/2016 |
| WO | WO 2016/057682 | 4/2016 |
| WO | WO 2016/057687 | 4/2016 |
| WO | WO 2016/059205 | 4/2016 |
| WO | WO 2016/068712 | 5/2016 |
| WO | WO 2016/076710 | 5/2016 |
| WO | WO 2016/076711 | 5/2016 |
| WO | WO 2016/133384 | 8/2016 |
| WO | WO 2016/141148 | 9/2016 |
| WO | WO 2016/146752 | 9/2016 |
| WO | WO 2016/146753 | 9/2016 |
| WO | WO 2016/166421 | 10/2016 |
| WO | WO 2016/168233 | 10/2016 |
| WO | WO 2016/186278 | 11/2016 |
| WO | WO 2016/195499 | 12/2016 |
| WO | WO 2016/195500 | 12/2016 |
| WO | WO 2016/196499 | 12/2016 |
| WO | WO 2017/019431 | 2/2017 |
| WO | WO 2017/019441 | 2/2017 |
| WO | WO 2017/019444 | 2/2017 |
| WO | WO 2017/019445 | 2/2017 |
| WO | WO 2017/019447 | 2/2017 |
| WO | WO 2017/030668 | 2/2017 |
| WO | WO 2017/034985 | 3/2017 |
| WO | WO 2017/050815 | 3/2017 |
| WO | WO 2017/075391 | 5/2017 |
| WO | WO 2017/075425 | 5/2017 |
| WO | WO 2017/083297 | 5/2017 |
| WO | WO 2017/097843 | 6/2017 |
| WO | WO 2017/123763 | 7/2017 |
| WO | WO 2017/155286 | 9/2017 |
| WO | WO 2019/014382 | 1/2019 |
| WO | WO 2019/058270 | 3/2019 |
| WO | WO 2019/072920 | 4/2019 |
| WO | WO 2019/089448 | 5/2019 |
| WO | WO 2019/185646 | 10/2019 |
| WO | WO 2019/229080 | 12/2019 |
| WO | WO 2020/011996 | 1/2020 |

OTHER PUBLICATIONS

Aiken et al., 2012, Molecular Mapping of the Acid Catalysed Dehydration of Fructose Chem. Commun., 48:5850-5852 and Supplemental Information.

Amarasekara et al., 2013, Synthesis and Characterization of All Renewable Resources Based Branched Polyester: Poly(2,5-furandicarboxylic acid-co-glycerol) ISRN Polymer Science, vol. 2013, Article ID 645169.

Artz et al., 2015, Selective Aerobic Oxidation of HMF to 2,5-Diformylfuran on Covalent Triazine Frameworks-Supported Ru Catalysts, ChemSusChem. 8(4):672-679.

Bari, Mar. 15-18, 2016, The 100% Bio-Based Replacement for PET! Presented at the 31st Annual World Petrochemical Conference, Houston, TX, in 28 pages.

(56) References Cited

OTHER PUBLICATIONS

Barrett et al., 1951, The determination of pore volume and area distributions in porous substances. I. Computations from nitrogen isotherms, J. Am. Chem. Soc. 73:373-380.
Besson et al., 2000, Selective oxidation of alcohols and aldehydes on metal catalysts, 57:127-141.
Bratuescu, 2000, Cyclisation under the Action of the Microwaves of the D-Saccaric acid to 2,5-Furandicarboxylic acid. Revue Roumaine de Chimie, 45(9):883-885 (Article in French).
Brunauer et al., 1938, Adsorption of bases in multimolecular layers, J Am Chem Soc. 60:309-311.
Caes et al., 2011, Conversion of fructose into 5-(hydroxymethyl)furfural in sulfolane, ChemSusChem, 4:353-356.
Casanova et al., 2009, Biomass into Chemicals: Aerobic Oxidation of 5-Hydroxymethyl-2-furfural into 2,5-Furandicarboxylic Acid with Gold Nanoparticle Catalysts, ChemSusChem, 2(12):1138-1144; Abstract Only.
Casanova et al., 2009, Biomass into Chemicals: One pot-base free oxidative esterification of 5-hydroxymethyl-2-furfural into 2,5-dimethylfuroate with gold on nanoparticulated ceria, J Catalysis, 265(1):109-116.
Cope et al., Jan. 1956, Benzofuran from saccharic acid, Notes, p. 141.
Corma et al., 2007, Chemical routes for the Transformation of Biomass into Chemicals, Chem Rev., 107:2411-2502.
Davis et al., 2011, Oxidation of 5-hydroxymethylfurfural over supported Pt, Pd and Au catalysts, Catalysis Today 160(1):55-66; Abstract Only.
Davis S.E., 2012, 5-Hydroxymethylfurfural Oxidation on Supported Metal Catalysts, Dissertation, University of Virginia, 130 pp.
De Jong et al., 2012, Furandicarboxylic Acid (FDCA), A Versatile Building Block for a Very Interesting Class of Polyesters In Biobased Monomers, Polymers, and Materials, Smith et al. [Eds.], Chapter 1; ACS Symposium Series; American Chemical Society, Washington, D.C. in 13 pages.
Diamond et al., 2013, Application of high trhoughput experimentation to the production fo commodity chemicals from renewable feedstocks, in Modern Applications of High Throughput R&D in Heterogeneous Catalysis, Hagemeyer et al., [Eds.], Bentham Science Publishers, Chapter 8, pp. 299-309.
Gattinger et al., Nov. 16, 2016, Presentation #466868: Cyclization and Dehydration of Aldaric Acids to 2,5-Furandicarboxylic Acid, at the Annual Meeting of AiChE, San Francisco, CA—Abstract Only.
Gorbanev et al., 2011, Selective Aerobic Oxidation of 5-Hydroxymethylfurfural in Water Over Solid Ruthenium Hydroxide Catalysts with Magnesium-based Supports, Catal Lett. 141:1752-1760; Abstract Only.
Gruter et al., 2012, Accelerating research into bio-based FDCA-polyesters by using small scale parallel film reactors, Comb. Chem. High Throughput Screening,15:180-188.
Gupta et al., 2011, Hydrotalcite-supported gold-nanoparticle-catalysted highly efficient base-free aqueous oxidation of 5-hydroxymethylfurfural into 2,5-furandicarboxylic acid under atmospheric oxygen pressure Green Chem., 13:824-827 and Supplementary Material in 11 pages.
Han et al., 2016, Base-free aerobic oxidation of 5-hydroxymethylfurfural to 2,5-furandicarboxylic acid over a Pt/C—O—Mg catalyst, Green Chem. 18(6):1597-1604.
Kazi et al., 2011, Techno-economic Analysis of Dimethylfuran (DMF) and Hydroxymethylfurfural (HMF) Production from Pure Fructose in Catalytic Processes, Chem Eng J., 169:329-338.
Kimura et al., 1993, Selective oxidation of glycerol on a platinum-bismuth catalyst, Applied Catalysis A: General 96(2):217-228.
Koopman et al., Apr. 2010, Efficient whole-cell biotransformation of 5-(hydroxymethyl)furfural into FDCA, 2,5-furandicarboxylic acid, Bioresource Technology, 101:6291-6296.
Kröger et al., 2000, A new approach for the production of 2,5-furandicarboxylic acid by in situ oxidation of 5-hydroxymethylfurfural starting from fructose, Topics in Catalysis, 13:237-242.
Lu et al., 2013, Aerobic oxidation of primary aliphatic alcohols over bismuth oxide supported platinum catalysts in water, Green Chem., 15:2215-2221.
MacFarlane et al., 2007, Ionic liquids—Progress on the Fundamental Issues, Aust J Chem., 60:3-5.
Mallat et al., 1994, Partial Oxidation of cinnamyl alcohol on bimetallic catalysts of improved resistance to self-poisoning, in Studies in Surface Science and Catalysis, Corberan et al. [Eds.], Elsevier; 82:561-570.
Mallat et al., 1994, Platinum-catalyzed oxidation of alcohols in aqueous solutions. The role of Bi-promotion in suppression of catalyst deactivation, in Catalyst Deactivation—Studies in Surface Science & Catalysis; Delmon et al. [Eds.], vol. 88, pp. 385-389.
Mallat et al., 1998, Aerobic Oxidation of alpha-substituted alcohols over promoted plantinum metal catalysts, in Supported Reagents and Catalysts in Chemistry, Hodnett [Ed.]; pp. 66-71.
March's Advanced Organic Chemistry, M. B. Smith et al., [Eds.]; 7th Edition, Wiley (2013); TOC.
Modern Polyesters: Chemistry and Technology of Polyesters and Copolyesters, J. Scheirs et al., [Eds.]; Wiley (2003); TOC.
Pavone, Jun. 2016, Bio-Based Furan Dicarboxylic Acid (FDCA) and Its Polymer Polyethylene Furanoate (PEF), HIS Chemical, PEP Report 294, in 409 pages.
Payne et al., 2010, Solubility of bio-sources feedstocks in 'green' solvents, Green Chem, 12:1648-1653.
Ragauskas et al., 2006, The Path Forward for Biofuels and Biomaterials, Science 311:484-489.
Rasrendra et al., 2013, Experimental studies on the pyrolysis of humins from the acid-catalysed dehydration of C6-sugars, J Analyt Appl Pyrolysis. 104:299-307. (2013) 104:299-307.
Rass et al., 2013, Selective aqueous phase oxidation of 5-hydroxymethylfurfural to 2,5-furandicarboxylic acid over Pt/C catalysts: influence of the base and effect of bismuth promotion, Green Chem, 15:2240-2251.
Rass et al., 2015, Selective aerobic oxidation of 5-HMF into 2,5-furandicarboxylic acide with Pt catalysts supported on Ti02- and Zr02-based supports, ChemSusChem, 8:1206-1217.
Rogers et al., 2007, Ionic Liquids, Accounts of Chemical Research 40(11):1077-1078.
Shiramizu et al., 2013, Expanding the Scope of Biomass-Derived Chemicals through Tandem Reactions based on Oxorhenium-catalyzed Deoxydehydration, Angew Chem Int Ed. 52(49):12905-12909.
Sigma-Aldrich®, Jun. 22, 2010, 2,5-Furandicarboxylic acid—97%, Product Specification, 1 p.
Sixta H., Jun. 19-22, 2017, Advances in Biorefinery: 7-Furan Biorefinery; Aalto University School of Chemical Technology, Finland; PPPresentation for Course/CHEM-L2020 in 89 pages.
Sousa et al., Sep. 2015, Biobased polyesters and other polymers from 2,5-furandicarboxylic acid: a tribute to furan excellency, Polym Chem., 6(33):5961-5983.
Szmant et al., 1981, The Preparation of 5-Hydroxymethylfurfuraidehyde from High Fructose Corn Syrup and Other Carbohydrates, J Chem Tech Biotech. 31(1):135-145, Abstract only.
Teong et al., 2014, Poly-benzylic ammonium chloride resins as solid catalysts for fructose dehydration, ChemSusChem, 7:2120-2126.
Tong et al., 2011, Defunctionalization of fructose and sucrose: iron-catalyzed production of 5-hydroxymethylfurfural from fructose and sucrose, Catalysis Today, 175:524-527.
Trieble, Aug. 2012, Simulation and Economic Analysis of 5-Hydroxymethylfurfural Conversion to 2,5-Furandicarboxylic Acid, Dipl. Ing. Thesis (Leoben University of Mining) in 143 pages.
Tucker et al., 2012, Acid-Functionalized SBA-15-Type Periodic Mesoporous Organosilicas and Their Use in the Continuous Production of 5-Hydroxymethylfurfural, ACS Catalysis, 2:1865-1876 and Supporting Documentation in 15 pages.
U.S. EPA, Office of Water, Nov. 2005, Membrane Filtration Guidance Manual, EPA 815-R-06-009, 332 pp.
Van Putten et al., 2013, Hydroxymethylfurfural, A Versatile Platform Chemical Made from Renewable Resources Chem. Rev., 113:1499-1597.

(56) References Cited

OTHER PUBLICATIONS

Verdeguer, et al., 1993, Oxydation catalytique du HMF en acide 2,5-furane dicarboxylique, Journal of Molecular Catalysis, 85:327-344.

Villa et al., 2013, Pd-modified Au on Carbon as an Effective and Durable Catalyst for the Direct Oxidation of HMF to 2,5-Furandicarboxylic Acid, Chem. Sus. Chem., 6:609-612.

Vinke et al., 1990, Platinum catalyzed oxidation of 5-hydroxymethylfurfural, Studies in Surface Science & Catalysis, 55:147-158.

Wan et al., 2014, Base-Free Aerobic Oxidation of 5-Hydroxymethylfurfural to 2,5-Furandicarboxylic Acid in Water Catalyzed by Functionalized Carbon Nanotube-Supported Au-Pd Alloy Nanoparticles ACS Catal., 4(7):2175-2185 and Supporting Information in 17 pages.

Werpy et al. (Eds.), 2004, Top Value Added Chemicals from Biomass vol. 1: Results of Screening for Potential Candidates from Sugars and Synthesis Gas, U.S. Dept. of Energy, Office of Scientific Information: Oak Ridge, Tenn. DOE/GO-102004-1992, 76 pp.

Wilkes, 2002, A short history of ionic liquides—from molten salts to neoteric solvents, Green Chemistry, 4:73-80.

Xie et al., 2016, Influence of Dioxygen on the Promotional Effect of Bi during Pt-Catalyzed Oxidation of 1,6-Hexnediol, ACS Catal. 6:4206-4217.

Yang et al. 2015, Effect of organic solvent and Brønsted acid on 5-hydroxymethylfurfural preparation from glucose over CrCI3. RSC Adv. 5:27805-27813.

Zhang et al., 2015, Advances in catalytic production of bio-based polyester monomer 2,5-furandicarboxylic acid derived from ilgnocellulosic biomass, Carbohyd Polymers 130:420-428.

International Search Report and Written Opinion dated May 10, 2017 in PCT/US2017/013197.

European Supplement Partial Search Report dated Jul. 23, 2019 for Application No. EP 17738935.

International Search Report and Written Opinion dated Oct. 1, 2018 in PCT/US2018/041694.

International Search Report and Written Opinion dated Dec. 4, 2018 in PCT/US2018/041707.

PROCESSES FOR THE PREPARATION OF 2,5-FURANDICARBOXYLIC ACID AND INTERMEDIATES AND DERIVATIVES THEREOF

CROSS-REFERENCE TO RELATED APPLICATIONS

This application is a continuation application of, and claims the benefit of priority to, U.S. Non-Provisional application Ser. No. 16/552,096, filed Aug. 27, 2019, which is a continuation of and claims the benefit of priority to U.S. Non-Provisional application Ser. No. 16/264,188, filed Jan. 31, 2019, now U.S. Pat. No. 10,442,780, which is a continuation of and claims the benefit of priority to U.S. Non-Provisional application Ser. No. 15/404,996, filed Jan. 12, 2017, now U.S. Pat. No. 10,208,006, and U.S. Provisional Application No. 62/278,332, filed Jan. 13, 2016, whereby each of the aforementioned applications is expressly incorporated by reference in its entirety.

FIELD

The present disclosure relates to novel processes for preparing 2,5-furandicarboxylic acid pathway products, as well as related esters, amides, polymers, and compositions thereof.

BACKGROUND

Low cost, renewably-derived 2,5-furandicarboxylic acid (FDCA) and its derivatives harbor considerable potential for commercial applications. See, e.g., "Top Value Added Chemicals from Biomass," Volume I—Results of Screening for Potential Candidates from Sugars and Synthesis Gas, produced by Staff at Pacific Northwest National Laboratory (PNNL), National Renewable Energy Laboratory (NREL), Office of Biomass Program (EERE); Eds. T. Werpy and G. Petersen (2003). In certain applications, they have the potential to displace aromatic dicarboxylic acids such as terephthalic and isophthalic acid. A. Corma, et al., Chem. Rev., 107:2411 (2007). FDCA and its derivatives are also useful in the production of other commodity chemicals. Id. For example, FDCA may be hydrogenated to adipic acid, which is utilized in the production of nylon. Id. Aromatic dicarboxylic acids are used for the production of polyesters and polyamides in the scale of tens of millions of tons per year. See, e.g., "Modern Polyesters: Chemistry and Technology of Polyesters and Copolyesters," Eds. J. Scheirs and T. Long; Wiley (2013).

Methods of producing FDCA have been reported in the literature. For example, Corma, et al., report that FDCA can be produced by direct oxidation of 5-hydroxymethylfurfural (HMF) with nitric acid, though with low selectivity and yield. A. Corma, et al., supra. Verdeguer, et al. describe another process in which HMF is oxidized catalytically to FDCA using 5% Pt supported on carbon in the presence of sodium or potassium hydroxides with yields reported to be 70%. J. Mol. Catal. 85:327 (1993). They reported achieving FDCA yields of up to 80% using a 5% Pt/5% Pb catalyst formulation on carbon in the presence of 1.25 M base solution. Id. When the amount of base was reduced to a concentration of 0.1 M, the authors reported that no conversion of HMF to FDCA was achieved, suggesting high concentrations of base are an important requirement for achieving higher FDCA yields. See Id. In another reported method, Besson, et al., report that Pt/Bi catalysts supported on carbon can produce FDCA with close to 100% selectivity under reaction conditions of a high base ($Na_2CO_3$) to HMF ratio of 2 to 4. See WO 2014/122319. An ancillary result of adding a base (e.g., NaOH, KOH, $Na_2CO_3$) to the reaction is the formation of salts (e.g., sodium or potassium salts) of FDCA. The formation of FDCA salts may be advantageous given that FDCA salts are reported to be more water-soluble than FDCA itself, thereby affording the potential opportunity to carry out the conversion process at higher HMF concentrations. Id. However, a disadvantage of such salt production is the need for further processing (e.g., further separation and/or conversion of the salt form of FDCA to FDCA) in the recovery of FDCA.

U.S. Pat. No. 8,338,626 describes the production of FDCA and its esters by oxidation of mono- or dialkoxymethylfurfural in the presence of a homogeneous catalytic system that is similar to the system used in terephthalic acid production (Co/Mn/Br). The patent reports a maximum total yield of furandicarboxylics (with FDCA as a major constituent) of 82%. Id. U.S. Pat. No. 7,700,788 describes a method of HMF oxidation to FDCA under high oxygen (air) pressure using a 5% $Pt/ZrO_2$ catalyst, prepared by a specific procedure from Pt acetylacetonate. In this process, HMF at a concentration of three weight percent, in the presence of base, and oxygen at a pressure of 150 psi resulted in the production of FDCA at a yield of 90%.

U.S. Pat. No. 4,977,283 describes the oxidation of HMF at concentrations around 10% in a base-free solution of water and diethylene glycol dimethyl ether in the presence of a Pt (5%) on activated carbon catalyst. The process provided only low yields (8%) of FDCA with the major product being 5-formylfuran-2-carboxylic acid.

In view of its potential as a biorenewable-derived replacement for petroleum-derived compounds that are used in the production of plastics and other materials, a commercially viable process for the production of large volumes of FDCA at high yields would be desirable.

SUMMARY

In one aspect, the present disclosure is directed to a process for producing a 2,5-furandicarboxylic acid (FDCA) pathway product from a furanic oxidation substrate, the process comprising:

(a) contacting an oxidation feedstock comprising a furanic oxidation substrate and an oxidation solvent with oxygen in the presence of a heterogeneous oxidation catalyst under conditions sufficient to form a reaction mixture for oxidizing the furanic oxidation substrate to an FDCA pathway product, and producing the FDCA pathway product, wherein the oxidation solvent is a solvent selected from the group consisting of an organic solvent and a multi-component solvent, wherein the reaction mixture is substantially free of added base, wherein the heterogeneous oxidation catalyst comprises a solid support and a noble metal, and wherein the heterogeneous oxidation catalyst comprises a plurality of pores and a specific surface area in the range of from 20 $m^2/g$ to 500 $m^2/g$. The noble metal can be platinum, gold, or a combination thereof. The oxidation solvent can be a multi-component solvent comprising water and a water-miscible aprotic organic solvent. The water-miscible organic solvent can be a water-miscible aprotic organic solvent. The water-miscible aprotic organic solvent can be selected from the group consisting of tetrahydrofuran, a glyme, dioxane, a dioxolane, dimethylformamide, dimethylsulfoxide, sulfolane, acetone, N-methyl-2-pyrrolidone ("NMP"), methyl ethyl ketone ("MEK"), and gamma-valerolactone. The glyme can be selected from the group consisting of a monoglyme (1,2-dimethoxyethane), ethyl glyme, diglyme (diethylene glycol dimethyl ether), ethyl diglyme, triglyme, butyl diglyme, tetraglyme, and a polyglyme. The water-miscible organic solvent can be selected from the group consisting of a light water-miscible organic solvent and a heavy water-miscible organic solvent. The water and the water-miscible organic solvent can be present in a ratio of from or any number in between 1:6 to 6:1 v/v water:water-miscible organic solvent. The water and the water-miscible organic solvent can be present in a ratio of 1:1 v/v water:water-miscible organic solvent. The water-miscible organic solvent can be at least 10 vol % of the multi-component solvent.

The oxidation solvent can be a multi-component solvent comprising water and two different water-miscible organic solvents. The water-miscible organic solvents both can be water-miscible aprotic organic solvents. Each of the water-miscible aprotic organic solvents can be independently selected from the group consisting of tetrahydrofuran, a glyme, dioxane, a dioxolane, dimethylformamide, dimethylsulfoxide, sulfolane, acetone, N-methyl-2-pyrrolidone ("NMP"), methyl ethyl ketone ("MEK"), and gamma-valerolactone, The furanic oxidation substrate can be 5-(hydroxymethyl)furfural (HMF). The furanic oxidation substrate can be selected from the group consisting of diformylfuran (DFF), hydroxymethylfurancarboxylic acid (HMFCA), and formylfurancarboxylic acid (FFCA).

The oxidation feedstock can include the furanic oxidation substrate at a concentration of at least 5% by weight. The furanic oxidation substrate can be present in the oxidation feedstock at a concentration of at least 10% by weight.

The heterogeneous oxidation catalyst can comprise the metal at a loading in the range of from or any number in between 0.3% to 5% by weight of the heterogeneous oxidation catalyst. The heterogeneous oxidation catalyst can further comprise a promoter.

The solid support can comprise a material selected from the group consisting of a metal oxide, a carbonaceous material, a polymer, a metal silicate, a metal carbide, and any combination of two or more thereof. The metal oxide can be selected from the group consisting of silica, zirconia, and alumina. The carbonaceous material can be carbon black. The solid support can be a composite material comprising a binder and a material selected from the group consisting of a metal oxide, a carbonaceous material, a polymer, a metal silicate, and a metal carbide.

The heterogeneous oxidation catalyst can comprise a specific surface area in the range of from or any number in between 25 m$^2$/g to 350 m$^2$/g, from or any number in between 25 m$^2$/g to 250 m$^2$/g, from or any number in between 25 m$^2$/g to 225 m$^2$/g, from or any number in between 25 m$^2$/g to 200 m$^2$/g, from or any number in between 25 m$^2$/g to 175 m$^2$/g, from or any number in between 25 m$^2$/g to 150 m$^2$/g, from or any number in between 25 m$^2$/g to 125 m$^2$/g, or from or any number in between 25 m$^2$/g to 100 m$^2$/g. The heterogeneous oxidation catalyst can comprise a pore volume wherein at least 50% of the pore volume is from pores having a pore diameter in the range of from or any number in between 5 nm to 100 nm. The heterogeneous oxidation catalyst can comprise a pore volume wherein no more than 10% of the pore volume of the heterogeneous oxidation catalyst is from pores having a pore diameter less than 10 nm but not zero. The heterogeneous oxidation catalyst can comprise a pore volume where no more than 10% of the pore volume of the heterogeneous oxidation catalyst is from pores having a pore diameter ranging from or any number in between 0.1 nm to 10 nm. The heterogeneous oxidation catalyst can comprise a pore volume where no more than 5% of the pore volume of the heterogeneous oxidation catalyst is from pores having a pore diameter less than 10 nm but not zero. The pore volume of the heterogeneous oxidation catalyst can be no more than 5% of the pores having a pore diameter ranging from or any number in between 0.1 nm to 10 nm. The pore volume of the heterogeneous oxidation catalyst can be no more than 2.5% of the pores having a pore diameter less than 10 nm but not zero. The pore volume of the heterogeneous oxidation catalyst can be no more than 2.5% of the pores having a pore diameter ranging from or any number in between 0.1 nm to 10 nm. The plurality of pores can be characterized by a mean pore diameter in the range of from or any number in between 10 nm to 100 nm.

The heterogeneous oxidation catalyst can comprise a second plurality of pores, where at least one of the first or second pluralities of pores is characterized by a mean pore diameter in the range of from or any number in between 10 nm to 100 nm. Each of the first and second plurality of pores can be characterized by a mean pore diameter in the range of from or any number in between 10 nm to 100 nm.

The heterogeneous oxidation catalyst can comprise a specific pore volume that is in the range of from or any number in between 0.1 cm$^3$/g to 1.5 cm$^3$/g.

The oxygen can be present at a molar ratio of oxygen:furanic oxidation substrate in the range of from or any number in between 2:1 to 10:1. The molar ratio of oxygen:furanic oxidation substrate can be in the range of from or any number in between 2:1 to 5:1. The oxygen can be present at a pressure ($p_{O2}$) in the range of from or any number in between 50 psig to 1000 psig. The oxygen can be present at a pressure ($p_{O2}$) in the range of from or any number in between 50 psig to 200 psig.

The contacting step can be carried out at a temperature in the range of from or any number in between 50° C. to 200° C., in the range of from or any number in between 80° C. to 180° C., or in the range of from or any number in between 100° C. to 160° C. The FDCA pathway product can be produced at a yield of at least 80%. The FDCA pathway product can be produced at a selectivity of at least 90%. The contacting step can be carried out for a time sufficient to produce a product solution comprising the oxidation solvent and the FDCA pathway product at a concentration of at least 5% by weight. The contacting step can produce a product solution comprising the oxidation solvent and the FDCA pathway product at a concentration of at least 5% by weight.

The process can comprise a second oxidation step, wherein the second oxidation step comprises:

(b) contacting a second oxidation feedstock comprising a second furanic oxidation substrate and a second oxidation solvent with oxygen in the presence of a second heterogeneous oxidation catalyst under conditions sufficient to form a second reaction mixture for oxidizing the second furanic oxidation substrate to produce a second FDCA pathway product, and producing the second FDCA pathway product, wherein (the first) contacting step (a) produces a first FDCA pathway product that is an FDCA pathway intermediate compound, either alone or together with FDCA, wherein the second furanic oxidation substrate is the first FDCA pathway product, wherein the second reaction mixture is substantially free of added base, and wherein the second heterogeneous oxidation catalyst comprises a second solid support and a second noble metal, that may be the same or different from the (first) noble metal in step (a), and wherein the second heterogeneous oxidation catalyst comprises a plurality of pores and a specific surface area in the range of from or any number in between 20 m$^2$/g to 500 m$^2$/g.

The second noble metal can be selected from the group consisting of platinum, gold, and a combination thereof. The second heterogeneous oxidation catalyst can be the same as the (first) heterogeneous oxidation catalyst of step (a). The second heterogeneous oxidation catalyst can be different from the (first) heterogeneous oxidation catalyst of step (a). The second heterogeneous oxidation catalyst can comprise a second metal that is not the same as the (first) metal in the (first) heterogeneous oxidation catalyst of step (a). The (first) oxidation solvent in step (a) can be the same as the second oxidation solvent in step (b).

The process may recover the FDCA pathway product from the oxidation solvent in step (a). The process may recover the second FDCA pathway product from the second oxidation solvent in step (b). The process may involve purifying the FDCA pathway product from step (a). The process may involve purifying the second FDCA pathway product from step (b). The purifying step can comprise a crystallization process. The crystallization process can comprise providing a crystallization solution comprising the FDCA pathway product and a crystallization solvent at a first temperature in the range of from or any number in between 50° C. to 220° C., and cooling the crystallization solution to a second temperature that is lower than the first temperature to form a plurality of FDCA pathway product crystals of different particle sizes. The crystallization solvent can be the (first) oxidation solvent in step (a). The crystallization process can comprises providing a crystallization solution comprising the second FDCA pathway product and a crystallization solvent at a first temperature in the range of from or any number in between 50° C. to 220° C., and cooling the crystallization solution to a second temperature that is lower than the first temperature to form a plurality of second FDCA pathway product crystals of different particle sizes. The crystallization solvent can be selected from the group consisting of the first oxidation solvent of step (a) and the second oxidation solvent of step (b).

The process can include a crystallization process that comprises providing a first crystallization solution comprising the FDCA pathway product and a first crystallization solvent selected from the group consisting of water, an organic solvent, and combinations thereof; and removing a first portion of the first crystallization solvent from the first crystallization solution to produce a first FDCA pathway product slurry, wherein the first FDCA pathway product slurry comprises a first plurality of FDCA pathway product crystals of different particle sizes and a second portion of the first crystallization solvent. The crystallization process can further include dissolving the first plurality of FDCA pathway product crystals in a second crystallization solvent to produce a second crystallization solution comprising the FDCA pathway product and the second crystallization solvent; removing a first portion of the second crystallization solvent from the second crystallization solution to produce a second FDCA pathway product slurry comprising a second plurality of FDCA pathway product crystals of different particle sizes and a second portion of the second crystallization solvent; and separating the second plurality of FDCA pathway product crystals from the second portion of the second crystallization solvent.

The process can include a crystallization process that comprises providing a first crystallization solution comprising the second FDCA pathway product and a first crystallization solvent selected from the group consisting of water, an organic solvent, and combinations thereof; and removing a first portion of the first crystallization solvent from the first solution to produce a first FDCA pathway product slurry, wherein the first FDCA pathway product slurry comprises a first plurality of second FDCA pathway product crystals of different particle sizes and a second portion of the first crystallization solvent; and optionally separating the first plurality of second FDCA pathway product crystals from the second portion of the first crystallization solvent. The crystallization process can further include dissolving the first plurality of second FDCA pathway product crystals in a second crystallization solvent to produce a second crystallization solution comprising the second FDCA pathway product and the second crystallization solvent; removing a first portion of the second crystallization solvent from the second crystallization solution to produce a second FDCA pathway product slurry comprising a second plurality of the second FDCA pathway product crystals of different particle sizes and a second portion of the second crystallization solvent; and separating the second plurality of the second FDCA pathway product crystals from the second portion of the second crystallization solvent.

The process can further comprise converting FDCA to an ester of FDCA by contacting the FDCA with an alcohol under conditions sufficient to produce a corresponding ester of FDCA. The alcohol can be an aliphatic alcohol, a diol, ethylene glycol, or an aromatic alcohol. The ester of FDCA can be a diester of FDCA. The alcohol can be methanol and the diester of FDCA can be the dimethyl ester of FDCA. The process can further comprise converting FDCA or an FDCA ester to an FDCA amide by contacting the FDCA or FDCA ester with an amino-substituted compound under conditions sufficient to produce a corresponding FDCA amide. The amino-substituted compound can be 1,6-hexamethylenediamine. The FDCA amide can be an FDCA diamide. The process can further comprise converting FDCA to an FDCA halide by contacting the FDCA with a hydrohalic acid having the formula HX, wherein X is a halide, under conditions sufficient to produce the corresponding FDCA halide. The halide can be chloride and the FDCA halide can be FDCA chloride. The FDCA chloride can be FDCA dichloride.

The process can further comprise polymerizing FDCA or derivative thereof under conditions sufficient to produce an FDCA-based polymer. The FDCA derivative can be selected from the group consisting of an FDCA diester, an FDCA dihalide, and an FDCA diamide. The FDCA diester can be dimethyl FDCA ester. The FDCA diester can be di(ethylene glycol) FDCA ester. The polymerizing step can be a polycondensation reaction. The process can comprise a transesterification reaction that precedes the polycondensation reaction. The polymerizing step can comprise contacting the FDCA derivative with a second monomer. The second monomer can be a polyol.

The process can further comprise:

(a°) prior to step (a), contacting a carbohydrate feedstock comprising a sugar and a dehydration solvent with a catalyst under conditions sufficient to form a reaction mixture for dehydrating the sugar to produce the furanic oxidation substrate, wherein the furanic oxidation substrate is present in a dehydration product solution that comprises the furanic oxidation substrate and the dehydration solvent.

The sugar can be fructose and the furanic oxidation substrate can be HMF. The oxidation feedstock of step (a) can comprise the dehydration product solution of step (a°). With respect to the (first) heterogeneous oxidation catalyst, (1) the noble metal can be platinum; (2) the solid support can be selected from the group consisting of silica and a carbonaceous material; and (3) the plurality of pores can be characterized by a mean pore diameter in the range of from or any number in between 10 nm to 100 nm. With respect to the (second) heterogeneous oxidation catalyst: (1) the noble metal can be platinum; (2) the solid support can be selected from the group consisting of silica and a carbonaceous material; and (3) the plurality of pores can be characterized by a mean pore diameter in the range of from or any number in between 10 nm to 100 nm.

In another aspect, the present disclosure is directed to a process for producing a crystalline FDCA pathway product composition, the method comprising:

providing a crystallization solution comprising an FDCA pathway product and a crystallization solvent that is a multi-component solvent comprising water and a water-miscible organic solvent;

initiating crystallization of the FDCA pathway product; and producing a plurality of FDCA pathway product crystals of different particle sizes. In certain embodiments, the water-miscible organic solvent is a water-miscible aprotic organic solvent.

The water-miscible organic solvent can be a water-miscible aprotic organic solvent. The water-miscible aprotic organic solvent can be selected from the group consisting of tetrahydrofuran, a glyme, dioxane, a dioxolane, dimethylformamide, dimethylsulfoxide, sulfolane, acetone, N-methyl-2-pyrrolidone ("NMP"), methyl ethyl ketone ("MEK"), and gamma-valerolactone. The water-miscible organic solvent can be selected from the group consisting of a light water-miscible organic solvent and a heavy water-miscible organic solvent.

The multi-component solvent can comprise the water and the water-miscible organic solvent in a ratio of from or any number in between 1:6 to 6:1 v/v. The multi-component solvent can comprise the water and the water-miscible organic solvent in a ratio within a range defined by 1:6 to 6:1 v/v. The multi-component solvent can comprise at least 10 vol % water-miscible organic solvent.

The crystallization can be initiated by cooling the crystallization solution to a temperature below 60° C. The crystallization can be initiated by cooling the crystallization solution to a temperature below 50° C. The crystallization can be initiated by removing a portion of the crystallization solvent to produce a first FDCA pathway product slurry, wherein the first FDCA pathway product slurry comprises a first plurality of FDCA pathway product crystals and a second portion of crystallization solvent or component thereof. The seed crystals can be added to the crystallization solution.

The plurality of FDCA pathway product crystals can be characterized by a median (D50) particle size in the range of from or any number in between 50 μm to 5000 μm or in the range of from or any number in between 50 μm to 2000 μm. The plurality of FDCA pathway product crystals can be characterized by a median (D50) particle size in the range of from or any number in between 150 μm to 750 μm.

The process for producing a crystalline FDCA pathway product composition can further comprise dissolving the first plurality of FDCA pathway product crystals in a second crystallization solvent to produce a second crystallization solution comprising a second plurality of FDCA pathway product crystals and a second crystallization solvent; removing a first portion of the second crystallization solvent from the second crystallization solution to produce a second FDCA pathway product slurry that comprises a second plurality of FDCA crystals and a second portion of the second crystallization solvent; and separating the second plurality of FDCA pathway product crystals from the second portion of the second crystallization solvent. Seed crystals can be added to the second crystallization solution. The dissolving step can be carried out at a temperature in the range of from or any number in between 80° C. to 220° C., or in the range of from or any number in between 60° C. to 180° C., or in the range of from or any number in between 80° C. to 150° C. In a still further aspect, the present disclosure is directed to a crystalline FDCA composition wherein the composition comprises a plurality of FDCA crystal particles of different particles sizes, wherein the plurality is characterized by a median particle size (D50) in the range of from 50 μm to 5000 μm, such as 50, 75, 100, 200, 300, 400, 500, 600, 700, 800, 900, 1000, 1500, 2000, 2500, 3000, 3500, 4000, 4500, or 5000 μm or within a range defined by any two of the aforementioned sizes.

In another aspect, the present disclosure is directed to a process for converting FDCA to an FDCA derivative selected from the group consisting of an FDCA salt, an FDCA ester, an FDCA amide, and an FDCA halide.

In a still further aspect, the present disclosure is directed to process for producing an FDCA-based polymer selected from the group consisting of an FDCA-based polyester and an FDCA-based polyamide.

In some embodiments, the present disclosure is directed to a composition comprising: (a) an oxidation feedstock comprising a furanic oxidation substrate and an oxidation solvent; (b) oxygen; (c) a heterogeneous oxidation catalyst; (d) an FDCA pathway product; wherein the oxidation solvent is a solvent selected from the group consisting of an organic solvent and a multi-component solvent; wherein the heterogeneous oxidation catalyst comprises a solid support and a noble metal; wherein the heterogeneous oxidation catalyst comprises a plurality of pores and a specific surface area in the range of from or any number in between 20 $m^2/g$ to 500 $m^2/g$; and wherein the composition is substantially free of added base.

The noble metal can be selected from the group consisting of platinum, gold, and a combination thereof. The oxidation solvent can be a multi-component solvent comprising water and a water-miscible organic solvent. The water-miscible organic solvent can be a water-miscible aprotic organic solvent. The water-miscible aprotic organic solvent can be selected from the group consisting of tetrahydrofuran, a glyme, dioxane, a dioxolane, dimethylformamide, dimethylsulfoxide, sulfolane, acetone, N-methyl-2-pyrrolidone ("NMP"), methyl ethyl ketone ("MEK"), and gamma-valerolactone. The water-miscible organic solvent can be selected from the group consisting of a light water-miscible organic solvent and a heavy water-miscible organic solvent.

The water and the water-miscible organic solvent can be present in a ratio of from or any number in between 1:6 to 6:1 v/v water:water-miscible organic solvent. The water and the water-miscible organic solvent can be present in a ratio within a range defined by 1:6 to 6:1 v/v water:water-miscible organic solvent. The water and the water-miscible organic solvent can be present in a ratio of 1:1 v/v water:water-miscible organic solvent. The water-miscible organic solvent can comprise at least 10 vol % of the multi-component solvent.

The furanic oxidation substrate can be 5-(hydroxymethyl) furfural (HMF). The furanic oxidation substrate can be selected from the group consisting of diformylfuran (DFF), hydroxymethylfurancarboxylic acid (HMFCA), and formylfurancarboxylic acid (FFCA).

The oxidation feedstock can comprise the furanic oxidation substrate at a concentration of at least 5% by weight. The furanic oxidation substrate can be present in the oxidation feedstock at a concentration of at least 10% by weight.

The heterogeneous oxidation catalyst can comprise the metal at a loading in the range of from or any number in between 0.3% to 5% by weight of the heterogeneous oxidation catalyst. The heterogeneous oxidation catalyst can further comprise a promoter.

The solid support can comprise a material selected from the group consisting of a metal oxide, a carbonaceous material, a polymer, a metal silicate, a metal carbide, and any combination of two or more thereof. The metal oxide can be selected from the group consisting of silica, zirconia, and alumina. The carbonaceous material can be carbon black. The solid support can be a composite material comprising a binder and a material selected from the group consisting of a metal oxide, a carbonaceous material, a polymer, a metal silicate, and a metal carbide.

The heterogeneous oxidation catalyst can comprise a specific surface area in the range of from or any number in between 25 $m^2/g$ to 350 $m^2/g$, from or any number in between 25 $m^2/g$ to 250 $m^2/g$, from or any number in between 25 $m^2/g$ to 225 $m^2/g$, from or any number in between 25 $m^2/g$ to 200 $m^2/g$, from or any number in between 25 $m^2/g$ to 175 $m^2/g$, from or any number in between 25 $m^2/g$ to 150 $m^2/g$, from or any number in between 25 $m^2/g$ to 125 $m^2/g$, or from or any number in between 25 $m^2/g$ to 100 $m^2/g$. The heterogeneous oxidation catalyst can comprise a pore volume wherein at least 50% of the pore volume is from pores having a pore diameter in the range of from or any number in between 5 nm to 100 nm. The heterogeneous oxidation catalyst can comprise a pore volume wherein no more than 10% of the pore volume of the heterogeneous oxidation catalyst is from pores having a pore diameter less than 10 nm. The heterogeneous oxidation catalyst can comprise a pore volume wherein no more than 10% of the pore volume of the heterogeneous oxidation catalyst is from pores having a pore diameter ranging from or any number in between 0.1 nm to 10 nm. The pore volume of the heterogeneous oxidation catalyst can be no more than 2.5% of the pores having a pore diameter less than 10 nm but not zero. The pore volume of the heterogeneous oxidation catalyst can be no more than 2.5% of the pores having a pore diameter ranging from or any number in between 0.1 nm to 10 nm. The plurality of pores can be characterized by a mean pore diameter in the range of from or any number in between 10 nm to 100 nm. The heterogeneous oxidation catalyst can comprise a specific pore volume that is in the range of from or any number in between 0.1 $cm^3/g$ to 1.5 $cm^3/g$.

The heterogeneous oxidation catalyst can comprise a second plurality of pores, wherein at least one of the first or second pluralities of pores is characterized by a mean pore diameter in the range of from or any number in between 10 nm to 100 nm. Each of the first and second plurality of pores can be characterized by a mean pore diameter in the range of from or any number in between 10 nm to 100 nm.

The oxygen can be present at a molar ratio of oxygen: furanic oxidation substrate in the range of from or any number in between 2:1 to 10:1. The molar ratio of oxygen: furanic oxidation substrate can be in the range of from or any number in between 2:1 to 5:1. The oxygen can be present at a pressure ($p_{O2}$) in the range of from or any number in between 50 psig to 1000 psig. The oxygen can be present at a pressure ($p_{O2}$) in the range of from or any number in between 50 psig to 200 psig.

In some embodiments, the present disclosure is directed to an apparatus comprising: (a) an oxidation reaction zone; (b) an oxygen feed stream comprising oxygen; (c) an oxidation feedstock stream comprising a furanic oxidation substrate and an oxidation solvent; wherein the oxidation solvent is a solvent selected from the group consisting of an organic solvent and a multi-component solvent; (d) a pathway product stream comprising an FDCA pathway product; wherein the oxygen feed stream and oxidation feedstock stream are passed into the oxidation reaction zone and react to produce an FDCA pathway product; wherein the oxidation reaction zone contains a heterogeneous oxidation catalyst, oxygen, a furanic oxidation substrate, and an oxidation solvent; wherein the FDCA pathway product stream exits the oxidation reaction zone; wherein the heterogeneous oxidation catalyst comprises a solid support and a noble metal; wherein the heterogeneous oxidation catalyst comprises a plurality of pores and a specific surface area in the range of from or any number in between 20 $m^2/g$ to 500 $m^2/g$; wherein the oxidation reaction zone is substantially free of added base.

The apparatus can further comprise a recycle stream wherein the recycle stream comprises unreacted furanic oxidation substrate; wherein the recycle stream exits the oxidation reaction zone; and wherein the apparatus contains a means for optionally passing the recycle stream back into the oxidation reaction zone.

The apparatus can further comprise (e) a second oxidation reaction zone; (f) a second oxygen feed stream comprising oxygen; (g) a second pathway product stream comprising an FDCA pathway product; wherein the pathway product stream from element (d) and the second oxygen feed stream are passed into the second oxidation reaction zone and react to produce an FDCA pathway product; wherein the second pathway product stream exits the second oxidation reaction zone; wherein the second oxidation reaction zone contains a second heterogeneous oxidation catalyst, oxygen, and the pathway product stream from element (d); wherein the second heterogeneous oxidation catalyst comprises a solid support and a noble metal; wherein the second heterogeneous oxidation catalyst comprises a plurality of pores and a specific surface area in the range of from or any number in between 20 $m^2/g$ to 500 $m^2/g$; wherein the second oxidation reaction zone is substantially free of added base. The apparatus can further comprise a recycle stream wherein the recycle stream comprises unreacted pathway product stream from element (d); wherein the recycle stream exits the second oxidation reaction zone; and wherein the apparatus contains a means for optionally passing the recycle stream into the oxidation reaction zone from element (a).

In some embodiments, the present disclosure is directed to a process for producing a furanic oxidation substrate, the process comprising contacting a carbohydrate feedstock comprising a sugar and a dehydration solvent with an acid catalyst under conditions sufficient to form a dehydration reaction mixture for dehydrating the sugar to produce a furanic oxidation substrate, wherein the acid catalyst is an acid selected from the group consisting of HBr, $H_2SO_4$, HNO$_3$, HCl, HI, H$_3$PO$_4$, triflic acid, methansulfonic acid, benzenesulfonic acid, and p-toluene sulfonic acid, wherein when the acid catalyst is not HBr, the dehydration reaction mixture further comprises a bromide salt, and wherein the dehydration solvent comprises N-methyl-pyrrolidone (NMP).

The acid catalyst can be HBr. The acid catalyst can be selected from the group consisting of H$_2$SO$_4$, HNO$_3$, HCl, HI, H$_3$PO$_4$, triflic acid, methansulfonic acid, benzenesulfonic acid, and p-toluene sulfonic acid, and wherein the dehydration reaction mixture comprises a bromide salt. The bromide salt can be selected from the group consisting of LiBr, NaBr, KBr, MgBr$_2$, CaBr$_2$, ZnBr$_2$, tetramethylammonium bromide, tetraethylammonium bromide, tetrapropylammonium bromide, tetrabutylammonium bromide, and any combination of two or more thereof. The acid catalyst can further comprise a Lewis acid. The Lewis acid can be selected from the group consisting of a borontrihalide, an organoborane, an aluminum trihalide, a phosphorus pentafluoride, an antimony pentafluoride, a rare earth metal triflate, a metal halide, a metal trifluoroacetate, or a metal cation ether complex. The Lewis acid can be a metal halide. The metal halide can be ZnCl$_2$ or ZnBr$_2$.

The yield of furanic oxidation substrate can be at least 60%, or at least 70%, or at least 80%, or at least 90% or at least 95%, or at least 98% or at least 99%. The sugar can be fructose. The furanic oxidation substrate can be HMF.

The dehydration reaction mixture can be maintained at a temperature in the range of from or any number in between 80° C. and 160° C., or 80° C. and 150° C., or 80° C. and 140° C., or 80° C. and 130° C., or 80° C. and 120° C., or 80° C. and 110° C., or 80° C. and 100° C.

The dehydration solvent can further comprise water. The dehydration solvent can comprise water and NMP in a range from or any number in between 1-5 wt % water and 99-95% NMP, or 5-10 wt % water and 95-90 wt % NMP, or 10-15 wt % water and 90-85 wt % NMP, or 15-20 wt % water and 85-80 wt % NMP, or 20-25 wt % water and 80-75 wt % NMP, or 25-30 wt % water and 75-70 wt % NMP, or 30-35 wt % water and 70-65 wt % NMP, or 35-40 wt % water and 65-60 wt % NMP, or 40-45 wt % water and 60-55 wt % NMP, or 45-50 wt % water and 55-50 wt % NMP, or 50-55 wt % water and 50-45 wt % NMP, or 55-60 wt % water and 45-40 wt % NMP, or 60-65 wt % water and 40-35 wt % NMP, or 65-70 wt % water and 35-30 wt % NMP, or 70-75 wt % water and 30-25 wt % NMP, or 75-80 wt % water and 25-20 wt % NMP, or 80-85 wt % water and 20-15 wt % NMP, or 85-90 wt % water and 15-10 wt % NMP, or 90-95 wt % water and 10-5 wt % NMP, or 95-99 wt % water and 5-1 wt % NMP.

The dehydration solvent can further comprise a second organic solvent species. The second organic solvent species can be a water-miscible organic solvent that is not N-methyl-pyrrolidone (NMP). Each of the water-miscible aprotic organic solvent can be selected from the group consisting of tetrahydrofuran, a glyme, dioxane, a dioxolane, dimethylformamide, dimethylsulfoxide, sulfolane, acetone, methyl ethyl ketone ("MEK"), and gamma-valerolactone, The furanic oxidation substrate can be present in a dehydration product solution that comprises the furanic oxidation substrate and the dehydration solvent. The dehydration product solution further can comprise an unreacted sugar. The dehydration product solution can be a mixture that includes humins. The dehydration product solution or the mixture that includes humins can be subjected to one or more membranes to effect separation of the furanic oxidation substrate from one or more components selected from the group consisting of a humin, an unreacted sugar, or a combination thereof. The one or more membranes can be selected from the group consisting of an ultrafiltration, a nanofiltration membrane, and a combination thereof.

DETAILED DESCRIPTION

I. Processes for Producing FDCA Pathway Products

Figure 1:
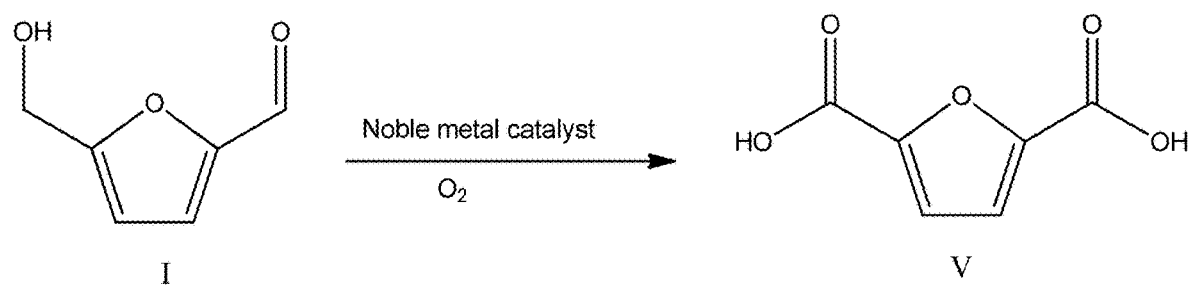
FIG. 1 depicts the net conversion of 5-(hydroxymethyl) furfural (HMF) (I) to 2,5-furandicarboxylic acid (FDCA) (V).
Figure 2:
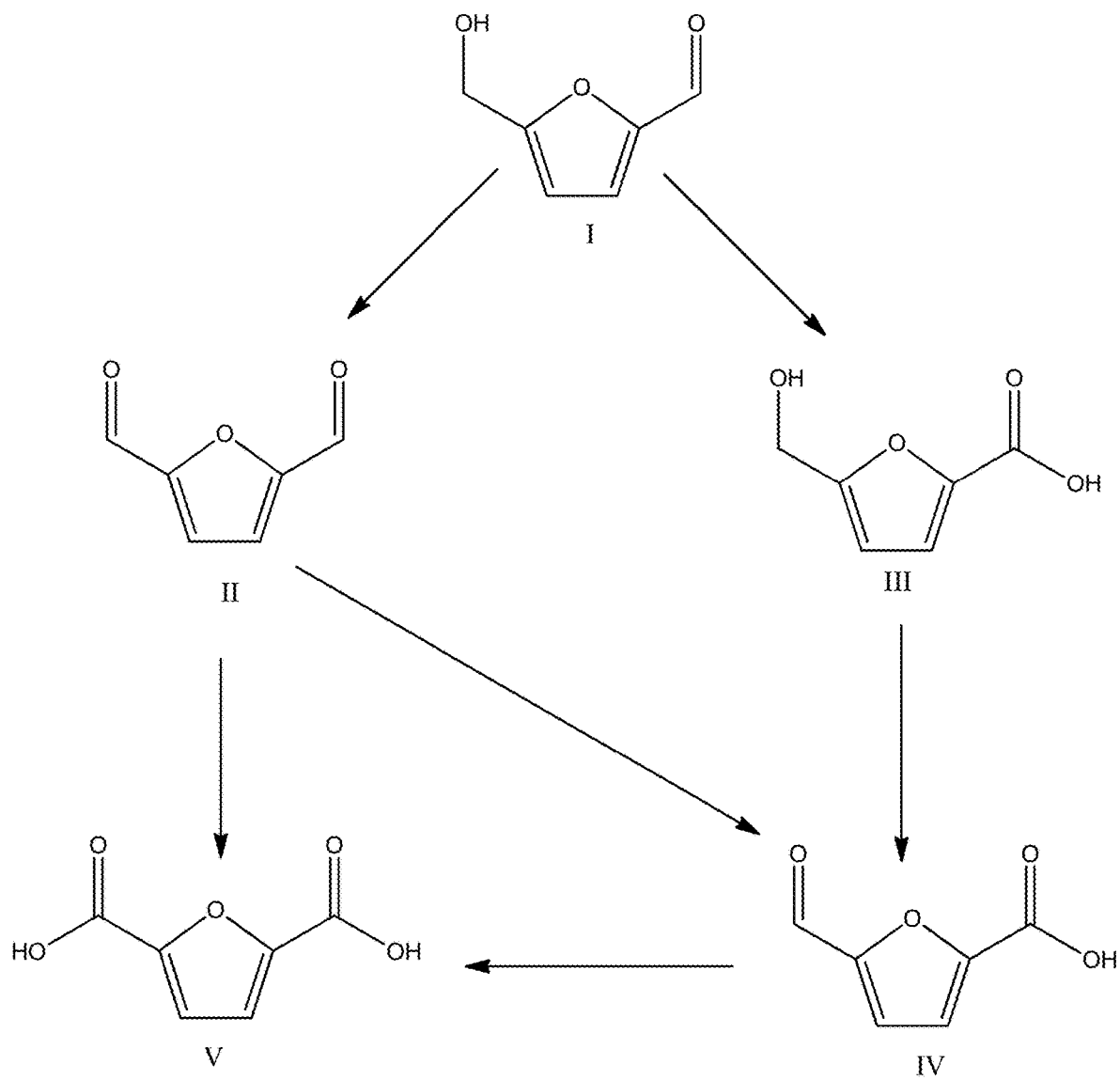
FIG. 2 depicts potential FDCA pathway intermediates that may be generated by the oxidation of HMF. These intermediates are diformylfuran (II), hydroxymethylfurancarboxylic acid (III), and formylfurancarboxylic acid (IV). The final oxidation product in the pathway is FDCA (V).

In one embodiment, the present disclosure provides novel processes for producing desired furandicarboxylic acid (FDCA) pathway products at high yields and high selectivities from the oxidation of a furanic oxidation substrate. Significantly, these results are achieved without the need for any added base. The base-free (and substantially base-free) oxidative processes of the present disclosure are attractive as compared to existing processes for producing FDCA and related pathway products because, inter alia, they do not require further downstream processing to remove added base, or any by-products generated as a result of the base addition. As used herein, the terms "furandicarboxylic acid pathway product" and "FDCA pathway product" are used interchangeably herein to refer to 2,5-furandicarboxylic acid (FDCA) or a 2,5-furandicarboxylic acid pathway intermediate compound. The net conversion of HMF to FDCA is shown in FIG. 1. The term "furandicarboxylic acid pathway" is used herein to refer to the pathway depicted in FIG. 2. As used herein, the terms "2,5-furandicarboxylic acid pathway intermediate compound" and "FDCA pathway intermediate compound" are used interchangeably to refer to any one of diformylfuran (DFF), hydroxymethylfurancarboxylic acid (HMFCA), and 5-formylfurancarboxylic acid (FFCA), which correspond to compounds II, III, and IV in FIG. 2, respectively.

More specifically, the present disclosure provides a process for producing an FDCA pathway product from a furanic oxidation substrate, the process comprising:

(a) contacting an oxidation feedstock comprising a furanic oxidation substrate and an oxidation solvent with oxygen in the presence of a heterogeneous oxidation catalyst under conditions sufficient to form a reaction mixture for oxidizing the furanic oxidation substrate to an FDCA pathway product, and producing the FDCA pathway product, wherein the oxidation solvent is a solvent selected from the group consisting of an organic solvent and a multi-component solvent, wherein the reaction mixture is substantially free of added base, and wherein the heterogeneous oxidation catalyst comprises a solid support and a noble metal, and wherein the heterogeneous oxidation catalyst comprises a plurality of pores and a specific surface area in the range of from or any number in between 20 $m^2/g$ to 500 $m^2/g$, such as e.g., 20, 30, 40, 50, 60, 70, 80, 90, 100, 120, 140, 160, 180, 200, 225, 250, 275, 300, 325, 350, 375, 400, 425, 450, 475, or 500 $m^2/g$ or is within a range defined by any two of the aforementioned surface areas.

The term "substantially free of added base" is used herein to refer to the lack of any base added to the reaction mixture (i.e., no added base), or the addition of a de minimis quantity of base. The term "de minimis quantity of base" refers herein to an amount of base which, when added to a reaction mixture employed in the practice of the present disclosure, does not alter the oxidation reaction by more than 1% with respect to product yield or product selectivity, as compared to the same oxidation reaction performed under the same conditions with the exception that no base is added to the reaction mixture. Typically, the processes of the present disclosure are carried out under base-free conditions, i.e., no base is added to the reaction mixture during the contacting (i.e., oxidation) step.

Oxidation processes of the present disclosure result in the production of the desired FDCA pathway product at a yield that is typically at least 80% and a selectivity that is typically at least 90% (both on a molar basis). In some embodiments, the yield is at least 85%, and in other embodiments, it is at least 90%, at least 95%, and often, at least 98% or at least 99%. In some embodiments, the yield ranges from between 85-90%, 87-92%, 90-95%, 92-97%, 95-98%, or 97-99%, or is within a range defined by any two of the aforementioned percentages. The selectivity with respect to production of the desired FDCA pathway product is more typically at least 91% or at least 92% or at least 93% or at least 94% or at least 95% or at least 96% or at least 97% or at least 98% or at least 99%. In some embodiments, the selectivity with respect to the desired FDCA pathway product ranges from between 91-93%, 92-94%, 93-95%, 94-96%, 95-97%, 96-98%, 97-99%, or is within a range defined by any two of the aforementioned percentages. The desired FDCA pathway product is usually FDCA.

The term "oxidation feedstock" refers herein to a source material for the furanic oxidation substrate. As used herein, the term "furanic oxidation substrate" refers to a compound that is HMF or an FDCA intermediate compound (i.e., DFF, HMFCA, FFCA, or combination thereof) or a combination thereof. Oxidation feedstocks employed in the practice of the processes described herein may be employed in any of a variety of forms, including, for example, a solution, a suspension, a dispersion, an emulsion, and the like. Typically, the oxidation feedstock comprises the furanic oxidation substrate in solution with the oxidation solvent.

In the oxidation processes described herein, the FDCA pathway product is typically FDCA. In certain embodiments, the furanic oxidation substrate is typically HMF. However, it may be desirable to use a furanic oxidation substrate that is an FDCA pathway intermediate compound or mixture of FDCA pathway intermediate compounds, i.e., DFF, HMFCA, FFCA, or a mixture of any two or more thereof. This may be an attractive option in situations where HMF has been previously oxidized to an FDCA pathway intermediate compound or mixture of intermediate compounds, and the intermediate compound(s) is (are) available for use as a raw material. When such intermediates are used as furanic oxidation substrates in the oxidative processes of the present disclosure, the resulting FDCA pathway product is typically FDCA, but it may also be a different FDCA pathway intermediate compound that is "downstream" (from an oxidation standpoint) in the FDCA pathway, of the FDCA pathway intermediate employed as the furanic oxidation substrate.

The oxidation feedstock may contain other agents or residual components that are soluble or insoluble in the oxidation feedstock. For example, the oxidation feedstock may be a crude oxidation feedstock of HMF, or other furanic oxidation substrate, and the oxidation solvent. The term "crude feedstock" refers herein to a feedstock that, in addition to comprising the desired furanic oxidation substrate, also comprises impurities and/or by-products related to the production, isolation, and/or purification of the desired furanic oxidation substrate. For example, the oxidation feedstock, may, in addition, comprise certain biomass-related components that originate from biomass or are by-products which are generated in the conversion of biomass to a sugar (by, for example, thermal, chemical, mechanical, and/or enzymatic degradative means), where such sugar is subsequently converted to HMF. Thus, the oxidation feedstock may also comprise a component selected from the group consisting of a polysaccharide (including, for example, a cellulose (e.g., a lignocellulose, a hemicellulose, and the like), starch, and the like), an oligosaccharide (e.g., a raffinose, a maltodextrin, a cellodextrin, and the like), a monosaccharide (e.g., glucose, fructose, galactose, mannose, xylose, rabbinose, and the like), a disaccharide (e.g., sucrose, lactose, maltose, cellobiose and the like), furanic substrates such as furfural, oligomeric or polymeric humin by-products (humins) and residual mineral acids. Similarly, the oxidation feedstock may be a crude feedstock of HMF oxidation products comprising HMF and/or FDCA pathway intermediate compounds.

In addition to the high yields and high selectivities observed, oxidation processes of the present disclosure produce FDCA pathway products, such as, for example, FDCA at relatively high concentrations in a resulting product solution. The high productivity levels obtained from the processes described herein are believed to be due to the combined use of the novel heterogeneous oxidation catalysts employed and the properties of the oxidation solvent.

As used herein, the term, "oxidation solvent" refers to a solvent that is an organic solvent or a multi-component solvent in which the furanic oxidation substrate and the desired FDCA pathway product are each separately soluble at a minimum level of at least 2% by weight at the temperature at which the contacting (oxidation) step is conducted. Typically, the oxidation solvent is one in which the FDCA pathway product has a solubility of at least 3 wt %, at least 4 wt %, and more typically, at least 5 wt %, at least 6 wt %, at least 7 wt %, at least 8 wt %, at least 9 wt %, at least 10 wt %, at least 11 wt %, at least 12 wt %, at least 13 wt %, at least 14 wt %, or at least 15 wt %, as measured at the temperature at which the contacting step is carried out. In some embodiments, the FDCA pathway product has a solubility that ranges from between 2-4 wt %, 3-5 wt %, 4-6 wt %, 5-7 wt %, 6-8 wt %, 7-9 wt %, 8-10 wt %, 9-11 wt %, 10-12 wt %, 11-13 wt %, 12-14 wt %, or 13-15% or is within a range defined by any of two of the aforementioned weight percentages. The solubility of the FDCA pathway product in a candidate organic solvent or candidate multi-component solvent can be readily determined using known methods, as well as the method described in Example 1.

Without wishing to be bound by theory, the oxidation solvents employed in the present disclosure are believed to facilitate the efficient conversion of furanic oxidation substrate to FDCA pathway product (catalyzed by the high performing catalysts of the present disclosure) by, among other things, eliminating product precipitation that may lead to reactor/catalyst fouling. Moreover, the relatively high concentrations of FDCA and FDCA intermediate compounds that may be achieved in the processes of the present disclosure results in high process productivity and less costly solvent removal, in contrast to processes that employ poor solvents such as, for example water or the acetic acid-water mixtures described in U.S. Pat. No. 7,700,788. Thus, the present disclosure provides processes that are particularly attractive for the commercial scale production of FDCA, and related intermediates.

When carrying out the oxidation processes of the present disclosure, the furanic oxidation substrate may be present in the oxidation feedstock at any concentration up to its solubility limit, in circumstances where the feedstock is a solution. In some embodiments, the concentration of furanic oxidation substrate in the oxidation feedstock is at least 1 wt %, at least 2 wt %, at least 3 wt %, at least 4 wt %, at least 5 wt %, at least 6 wt %, at least 7 wt %, at least 8 wt %, at least 9 wt %, at least 10 wt %, at least 11 wt %, at least 12 wt %, at least 13 wt %, at least 14 wt %, or at least 15 wt % by weight of the oxidation feedstock. In some embodiments, the concentration of furanic oxidation substrate in the oxidation feedstock ranges from 1-3 wt %, 2-4 wt %, 3-5 wt %, 4-6 wt %, 5-7 wt %, 6-8 wt %, 7-9 wt %, 8-10 wt %, 9-11 wt %, 10-12 wt %, 11-13 wt %, 12-14 wt %, or 13-15% or is within a range defined by any of two of the aforementioned weight percentages. Typically, the furanic oxidation substrate is present in the oxidation feedstock at a concentration of at least 5 wt %. More typically, the furanic oxidation substrate is present in the oxidation feedstock at a concentration of at least 6 wt %, or at least 7 wt %, or at least 8 wt %, or at least 9 wt %, or at least 10 wt %, or at least 11 wt %, or at least 12 wt %, or at least 13 wt %, or at least 14 wt %, or at least 15 wt % at the temperature at which the contacting (oxidation) step is conducted. In some embodiments, the furanic oxidation substrate is present in the oxidation feedstock at the temperature at which the contacting (oxidation) step is conducted in a concentration that ranges from between 6-8 wt %, 7-9 wt %, 8-10 wt %, 9-11 wt %, 10-12 wt %, 11-13 wt %, 12-14 wt %, or 13-15% or is within a range defined by any of two of the aforementioned weight percentages.

Organic solvents that exhibit the requisite minimal solvating requirements for the furanic oxidation substrate and FDCA are suitable for use in the practice of the present disclosure, either alone or as a component of a multi-component solvent. Applicants have discovered, in particular, that the use of aprotic organic solvents, in combination with the catalysts and conditions described herein, appear to facilitate the high productivities observed with respect to the processes of the present disclosure. Therefore, in some embodiments, the oxidation solvent comprises an aprotic organic solvent (e.g., an ether, an ester, a ketone, and the like) either alone (i.e., as a single-component solvent) or as a component of a multi-component solvent. When used in a multi-component solvent, the aprotic organic solvent is typically miscible with the other component(s) of the multi-component solvent. The term "multi-component solvent" refers herein to a mixture of two, three, or more solvent species. Multi-component solvents employed in the practice of the present disclosure may comprise two or more solvent species selected from the group consisting of a first organic solvent species, a second organic solvent species, and water. When the multi-component solvent comprises water and an organic solvent, the organic solvent is a water-miscible organic solvent. Typically, the water-miscible organic solvent is a water-miscible aprotic organic solvent.

With respect to the processes of the present disclosure, it should be noted that candidate component solvents for the multi-component solvent should not be limited to solvents in which the furanic oxidation substrate and desired FDCA pathway product are highly soluble. Applicants have discovered that multi-component solvents may exhibit a synergistic solvating effect with respect to FDCA, even when FDCA is poorly soluble in each component solvent. For example, FDCA has poor solubility in water. Applicants have discovered that, even when paired with a water-miscible organic solvent having poor FDCA-solvating capabilities, the combination of water and the water-miscible organic solvent exhibits enhanced FDCA-solvating capability.

Illustrative multi-component solvents that exhibit this effect include those that comprise water and a water-miscible aprotic organic solvent. Exemplary water-miscible aprotic solvents suitable for use in the practice of the present disclosure include tetrahydrofuran, a glyme, dioxane, a dioxolane, dimethylformamide, dimethylsulfoxide, sulfolane, acetone, N-methyl-2-pyrrolidone ("NMP"), methyl ethyl ketone ("MEK"), gamma-valerolactone, and the like. Preferably, the water-miscible aprotic organic solvent is an ether, such as, for example, a glyme, dioxane (1,4-dioxane), a dioxolane (e.g., 1,3-dioxolane), tetrahydrofuran, and the like. Glymes that are suitable for use in the practice of the present disclosure include, for example, monoglyme (1,2-dimethoxyethane, "DME"), ethyl glyme, diglyme (diethylene glycol dimethyl ether), ethyl diglyme, triglyme, butyl diglyme, tetraglyme, a polyglyme, a highly ethoxylated diether of a high molecular weight alcohol ("higlyme"), and the like. Often, the oxidation solvent is a multi-component solvent comprising water and a water-miscible aprotic organic solvent that is glyme, diglyme, or dioxane.

In some embodiments, the multi-component solvent comprises water and dioxane. In some embodiments, the multi-component solvent comprises water and DME. In some embodiments, the multi-component solvent comprises water and diglyme. In some embodiments, the multi-component solvent comprises water and triglyme. In some embodiments, the multi-component solvent comprises water and tetraglyme. In some embodiments, the multi-component solvent comprises water and higlyme. In some embodiments, the multi-component solvent comprises water and NMP. In some embodiments, the multi-component solvent comprises water and MEK. In some embodiments, the multi-component solvent comprises water and gamma-valerolactone.

Example 1 describes a solubility study that examined the solubility of FDCA in: (1) diglyme only; (2) dioxane only; (3) water only; (4) a multi-component solvent made up of 4:1 (v/v) dioxane:H$_2$O; and (5) a multi-component solvent made up of 1:1 (v/v) glyme:H$_2$O. The results are depicted in a plot of FDCA solubility as a function of temperature in FIG. 3. Although FDCA exhibits relatively low solubilities in water (less than 2% by weight at temperatures in the range of from 22° C. to 140° C.), dioxane (less than 2% by weight at temperatures in the range of from 22° C. to 100° C.), and diglyme (less than 2% by weight at temperatures in the range of from 22° C. to 100° C.), it surprisingly exhibits high solubilities in multi-component solvents of, for example, 4:1 dioxane:H$_2$O (v:v) (from 4% by weight to 11% by weight at temperatures in the range of from 22° C. to 140° C.) and 1:1 diglyme:water (v:v) (from just below 2% by weight to 9% by weight at temperatures in the range of from 22° C. to 140° C.). These multi-component solvents are desirable because they facilitate the production of greater quantities of FDCA pathway product with relatively less solvent (for example, as compared to water only as a solvent) that would typically need to be removed during product recovery operations. Organic solvents and additional multi-component solvents suitable for use as an oxidation solvent in the practice of the present disclosure can be readily identified using the assay method described in Example 1.

In some embodiments, the composition of the oxidation solvent may take into consideration the requirements of further downstream processes (e.g., to facilitate product recovery, purification, and the like), or upstream processes (e.g., the conversion of a sugar to the furanic oxidation substrate). For example, in certain embodiments it may be desirable to employ an oxidation solvent that is a multi-component solvent comprising a light solvent and a heavy solvent. The term "light solvent" refers to a solvent having a boiling point at a certain pressure that occurs at a temperature that is less than the boiling point (temperature) of the heavy solvent at the same pressure. Conversely, the term "heavy solvent" refers to a solvent having a boiling point at a certain pressure that occurs at a temperature that is higher than the boiling point (temperature) of the light solvent at the same pressure. When the multi-component solvent comprises water and a water-miscible organic solvent, the water-miscible organic solvent may be a light water-miscible organic solvent (i.e., a water-miscible organic solvent having a boiling point that occurs at a temperature less than the boiling point of water) or it may be a heavy water-miscible organic solvent (i.e., a water-miscible organic solvent having a boiling point that occurs at a temperature higher than the boiling point of water). Typically, the light and heavy water-miscible organic solvent are a light and heavy aprotic organic solvent, respectively. Exemplary light water-miscible (and aprotic) organic solvents employed with water in a multi-component solvent include, for example, glyme, a dioxolane (e.g., 1,3-dioxolane), and tetrahydrofuran, and the like. Exemplary heavy water-miscible (and aprotic) organic solvents employed with water in a multi-component solvent include, for example, dioxane, ethyl glyme, diglyme (diethylene glycol dimethyl ether), ethyl diglyme, triglyme, butyl diglyme, tetraglyme, a polyglyme, and the like. In some embodiments (e.g., continuous reactor systems), all or a portion of the oxidation solvent or component thereof may be removed from the production solution (e.g., via distillation) and recycled to the reaction mixture. It such embodiments, it may be desirable to employ a multi-component solvent having a composition that corresponds to an azeotrope or which is capable of forming an azeotrope (i.e., an "azeotropic composition") at a temperature employed during the oxidation step (i.e., contacting step), or at a temperature employed during a process that is upstream or downstream of the oxidation step. Use of such multi-component solvents having an azeotropic composition may facilitate the recycling of the oxidation solvent (as part of the azeotropic composition) to the oxidation step, or to processes that occur upstream and/or downstream of the oxidation step.

In some embodiments, the water-miscible organic solvent species is at least 5 volume % (vol %), at least 10 vol %, at least 15 vol %, at least 20 vol %, at least 25 vol %, at least 30 vol %, at least 35 vol %, at least 40 vol %, at least 45 vol %, at least 50 vol %, at least 55 vol %, at least 60 vol %, at least 65 vol %, at least 70 vol %, at least 75 vol %, at least 80 vol %, at least 85 vol %, at least 90 vol %, or at least 95 vol % of the multi-component solvent; and correspondingly, water is typically less than 95 vol %, less than 90 vol %, less than 85 vol %, less than 80 vol %, less than 75 vol %, less than 70 vol %, less than 65 vol %, less than 60 vol %, less than 55 vol %, less than 50 vol %, less than 45 vol %, less than 40 vol %, less than 35 vol %, less than 30 vol %, less than 25 vol %, less than 20 vol %, less than 15 vol %, less than 10 vol %, or less than 5 vol %, respectively, of the multi-component system.

In some embodiments, the multi-component solvent comprises water in a range from or any number in between 1-5 wt % and a water-miscible organic solvent in a range from or any number in between 99-95 wt %. In some embodiments, the multi-component solvent comprises water in a range from or any number in between 5-10 wt % and a water-miscible organic solvent in a range from or any number in between 95-90 wt %. In some embodiments, the multi-component solvent comprises water in a range from or any number in between 10-15 wt % and a water-miscible organic solvent in a range from or any number in between 90-85 wt %. In some embodiments, the multi-component solvent comprises water in a range from or any number in between 15-20 wt % and a water-miscible organic solvent in a range from or any number in between 85-80 wt %. In some embodiments, the multi-component solvent comprises water in a range from or any number in between 20-25 wt % and a water-miscible organic solvent in a range from or any number in between 80-75 wt %. In some embodiments, the multi-component solvent comprises water in a range from or any number in between 25-30 wt % and a water-miscible organic solvent in a range from or any number in between 75-70 wt %. In some embodiments, the multi-component solvent comprises water in a range from or any number in between 30-35 wt % and a water-miscible organic solvent in a range from or any number in between 70-65 wt %. In some embodiments, the multi-component solvent comprises water in a range from or any number in between 35-40 wt % and a water-miscible organic solvent in a range from or any number in between 65-60 wt %. In some embodiments, the multi-component solvent comprises water in a range from or any number in between 40-45 wt % and a water-miscible organic solvent in a range from or any number in between 60-55 wt %. In some embodiments, the multi-component solvent comprises water in a range from or any number in between 45-50 wt % and a water-miscible organic solvent in a range from or any number in between 65-50 wt %. In some embodiments, the multi-component solvent comprises water in a range from or any number in between 50-55 wt % and a water-miscible organic solvent in a range from or any number in between 50-45 wt %. In some embodiments, the multi-component solvent comprises water in a range from or any number in between 55-60 wt % and a water-miscible organic solvent in a range from or any number in between 45-40 wt %. In some embodiments, the multi-component solvent comprises water in a range from or any number in between 60-65 wt % and a water-miscible organic solvent in a range from or any number in between 40-35 wt %. In some embodiments, the multi-component solvent comprises water in a range from or any number in between 65-70 wt % and a water-miscible organic solvent in a range from or any number in between 35-30 wt %. In some embodiments, the multi-component solvent comprises water in a range from or any number in between 70-75 wt % and a water-miscible organic solvent in a range from or any number in between 30-25 wt %. In some embodiments, the multi-component solvent comprises water in a range from or any number in between 75-80 wt % and a water-miscible organic solvent in a range from or any number in between 25-20 wt %. In some embodiments, the multi-component solvent comprises water in a range from or any number in between 80-85 wt % and a water-miscible organic solvent in a range from or any number in between 20-15 wt %. In some embodiments, the multi-component solvent comprises water in a range from or any number in between 85-90 wt % and a water-miscible organic solvent in a range from or any number in between 15-10 wt %. In some embodiments, the multi-component solvent comprises water in a range from or any number in between 90-95 wt % and a water-miscible organic solvent in a range from or any number in between 10-5 wt %. In some embodiments, the multi-component solvent comprises water in a range from or any number in between 95-99 wt % and a water-miscible organic solvent in a range from or any number in between 5-1 wt %.

In some embodiments, the volume ratio of water to water-miscible organic solvent is in the range from or any number in between 1:6 to 6:1. In certain embodiments, the volume ratio is from or any number in between 1:4 to 4:1 water:water-miscible organic solvent. In other embodiments, the volume ratio is from or any number in between 1:4 to 3:1 water:water miscible organic solvent. In other embodiments, the volume ratio is from or any number in between 1:3 to 3:1 water:water miscible organic solvent. In certain embodiments, the volume ratio is 1:1 water:water-miscible organic solvent.

In some embodiments, the multi-component solvent comprises water and two different water-miscible organic solvents. Typically both of the water-miscible organic solvents are water-miscible aprotic organic solvents. Each of the two water-miscible aprotic solvents can be independently selected from the group of tetrahydrofuran, a glyme, a dioxane, a dioxolane, dimethylformamide, dimethylsulfoxide, sulfolane, acetone, N-methyl-2-pyrrolidone ("NMP"), methyl ethyl ketone ("MEK"), and gamma-valerolactone. One or both of the water-miscible aprotic organic solvent can be an ether, such as, for example, a glyme, dioxane (for example 1,4-dioxane), dioxolane (e.g., 1,3-dioxolane), tetrahydrofuran, and the like. Glymes include, for example, monoglyme (1,2-dimethoxyethane, "DME"), ethyl glyme, diglyme (diethylene glycol dimethyl ether), ethyl diglyme, triglyme, butyl diglyme, tetraglyme, a polyglyme, a highly ethoxylated diether of a high molecular weight alcohol ("higlyme"), and the like.

In some embodiments, the volume ratio of water to the first and second water-miscible organic solvent is approximately 1:1:1 (v:v:v). In some embodiments, the volume ratio of water to the first and second water-miscible organic solvent is approximately 1:2:1 (v:v:v). In some embodiments, the volume ratio of water to the first and second water-miscible organic solvent is approximately 1:2:2 (v:v:v). In some embodiments, the volume ratio of water to the first and second water-miscible organic solvent is approximately 2:1:1 (v:v:v).

In some embodiments, the multi-component solvent comprises water and two different water-miscible organic solvents with the relative amounts of water to the first and second water-miscible organic solvents as shown in Table A.

TABLE A

| Weight percent of water in multi-component solvent system | Weight percent of first water-miscible organic solvent in multi-component solvent system | Weight percent of second water-miscible organic solvent in multi-component solvent system |
|---|---|---|
| 1-5% | 90-98% | 1-5% |
| 1-5% | 85-94% | 5-10% |
| 1-5% | 80-89% | 10-15% |
| 1-5% | 75-84% | 15-20% |
| 1-5% | 70-79% | 20-25% |
| 1-5% | 65-74% | 25-30% |
| 1-5% | 60-69% | 30-35% |
| 1-5% | 55-64% | 35-40% |
| 1-5% | 50-59% | 40-45% |
| 1-5% | 45-54% | 45-50% |
| 1-5% | 40-49% | 50-55% |
| 1-5% | 35-44% | 55-60% |
| 1-5% | 30-39% | 60-65% |
| 1-5% | 25-34% | 65-70% |
| 1-5% | 20-29% | 70-75% |
| 1-5% | 15-24% | 75-80% |
| 1-5% | 10-19% | 80-85% |
| 1-5% | 5-14% | 85-90% |
| 1-5% | 1-9% | 90-94% |
| 5-10% | 85-94% | 1-5% |
| 5-10% | 80-90% | 5-10% |
| 5-10% | 75-85% | 10-15% |
| 5-10% | 70-80% | 15-20% |

TABLE A-continued

| Weight percent of water in multi-component solvent system | Weight percent of first water-miscible organic solvent in multi-component solvent system | Weight percent of second water-miscible organic solvent in multi-component solvent system |
| --- | --- | --- |
| 5-10% | 65-75% | 20-25% |
| 5-10% | 60-70% | 25-30% |
| 5-10% | 55-65% | 30-35% |
| 5-10% | 50-60% | 35-40% |
| 5-10% | 45-55% | 40-45% |
| 5-10% | 40-50% | 45-50% |
| 5-10% | 35-45% | 50-55% |
| 5-10% | 30-40% | 55-60% |
| 5-10% | 25-35% | 60-65% |
| 5-10% | 20-30% | 65-70% |
| 5-10% | 15-25% | 70-75% |
| 5-10% | 10-20% | 75-80% |
| 5-10% | 5-15% | 80-85% |
| 5-10% | 1-10% | 85-89% |
| 10-15% | 80-89% | 1-5% |
| 10-15% | 75-85% | 5-10% |
| 10-15% | 70-80% | 10-15% |
| 10-15% | 65-75% | 15-20% |
| 10-15% | 60-70% | 20-25% |
| 10-15% | 55-65% | 25-30% |
| 10-15% | 50-60% | 30-35% |
| 10-15% | 45-55% | 35-40% |
| 10-15% | 40-50% | 40-45% |
| 10-15% | 35-45% | 45-50% |
| 10-15% | 30-40% | 50-55% |
| 10-15% | 25-35% | 55-60% |
| 10-15% | 20-30% | 60-65% |
| 10-15% | 15-25% | 65-70% |
| 10-15% | 10-20% | 70-75% |
| 10-15% | 5-15% | 75-80% |
| 10-15% | 1-10% | 80-84% |
| 15-20% | 75-84% | 1-5% |
| 15-20% | 70-80% | 5-10% |
| 15-20% | 65-75% | 10-15% |
| 15-20% | 60-70% | 15-20% |
| 15-20% | 55-65% | 20-25% |
| 15-20% | 50-60% | 25-30% |
| 15-20% | 45-55% | 30-35% |
| 15-20% | 40-50% | 35-40% |
| 15-20% | 35-45% | 40-45% |
| 15-20% | 30-40% | 45-50% |
| 15-20% | 25-35% | 50-55% |
| 15-20% | 20-30% | 55-60% |
| 15-20% | 15-25% | 60-65% |
| 15-20% | 10-20% | 65-70% |
| 15-20% | 5-15% | 70-75% |
| 15-20% | 1-10% | 75-79% |
| 20-25% | 70-79% | 1-5% |
| 20-25% | 65-75% | 5-10% |
| 20-25% | 60-70% | 10-15% |
| 20-25% | 55-65% | 15-20% |
| 20-25% | 50-60% | 20-25% |
| 20-25% | 45-55% | 25-30% |
| 20-25% | 40-50% | 30-35% |
| 20-25% | 35-45% | 35-40% |
| 20-25% | 30-40% | 40-45% |
| 20-25% | 25-35% | 45-50% |
| 20-25% | 20-30% | 50-55% |
| 20-25% | 15-25% | 55-60% |
| 20-25% | 10-20% | 60-65% |
| 20-25% | 5-15% | 65-70% |
| 20-25% | 1-10% | 70-74% |
| 25-30% | 65-74% | 1-5% |
| 25-30% | 60-70% | 5-10% |
| 25-30% | 55-65% | 10-15% |
| 25-30% | 50-60% | 15-20% |
| 25-30% | 45-55% | 20-25% |
| 25-30% | 40-50% | 25-30% |
| 25-30% | 35-45% | 30-35% |
| 25-30% | 30-40% | 35-40% |
| 25-30% | 25-35% | 40-45% |
| 25-30% | 20-30% | 45-50% |
| 25-30% | 15-25% | 50-55% |
| 25-30% | 10-20% | 55-60% |
| 25-30% | 5-15% | 60-65% |
| 25-30% | 1-10% | 65-69% |
| 30-35% | 60-69% | 1-5% |
| 30-35% | 55-65% | 5-10% |
| 30-35% | 50-60% | 10-15% |
| 30-35% | 45-55% | 15-20% |
| 30-35% | 40-50% | 20-25% |
| 30-35% | 35-45% | 25-30% |
| 30-35% | 30-40% | 30-35% |
| 30-35% | 25-35% | 35-40% |
| 30-35% | 20-30% | 40-45% |
| 30-35% | 15-25% | 45-50% |
| 30-35% | 10-20% | 50-55% |
| 30-35% | 5-15% | 55-60% |
| 30-35% | 1-10% | 60-64% |
| 35-40% | 55-64% | 1-5% |
| 35-40% | 50-60% | 5-10% |
| 35-40% | 45-55% | 10-15% |
| 35-40% | 40-50% | 15-20% |
| 35-40% | 35-45% | 20-25% |
| 35-40% | 30-40% | 25-30% |
| 35-40% | 25-35% | 30-35% |
| 35-40% | 20-30% | 35-40% |
| 35-40% | 15-25% | 40-45% |
| 35-40% | 10-20% | 45-50% |
| 35-40% | 5-15% | 50-55% |
| 35-40% | 1-10% | 55-59% |
| 40-45% | 50-59% | 1-5% |
| 40-45% | 45-55% | 5-10% |
| 40-45% | 40-50% | 10-15% |
| 40-45% | 35-45% | 15-20% |
| 40-45% | 30-40% | 20-25% |
| 40-45% | 25-35% | 25-30% |
| 40-45% | 20-30% | 30-35% |
| 40-45% | 15-25% | 35-40% |
| 40-45% | 10-20% | 40-45% |
| 40-45% | 5-15% | 45-50% |
| 40-45% | 1-10% | 50-54% |
| 45-50% | 45-54% | 1-5% |
| 45-50% | 40-50% | 5-10% |
| 45-50% | 35-45% | 10-15% |
| 45-50% | 30-40% | 15-20% |
| 45-50% | 25-35% | 20-25% |
| 45-50% | 20-30% | 25-30% |
| 45-50% | 15-25% | 30-35% |
| 45-50% | 10-20% | 35-40% |
| 45-50% | 5-15% | 40-45% |
| 45-50% | 1-10% | 45-49% |
| 50-55% | 40-49% | 1-5% |
| 50-55% | 35-45% | 5-10% |
| 50-55% | 30-40% | 10-15% |
| 50-55% | 25-35% | 15-20% |
| 50-55% | 20-30% | 20-25% |
| 50-55% | 15-25% | 25-30% |
| 50-55% | 10-20% | 30-35% |
| 50-55% | 5-15% | 35-40% |
| 50-55% | 1-10% | 40-44% |
| 55-60% | 35-44% | 1-5% |
| 55-60% | 30-40% | 5-10% |
| 55-60% | 25-35% | 10-15% |
| 55-60% | 20-30% | 15-20% |
| 55-60% | 15-25% | 20-25% |
| 55-60% | 10-20% | 25-30% |
| 55-60% | 5-15% | 30-35% |
| 55-60% | 1-10% | 35-39% |
| 60-65% | 30-39% | 1-5% |
| 60-65% | 25-35% | 5-10% |
| 60-65% | 20-30% | 10-15% |
| 60-65% | 15-25% | 15-20% |
| 60-65% | 10-20% | 20-25% |
| 60-65% | 5-15% | 25-30% |
| 60-65% | 1-10% | 30-34% |

TABLE A-continued

| Weight percent of water in multi-component solvent system | Weight percent of first water-miscible organic solvent in multi-component solvent system | Weight percent of second water-miscible organic solvent in multi-component solvent system |
|---|---|---|
| 65-70% | 25-34% | 1-5% |
| 65-70% | 20-30% | 5-10% |
| 65-70% | 15-25% | 10-15% |
| 65-70% | 10-20% | 15-20% |
| 65-70% | 5-15% | 20-25% |
| 70-75% | 20-29% | 1-5% |
| 70-75% | 15-25% | 5-10% |
| 70-75% | 10-20% | 10-15% |
| 70-75% | 5-15% | 15-20% |
| 75-80% | 15-24% | 1-5% |
| 75-80% | 10-20% | 5-10% |
| 75-80% | 5-15% | 10-15% |

The contacting step is often carried out for a time sufficient to produce a product solution comprising (soluble) FDCA pathway product at a concentration of at least 2 wt %, at least 3 wt %, at least 4 wt %, at least 5 wt %, at least 6 wt %, at least 7 wt %, at least 8 wt %, at least 9 wt %, at least 10 wt %, at least 11 wt %, at least 12 wt %, at least 13 wt %, at least 14 wt %, or at least 15 wt % or at a concentration that is within a range defined by any two of the aforementioned values. Correspondingly, when a product solution is produced that comprises the (soluble) FDCA pathway product it is produced at a concentration of at least 2 wt %, at least 3 wt %, at least 4 wt %, at least 5 wt %, at least 6 wt %, at least 7 wt %, at least 8 wt %, at least 9 wt %, at least 10 wt %, at least 11 wt %, at least 12 wt %, at least 13 wt %, at least 14 wt %, or at least 15 wt %) or a at concentration that is within a range defined by any two of the aforementioned values. The term "product solution" refers herein to a solution of soluble FDCA pathway product and other soluble components of the reaction mixture in the oxidation solvent. The phrase "a time sufficient to produce a product solution comprising the FDCA pathway product at a concentration of" is used herein to refer to a minimum amount of time required to produce the specified concentration of the FDCA pathway product in the product solution.

More typically, the contacting step is carried out for a time sufficient to produce a product solution comprising the FDCA pathway product at a concentration of at least 6 wt %, at least 7 wt %, at least 8 wt %, at least 9 wt %, at least 10 wt %, at least 11 wt %, at least 12 wt %, at least 13 wt %, at least 14 wt %, or at least 15 wt % or at a concentration that is within a range defined by any two of the aforementioned values. Correspondingly, when a product solution is produced that comprises the FDCA pathway product it is produced at a concentration of at least 6 wt %, at least 7 wt %, at least 8 wt %, at least 9 wt %, at least 10 wt %, at least 11 wt %, at least 12 wt %, at least 13 wt %, at least 14 wt %, or at least 15 wt %, respectively or a concentration that is within a range defined by any two of the aforementioned values.

Heterogeneous oxidation catalysts employed in the practice of the present disclosure typically have the noble metal dispersed on the internal and external surfaces of the support. The term "noble metal" refers herein to ruthenium, rhodium, palladium, silver, osmium, iridium, platinum or gold. In certain preferred embodiments, the metal is selected from the group consisting of platinum, gold, and a combination thereof. Typically, the metal is platinum. In some embodiments, the metal is gold. The heterogeneous oxidation catalyst may further include a promoter to enhance the performance of the heterogeneous oxidation catalyst. When the metal is platinum, gold, or combination thereof, suitable promoters include, for example, Pd, Ir, Mo, or W, and the like.

The heterogeneous oxidation catalyst typically comprises the noble metal at a total metal loading in the range of from or any number in between 0.3% to 5% by weight. In some embodiments, the metal loading is in the range of from or any number in between 0.5% to 4% by weight. In some embodiments, the metal loading ranges from or any number in between 2-4 wt %. In some embodiments, the metal loading is 2 wt %. In some embodiments, the metal loading is 3 wt %. In some embodiments, the metal loading is 4 wt %. When two or more metals are employed, the heterogeneous oxidation catalyst may comprise a plurality of heterogeneous oxidation catalyst particles, each comprising the two or more metals, or the heterogeneous oxidation catalyst may comprise a mixture of heterogeneous oxidation catalyst metal-particle species, e.g., a first plurality of heterogeneous oxidation catalyst particles comprising a first metal species and a second plurality of heterogeneous oxidation catalyst particles comprising a second metal species. Methods for preparing the heterogeneous oxidation catalysts employed in the practice of the present disclosure are described in detail in section II, herein below, as well as in the Examples.

The solid support component of the heterogeneous oxidation catalyst may comprise any type of material known by those having ordinary skill in the art as being suitable for use as a catalytic support that also has the specific surface area requirement described herein. Suitable materials include, for example, a metal oxide, a carbonaceous material, a polymer, a metal silicate, a metal carbide, or any composite material prepared therefrom. Exemplary metal oxides include silicon oxide (silica), zirconium oxide (zirconia), titanium oxide (titania), or aluminum oxide (alumina), and the like. As used herein, the term "carbonaceous" refers to graphite and carbon black. Exemplary metal silicates include, for example, an orthosilicate, a borosilicate, or an aluminosilicate (e.g., a zeolite), and the like. Exemplary metal carbides include, for example, silicon carbide, and the like. Suitable polymeric solid support materials include polystyrene, polystyrene-co-divinyl benzene, polyamides, or polyacrylamides, and the like.

Suitable solid support materials also include a composite material prepared from, or comprising a binder and a material selected from the group consisting of a metal oxide, a carbonaceous material, a polymer, a metal silicate, and a metal carbide. In some embodiments, the binder is a resin. In other embodiments, the composite material comprises a carbonized binder and a material selected from the group consisting of a metal oxide, a carbonaceous material, a metal silicate, and a metal carbide. In one embodiment, the composite material comprises a carbonized binder and carbon black. Methods for making such carbon-based composite materials is described in PCT Application No. PCT/US15/28358, which is expressly incorporated herein by reference in its entirety. Illustrative support materials are described in the Examples herein.

In some embodiments, the solid support comprises a carbon black material selected from the group consisting of Aditya Birla CDX-KU, Aditya Birla CSCUB, Aditya Birla R2000B, Aditya Birla R2500UB, Aditya Birla R3500B, Aditya Birla R5000U2, Arosperse 5-183A, Asbury 5302, Asbury 5303, Asbury 5345, Asbury 5348R, Asbury 5358R, Asbury 5365R, Asbury 5368, Asbury 5375R, Asbury 5379, Asbury A99, Cabot Monarch 120, Cabot Monarch 280, Cabot Monarch 570, Cabot Monarch 700, Cabot Norit Darco 12x20L1, Cabot Vulcan XC72, Continental N120, Continental N234, Continental N330, Continental N330-C, Continental N550, Norit ROX 0.8, Orion Arosperse 138, Orion Arosperse 15, Orion Color Black FW 2, Orion Color Black FW 255, Orion HiBlack 40B2, Orion Hi-Black 50 L, Orion Hi-Black 50 LB, Orion Hi-Black 600 L, Orion HP-160, Orion Lamp Black 101, Orion N330, Orion Printex L6, Sid Richardson Ground N115, Sid Richardson Ground SR155, Sid Richardson SC159, Sid Richardson SC419, Timcal Ensaco 150G, Timcal Ensaco 250G, Timcal Ensaco 260G, and Timcal Ensaco 350G.

Metal impregnation of the solid support typically results in a negligible change in the specific surface, pore diameters, and specific volume of the solid support. Heterogeneous oxidation catalysts that are suitable for use in the present disclosure are typically prepared using a solid support that comprises a plurality of pores and a specific surface area in the range of from 20 $m^2/g$ to 500 $m^2/g$, such as e.g., 20, 30, 40, 50, 60, 70, 80, 90, 100, 120, 140, 160, 180, 200, 225, 250, 275, 300, 325, 350, 375, 400, 425, 450, 475, or 500 $m^2/g$ or is within a range defined by any two of the aforementioned surface areas. Specific surface area can be determined using known methods, such as, for example, the method of Bruanauer, Emmett and Teller (*J. Am. Chem. Soc.* 1938, 60:309-311) and/or mercury porosimetry. See e.g., ASTM Test Methods D3663, D6556, and D4567, each of which is incorporated by reference in its entirety. Typically, heterogeneous oxidation catalysts (and solid supports) employed in the practice of the present disclosure have a specific surface area in the range of from or any number in between 25 $m^2/g$ to 250 $m^2/g$, and sometimes in the range of from or any number in between 25 $m^2/g$ to 225 $m^2/g$, or from or any number in between 25 $m^2/g$ to 200 $m^2/g$, or from or any number in between 25 $m^2/g$ to 175 $m^2/g$, or from or any number in between 25 $m^2/g$ to 150 $m^2/g$, or from or any number in between 25 $m^2/g$ to 125 $m^2/g$, or from or any number in between 25 $m^2/g$ to 100 $m^2/g$. These specific surface areas are relatively low when compared to highly porous catalytic support materials that are more typically used in the art, such as, for example, activated carbon. The relatively low surface area of the heterogeneous oxidation catalysts employed in the oxidative processes of the present disclosure is believed to favorably contribute to the high selectivity and yields observed with respect to the conversion of the furanic oxidation substrates to FDCA and FDCA pathway intermediate compounds under substantially base-free conditions.

Commensurate with the relatively low specific surface areas, the heterogeneous oxidation catalysts (and solid support components thereof) employed in the practice of the present disclosure also typically have relatively moderate to low specific pore volumes when compared to other oxidation catalysts. Heterogeneous oxidation catalysts (and solid support components thereof) employed in the practice of the present disclosure typically have a specific pore volume (determined on the basis of pores having a diameter of 1.7 nm to 100 nm) that is, from or any number in between 0.1 $cm^3/g$ to 1.5 $cm^3/g$, from or any number in between 0.1 $cm^3/g$ to 0.8 $cm^3/g$, from or any number in between 0.1 $cm^3/g$ to 0.7 $cm^3/g$, from or any number in between 0.1 $cm^3/g$ to 0.6 $cm^3/g$, from or any number in between 0.1 $cm^3/g$ to 0.5 $cm^3/g$, from or any number in between 0.2 $cm^3/g$ to 0.8 $cm^3/g$, from or any number in between 0.2 $cm^3/g$ to 0.7 $cm^3/g$, from or any number in between 0.2 $cm^3/g$ to 0.6 $cm^3/g$, from or any number in between 0.2 $cm^3/g$ to 0.5 $cm^3/g$, from or any number in between 0.3 $cm^3/g$ to 1 $cm^3/g$, from or any number in between 0.3 $cm^3/g$ to 0.9 $cm^3/g$, from or any number in between 0.3 $cm^3/g$ to 0.8 $cm^3/g$, from or any number in between 0.3 $cm^3/g$ to 0.7 $cm^3/g$, from or any number in between 0.3 $cm^3/g$ to 0.6 $cm^3/g$, or from or any number in between 0.3 $cm^3/g$ to 0.5 $cm^3/g$ or within a range defined by any two of the aforementioned values, as measured by a method for determining pore diameters and specific pore volumes, such as that described in E. P. Barrett, L. G. Joyner, P. P. Halenda, *J. Am. Chem. Soc.* (1951) 73:373-380 and ASTM D4222-03 (2008) (the method referred to herein as the "BJH method"), both of which are expressly incorporated herein by reference in their entireties, and by the method of mercury porosimetry (e.g., using a mercury porosimeter, such as, for example, the Micromeritics Autopore V 9605 Mercury Porosimeter (Micromeritics Instrument Corp., Norcross, Ga.) in accordance with the manufacturer's instructions). See e.g., ASTM 3663, ASTM D-4284-12 and D6761-07 (2012), all of which are incorporated herein by reference.

Typically, the heterogeneous oxidation catalyst has a mean pore diameter in the range of from or any number in between 10 nm to 100 nm, as measured by the BJH method and/or mercury porosimetry. More typically, the heterogeneous oxidation catalyst has a mean pore diameter in the range of from or any number in between 10 nm to 90 nm, as measured by the BJH method and/or mercury porosimetry. In some embodiments, the mean pore diameter is in the range of from or any number in between 10 nm to 80 nm, or from or any number in between 10 nm to 70 nm, or from or any number in between 10 nm to 60 nm, and often from or any number in between 10 nm to 50 nm, as determined by the BJH method and/or mercury porosimetry. In some embodiments, the mean pore diameter is in the range of from or any number in between 20 nm to 100 nm, as measured by the BJH method and/or mercury porosimetry. In certain of these embodiments, the mean pore diameter is in the range from or any number in between 20 nm to 90 nm, or from or any number in between 20 nm to 80 nm, or from or any number in between 20 nm to 70 nm, or from or any number in between 20 nm to 60 nm, or from or any number in between 10 nm to 50 nm, as determined by the BJH method and/or mercury porosimetry. The catalysts employed in the practice of the present disclosure typically have a relatively high concentration of pores in the size ranges described above.

In some embodiments, the heterogeneous oxidation catalyst comprises a second plurality of pores. In this embodiment, the pore size distribution of the heterogeneous oxidation catalyst and underlying solid support is bimodal, having a first distribution made up of a first plurality of pore diameters and a second distribution made up of a second plurality of pore diameters, with each plurality having a mean pore diameter associated with it. The second plurality of pores has a mean pore diameter that is different from the mean pore diameter of the second plurality, yet is typically still in the range of from or any number in between 10 nm to 100 nm, as determined by the BJH method and/or mercury porosimetry.

Typically, the heterogeneous oxidation catalysts comprise a pore volume, wherein at least 50% of the pore volume is attributable to pores having a pore diameter in the range of from or any number in between 5 nm to 100 nm (as determined by the BJH method and/or mercury porosimetry on the basis of pores having a diameter of from 1.7 nm to 100 nm). Typically, the heterogeneous oxidation catalyst has a pore volume, wherein at least 60%, and in some embodiments, at least 70%, or at least 80%, or at least 90% of the pore volume is attributable to pores having pore diameter of from or any number in between 10 nm to 100 nm (as determined by the BJH method and/or mercury porosimetry on the basis of pores having a diameter of from 1.7 nm to 100 nm).

In some embodiments, at least 35%, at least 40%, at least 45%, or at least 50% of the pore volume of the heterogeneous oxidation catalysts employed in the practice of the present disclosure (as measured by the BJH method and/or mercury porosimetry on the basis of pores having a diameter from 1.7 nm to 100 nm) is attributable to pores having a pore diameter of from or any number in between 10 nm to 50 nm. For example, from or any number in between 35% to 80%, from or any number in between 35% to 75%, from or any number in between 35% to 65%, from or any number in between 40% to 80%, from or any number in between 40% to 75%, or from or any number in between 40% to 70% of the pore volume of the heterogeneous oxidation catalyst is attributable to pores having a mean pore diameter in the range from or any number in between 10 nm to 50 nm (as measured by the BJH method and/or mercury porosimetry on the basis of pores having a diameter from 1.7 nm to 100 nm).

Typically, no more than 2.5% of the pore volume of the heterogeneous oxidation catalyst is attributable to pores having a pore diameter of less than 10 or 5 nm. More typically, no more than 3%, or no more than 4%, or no more than 5%, or no more than 10% or no more than a value that is within a range defined by any two of the aforementioned percentages of the pore volume of the heterogeneous oxidation catalyst is attributable to pores having a pore diameter of less than 10 or 5 nm, as determined by the BJH method and/or mercury porosimetry. To prepare heterogeneous oxidation catalysts that are suitable for use in the practice of the present disclosure, solid supports are selected which possess the foregoing physical properties. The pore structure of the support material is typically retained in the finished heterogeneous oxidation catalyst after metal impregnation.

In certain preferred embodiments, the noble metal in the heterogeneous oxidation catalyst comprises or consists essentially of platinum, and in some embodiments consists of platinum, and in each case, wherein the solid support is selected from the group consisting of silica and a carbonaceous material. In these preferred embodiments, the heterogeneous oxidation catalyst typically comprises a mean pore diameter in the range of from or any number in between 10 nm to 100 nm, and often in the range of from or any number in between 20 nm to 100 nm, as determined by the BJH method and/or mercury porosimetry.

In carrying out the processes of the present disclosure, oxygen may be provided in neat form (i.e., $O_2$ only, with no other gases) or as a component of a mixture of gases (e.g., air, oxygen-enriched air, and the like). The molar ratio of oxygen to the furanic oxidation substrate during the contacting step is typically in the range of from 2:1 to 10:1. In some embodiments, the molar ratio of oxygen to the furanic oxidation substrate is from 2:1 to 10:1, or from 3:1 to 5:1. During the contacting step, oxygen is typically present at a partial pressure in the range of from or any number in between 50 psig to 1000 psig. More typically, oxygen is present at a partial pressure in the range of from or any number in between 50 psig to 200 psig. In some embodiments, oxygen is present at a partial pressure in the range from or any number in between 50-200 psig, 100-300 psig, 200-400 psig, 300-500 psig, 400-600 psig, 500-700 psig, 600-800 psig, 700-900 psig, or 800-1000 psig, or within a range defined by any two of the aforementioned partial pressures.

The contacting (oxidation) step is typically carried out at a temperature in the range of from or any number in between 50° C. to 200° C. In some embodiments, the contacting step is carried out at a temperature in the range of from or any number in between 80° C. to 180° C., and in other embodiments, the contacting step carried out at a temperature in the range from or any number in between 90° C. to 160° C. or from or any number in between 100° C. to 160° C. In certain preferred embodiments, the contacting step is carried out at a temperature in the range of from or any number in between 90° C. to 180° C., and sometimes it is carried out at a temperature in the range of from or any number in between 110° C. to 160° C.

Figure 4:
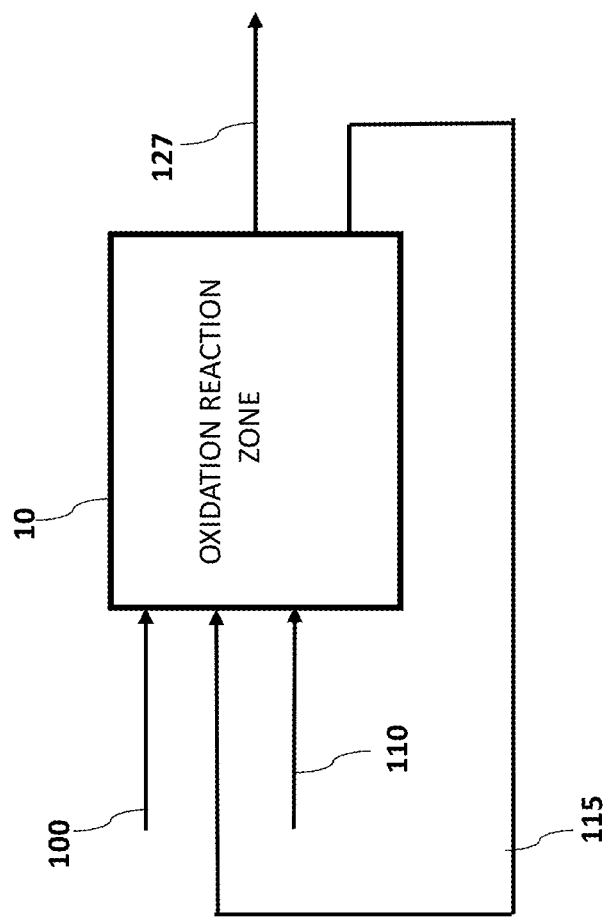
FIG. 4 is a schematic of a single oxidation reaction zone process for converting a furanic oxidation substrate to a desired FDCA pathway product.

An illustrative process for carrying out the production of the desired FDCA pathway product from a furanic oxidation substrate is depicted in FIG. 4. In this process, which utilizes a single oxidation reaction zone, an oxygen feed stream 110 comprising $O_2$ (in neat form or as a component of a mixture of gases) and a furanic oxidation substrate feedstock stream 100 are passed into an oxidation zone 10 to produce an FDCA pathway product stream 127 and an optional recycle stream 115, which comprises unreacted furanic oxidation substrate.

In some embodiments, it may be desirable to carry out the oxidation of the furanic oxidation substrate to the desired FDCA pathway product in a series of two or more oxidation steps, where the first oxidation step is as described above, and where the second oxidation step comprises:

(b) contacting a second oxidation feedstock comprising a second furanic oxidation substrate and a second oxidation solvent with oxygen in the presence of a second heterogeneous oxidation catalyst under conditions sufficient to form a second reaction mixture for oxidizing the second furanic oxidation substrate to produce a second FDCA pathway product, wherein (the first) contacting step (a) produces a first FDCA pathway product that is an FDCA pathway intermediate compound, either alone or together with FDCA, wherein the second furanic oxidation substrate is the first FDCA pathway product, wherein the second reaction mixture is substantially free of added base, and wherein the second heterogeneous oxidation catalyst comprises a second solid support and a noble metal that may be the same or different from the (first) noble metal in step (a), and wherein the second heterogeneous oxidation catalyst comprises a plurality of pores and a specific surface area in the range of from or any number in between 20 $m^2/g$ to 500 $m^2/g$, such as e.g., 20, 30, 40, 50, 60, 70, 80, 90, 100, 120, 140, 160, 180, 200, 225, 250, 275, 300, 325, 350, 375, 400, 425, 450, 475, or 500 $m^2/g$ or is within a range defined by any two of the aforementioned surface areas.

The second FDCA pathway product is a downstream oxidation product of the first FDCA pathway product, and is typically FFCA, or FDCA. Typically, the second FDCA pathway product is FDCA. Usually, the second oxidation step is free of added base.

Noble metals, catalyst metal loadings, solid support materials, and reaction conditions (e.g., reaction temperatures, oxygen (partial) pressure, molar ratio of oxygen to furanic oxidation substrate, and the like) that are suitable for using in the first oxidation process are also suitable for using in the second oxidation process. The second heterogeneous oxidation catalyst may be the same or different than that used in the first oxidation process (i.e., the "first" heterogeneous oxidation catalyst"). Oxidation solvents that are suitable for use in the second oxidation feedstock are the same as those that are suitable for use in the first oxidation process (i.e., the "first oxidation solvent"). The multi-stage oxidation process format may be desirable if optimal production of the desired FDCA pathway product requires a change in reaction conditions during the course of conversion from the furanic oxidation substrate to the desired FDCA pathway product. For example, it may be desirable to carry out the second oxidation reaction at a higher or lower temperature than the first oxidation reaction, or maintain the molar ratio of oxygen to feedstock component in the second oxidation reaction at a higher or lower ratio than in the first oxidation reaction, or maintain the partial pressure of oxygen in the second oxidation reaction at a higher or lower partial pressure than in the first oxidation reaction. The composition of the second oxidation solvent may be the same as the composition of the first oxidation solvent or it may be different. If it is different, it may still have in common one or more of the same solvent species component. The noble metal in the second heterogeneous oxidation catalyst is typically platinum, gold, or a combination thereof. Usually, the noble metal used in the second heterogeneous oxidation catalyst is platinum.

In certain preferred embodiments, the noble metal in the second heterogeneous oxidation catalyst comprises or consists essentially of platinum, and in some embodiments consists of platinum, and in each case, wherein the second solid support is selected from the group consisting of silica and a carbonaceous material. In these preferred embodiments, the second heterogeneous oxidation catalyst typically comprises a mean pore diameter in the range of from or any number in between 10 nm to 100 nm, and often in the range of from or any number in between 20 nm to 100 nm, such as e.g., 10, 20, 30, 40, 50, 60, 70, 80, 90, or 100 nm or within a range defined by any two of the aforementioned mean pore diameters.

Figure 5:
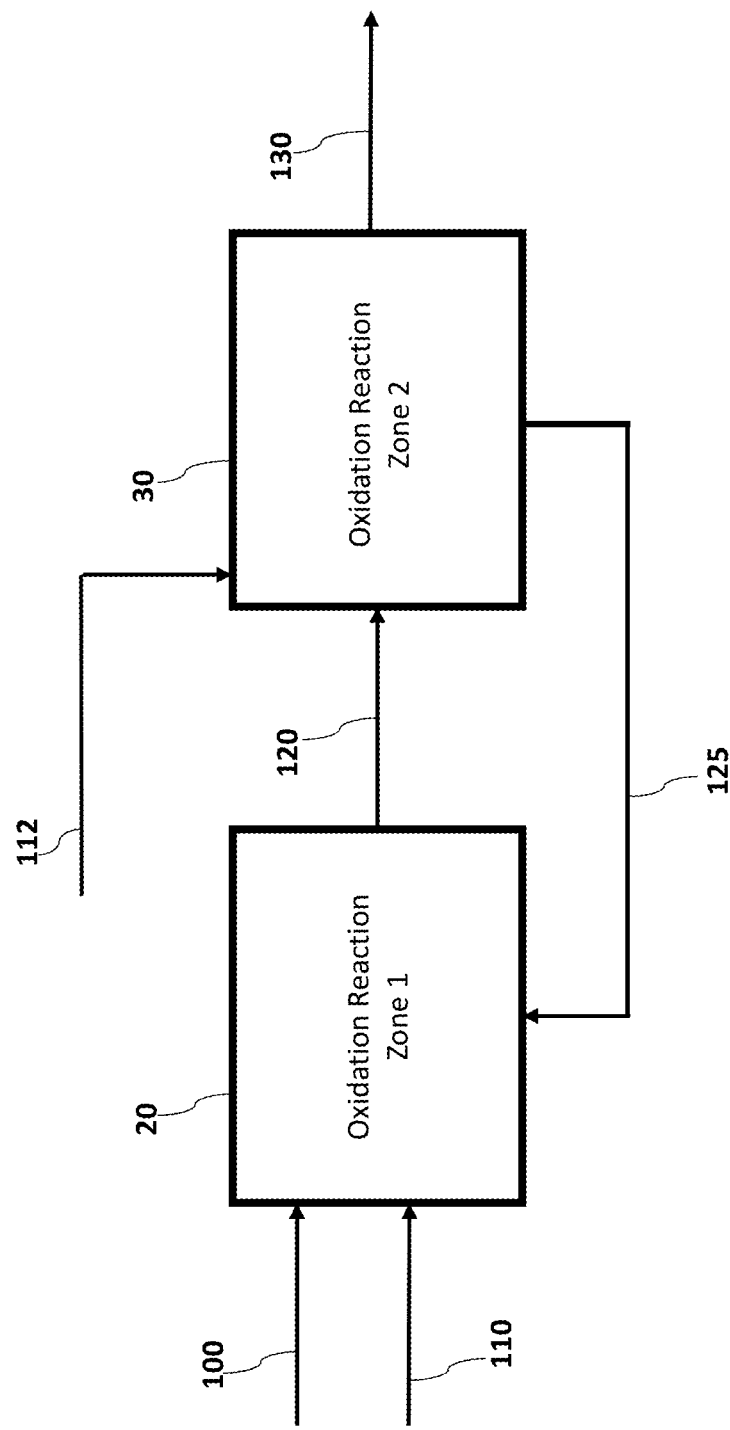
FIG. 5 is a schematic of an integrated multi-oxidation reaction zone process for converting a furanic oxidation substrate to a desired FDCA pathway product.

FIG. 5 provides an illustrative integrated process for carrying out the production of the desired FDCA pathway product in two stages, using two oxidation reaction zones in series: oxidation reaction zone 1 20 and oxidation reaction zone 2 30. In this integrated process, an oxidant feed stream 110 comprising $O_2$, and a furanic oxidation substrate feedstock stream 100 are passed into oxidation reaction zone 20 to produce oxidation reaction zone 1 product stream 120. Oxidation reaction zone 1 product stream comprises an FDCA pathway intermediate compound and the oxidation solvent. Product stream 120, and oxidant feed stream 112 comprising $O_2$ are then passed into a oxidation reaction zone 2 30 to produce oxidation reaction zone product stream 130 and an optional recycle stream 125 which comprises unreacted furanic oxidation substrate. Oxidation reaction zone product stream 130 comprises an oxidized product of the FDCA pathway intermediate compound from oxidation reaction zone 30, which may be FDCA and/or an FDCA pathway intermediate that, in either case, is an oxidation product of the FDCA pathway intermediate present in oxidation reaction zone 1 product stream 120.

The processes of the present disclosure may be carried out in batch, semi-batch, or continuous reactor format using reactors known in the art, such as, for example, fixed bed reactors, trickle bed reactors, slurry phase reactors, moving bed reactors, and the like. The relatively high solubilities of reactants and products (particularly, the FDCA pathway product) in the oxidation solvent facilitate the use of all such reactor formats, and particularly the fixed bed reactor format.

FDCA pathway product(s) produced by the oxidation processes described herein may be recovered from the reaction mixture by separating the heterogeneous oxidation catalyst from a product solution comprising the FDCA pathway product(s) and the oxidation solvent. The product solution includes the oxidation solvent and soluble components of the reaction mixture and excludes the heterogeneous oxidation catalyst. The product solution may be further concentrated with respect to the soluble components by removal of a portion of the oxidation solvent. Oxidation solvent removal may be accomplished by evaporation (e.g., by using an evaporator), distillation, and the like.

Alternatively, or further to the isolation step, the FDCA pathway product may be purified. Preferably, the FDCA pathway product is purified by crystallization. Thus, in one embodiment, the present disclosure provides a process for producing a crystalline FDCA pathway product composition, the method comprising:

providing a crystallization solution comprising an FDCA pathway product and a crystallization solvent that is a solvent selected from the group consisting of an organic solvent and a multi-component solvent; initiating crystallization of the FDCA pathway product; and producing a plurality of FDCA pathway product crystals of different particle sizes.

As used herein, the term "crystallization solvent" refers to a solvent from which the FDCA pathway product can be crystallized when conditions are imposed that cause a reduction in solubility of the FDCA pathway product in the crystallization solvent (e.g., temperature reduction (cooling) or solvent removal). The crystallization solvent may be water, an organic solvent, or a multi-component solvent comprising water and a water-miscible organic solvent or two or more organic solvent species. The crystallization process may directly follow the oxidation process (e.g., either a single stage oxidation process or multi-stage oxidation process), or it may follow other unit operations downstream of the oxidation process.

When crystallization follows FDCA pathway product generation, the crystallization solution is typically a product solution comprising the FDCA pathway product and the oxidation solvent. In such embodiment, therefore, the crystallization solvent is the same as the oxidation solvent (e.g., the first oxidation solvent (single stage oxidation) or the second oxidation solvent (for two-stage oxidation)). Some solvents that are suitable for use in the oxidation solvent are also suitable for use as the crystallization solvent.

Industrial solution phase crystallizations are typically performed by introducing a saturated (or super-saturated) solution of the product into a crystallizer in which the solution is subjected to crystallization conditions, and crystallization is initiated by, for example, lowering the temperature or concentrating the solution by solvent evaporation (i.e., solvent removal), or a combination of both. Solvent evaporation may be used to concentrate the solution to initiate crystallization, and may also be used to adjust the solvent composition to lower the solubility of the FDCA pathway product. As used herein, the term "crystallization conditions" refers to an adjustment in temperature and/or adjustment in crystallization solution concentration and/or adjustment in crystallization solution composition that causes the initiation of crystallization of the FDCA pathway product.

In one embodiment where crystallization conditions include a temperature adjustment, the present disclosure provides a process for producing a crystalline FDCA preparation, the method comprising:

providing a crystallization solution comprising the FDCA pathway product and a crystallization solvent at a first temperature in the range of or any number in between 50° C. to 220° C., such as e.g., 50, 60, 70, 80, 90, 100, 110, 120, 130, 140, 150, 160, 180, 190, 200, 210, or 220° C. or within a range defined by any two of the aforementioned temperatures; and cooling the crystallization solution to a second temperature that is lower than the first temperature to form a plurality of FDCA pathway product crystals of different particle sizes.

Cooling reduces the solubility of the FDCA pathway product in the crystallization solvent, causing crystals of FDCA pathway product to form in the solution. The first temperature is typically in the range of from or any number in between 60° C. to 180° C., such as e.g., 60, 70, 80, 90, 100, 110, 120, 130, 140, 150, 160, or 180° C. or within a range defined by any two of the aforementioned temperatures. In some embodiments, the first temperature is in the range from or any number in between 70° C. to 150° C. such as e.g., 70, 80, 90, 100, 110, 120, 130, 140, or 150° C. or within a range defined by any two of the aforementioned temperatures. When the crystallization solution is cooled, it is typically cooled to a temperature that is at or below 60° C., such as e.g., equal to or less than 60, 50, 40, 30, 20, 10, 5, or 0° C. or within a range defined by any two of the aforementioned temperatures. More typically, it is cooled to a temperature at or below 50° C. or at or below 40° C. such as, e.g., equal to or less than 50, 40, 30, 20, 10, 5, or 0° C. or within a range defined by any two of the aforementioned temperatures.

In an embodiment where solvent removal (evaporation) is used to initiate crystallization, the present disclosure provides a method for producing a crystalline FDCA preparation, the method comprising:

(a) providing a first crystallization solution comprising FDCA and a first crystallization solvent selected from the group consisting of water, an organic solvent, and combinations thereof;

(b) removing a first portion of the first crystallization solvent from the first crystallization solution to produce a first FDCA pathway product slurry, wherein the first FDCA pathway product slurry comprises a first plurality of FDCA pathway product crystals and a second portion of the first crystallization solvent; and (c) separating the first plurality of FDCA pathway product crystals from the second portion of the first crystallization solvent.

In a further embodiment, the first plurality of FDCA pathway product crystals are recrystallized, by conducting the following additional steps:

(d) dissolving the first plurality of FDCA crystals in a second crystallization solvent to produce a second crystallization solution comprising FDCA and the second crystallization solvent; and (e) removing a first portion of the second crystallization solvent from the second crystallization solution to produce a second FDCA pathway product slurry, wherein the second FDCA pathway product slurry comprises a second plurality of FDCA pathway product crystals and a second portion of the second crystallization solvent; and (f) separating the second plurality of FDCA pathway product crystals from the second portion of the second crystallization solvent.

Removal of a portion of the crystallization solvent can be accomplished using known methods for removing solvents from a solution, such as, for example, evaporation, or distillation, and the like. Solvent removal may be facilitated by raising the temperature of the crystallization solution to effect vaporization of the crystallization solvent, or component thereof, resulting in one portion of the crystallization solvent being in a liquid phase and another portion being in a vapor phase, which is removed. Solvent removal results in an increase in concentration of the FDCA pathway product causing it to crystallize, thereby resulting in a slurry of FDCA pathway product crystals in a continuous liquid phase. Often, one or both of the first and second crystallization solvents is/are a multi-component solvent, where removing a first portion of the first and/or second crystallization solvents may involve removing all or part of one of the components of the multi-component solvent, and less or none of the other components. In these embodiments, the multi-component solvent may comprise one organic solvent species that is a light organic solvent and a second organic species that is a heavy organic solvent; or alternatively, it may comprise water and an organic solvent that is either a heavy or light, water-miscible organic solvent.

Separation of the first plurality of FDCA pathway product crystals and the second plurality of FDCA pathway product crystals from the second portion of the first crystallization solvent and the second portion of the second crystallization solvent, respectively, can be accomplished using known methods for separating solids from liquids, such as, for example, filtration, centrifugation, and the like.

The dissolving step (step (c)) is typically carried out at an elevated temperature to facilitate the dissolution of the first plurality of FDCA pathway product crystals in the second crystallization solvent. The temperature will depend on the crystallization solvent employed, but can be readily determined by raising the temperature, and optionally adding more second crystallization solvent, until the first plurality of FDCA pathway product crystals has dissolved completely. Typically, the dissolving step is carried out at a temperature in the range from or any number in between 50° C. to 220° C., such as e.g., 50, 60, 70, 80, 90, 100, 110, 120, 130, 140, 150, 160, 180, 190, 200, 210, or 220° C. or within a range defined by any two of the aforementioned temperatures. Often, the dissolving step is carried out at a temperature in the range from or any number in between 60° C. to 180° C., or in the range from or any number in between 70° C. to 150° C. such as e.g., 60, 70, 80, 90, 100, 110, 120, 130, 140, 150, 160, 170, or 180° C. or within a range defined by any two of the aforementioned temperatures. In some embodiments, the dissolving step is carried out at the higher end of these ranges, such as, for example, in the range from or any number in between 100° C. to 220° C., or from or any number in between 150° C. to 220° C., such as e.g., 100, 110, 120, 130, 140, 150, 160, 180, 190, 200, 210, or 220° C. or within a range defined by any two of the aforementioned temperatures.

The first and second crystallization solvent may be the same or different. In certain embodiments, at least one of the first and second crystallization solvents is a multi-component solvent that comprises a component solvent species common to both crystallization solvents. In some embodiments, the first crystallization solution comprising the FDCA pathway product is a product solution comprising the FDCA pathway product that results from the oxidation of the furanic oxidation substrate as described hereinabove. In other embodiments, the first crystallization solvent is not the same as the oxidation solvent used in the prior oxidation step. In these embodiments, all or a portion of the oxidation solvent may be removed prior to the crystallization step, by, for example, evaporation, and the like. The resulting solids can be dissolved in a different solvent (e.g., water or a different organic solvent species) or different multi-component solvent (i.e., a solvent that does not have the same composition as the oxidation solvent) to prepare the first crystallization solution.

In a specific embodiment, the crystallization solvent is a multi-component solvent comprising water and a water-miscible organic solvent. Thus, in a further embodiment, the present disclosure provides a process for producing a crystalline preparation of an FDCA pathway product, the process comprising:

providing a crystallization solution comprising an FDCA pathway product and a crystallization solvent that is a multi-component solvent comprising water and a water-miscible organic solvent;

initiating crystallization of the FDCA pathway product; and producing a plurality of FDCA pathway product crystals of different particle sizes.

Figure 3:
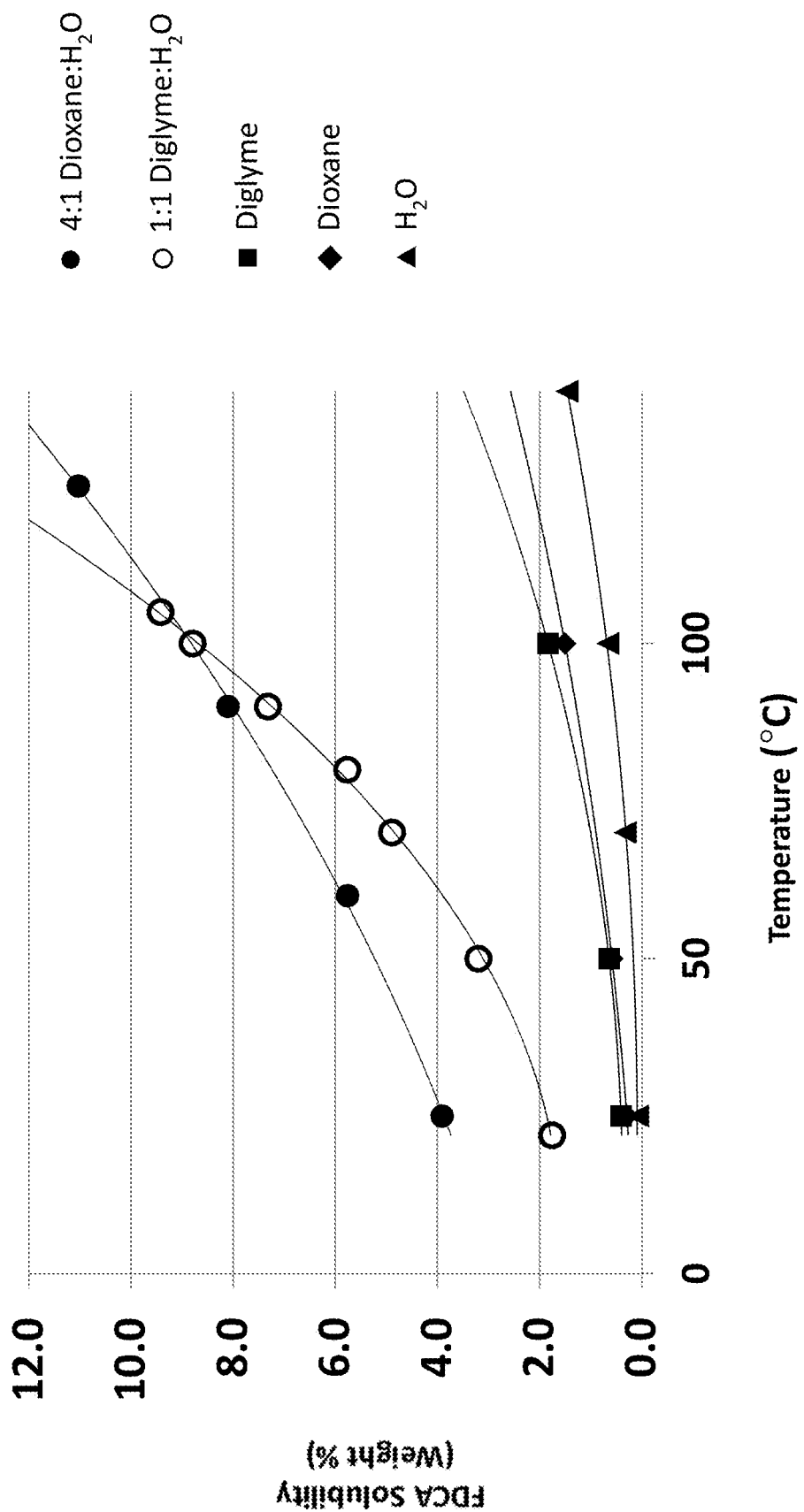
FIG. 3 depicts the solubility of FDCA (weight percent) in H$_2$O (▲), dioxane (♦), diglyme (■), 1:1 v/v diglyme:H$_2$O (○), and 4:1 v/v dioxane:H$_2$O (●) at temperatures in the range of from 22° C. to 140° C.

In this embodiment, the water-miscible organic solvent is typically a water-miscible aprotic organic solvent. In an exemplary embodiment, the water-miscible aprotic organic solvent is an ether, such as, for example dioxane, dioxolane, diglyme, and the like. To illustrate the benefit of such solvent system, FIG. 3 shows the FDCA solubility relationship in representative solvent compositions of the disclosure in comparison to water, dioxane, dioxolane (e.g., 1,3-dioxolane), and diglyme. The high solubility of FDCA in the solvent compositions of the disclosures enables the preparation of saturated solutions of FDCA in preparation for purification by crystallization. FIG. 3 also shows that, by adjusting the solvent composition by removing water or the organic solvent (or an azeotropic mixture of water and the organic solvent), it is possible to produce a solvent composition that is organic solvent rich (in the cases in which the chosen organic solvent is less volatile than water), or a solvent composition that is water rich (in the case that the chosen organic solvent is more volatile than water). FIG. 3 demonstrates that FDCA is considerably less soluble in water or organic solvents than the solvent compositions of the disclosure. The saturated solutions of FDCA may be subjected to crystallization conditions by lowering the temperature or by solvent evaporation to adjust the solvent composition, or both.

Exemplary water-miscible aprotic solvents that are suitable for use in the crystallization processes of the present disclosure include tetrahydrofuran, a glyme, a dioxane, a dioxolane, dimethylformamide, dimethylsulfoxide, sulfolane, acetone, N-methyl-2-pyrrolidone ("NMP"), methyl ethyl ketone ("MEK"), gamma-valerolactone, and the like. Preferably, the water-miscible aprotic organic solvent is an ether, such as, for example, a glyme, dioxane (for example 1,4-dioxane), dioxolane (e.g., 1,3-dioxolane), tetrahydrofuran, and the like. Glymes that are suitable for use in the practice of the present disclosure include, for example, monoglyme (1,2-dimethoxyethane, "DME"), ethyl glyme, diglyme (diethylene glycol dimethyl ether), ethyl diglyme, triglyme, butyl diglyme, tetraglyme, a polyglyme, a highly ethoxylated diether of a high molecular weight alcohol ("higlyme"), and the like. Often, the water-miscible aprotic organic solvent is glyme, diglyme, or dioxane.

In some embodiments, the water-miscible organic solvent species is at least 5 vol %, at least 10 vol %, at least 15 vol %, at least 20 vol %, at least 25 vol %, at least 30 vol %, at least 35 vol %, at least 40 vol %, at least 45 vol %, at least 50 vol %, at least 55 vol %, at least 60 vol %, at least 65 vol %, at least 70 vol %, at least 75 vol %, at least 80 vol %, at least 85 vol %, at least 90 vol %, or at least 95 vol % of the multi-component solvent or within a range defined by any two of the aforementioned values; and correspondingly, water is typically less than 95 vol %, less than 90 vol %, less than 85 vol %, less than 80 vol %, less than 75 vol %, less than 70 vol %, less than 65 vol %, less than 60 vol %, less than 55 vol %, less than 50 vol %, less than 45 vol %, less than 40 vol %, less than 35 vol %, less than 30 vol %, less than 25 vol %, less than 20 vol %, less than 15 vol %, less than 10 vol %, or less than 5 vol %, respectively, of the multi-component system or within a range defined by any two of the aforementioned values.

In some embodiments, the multi-component solvent comprises water in a range from or any number in between 1-5 wt % and a water-miscible organic solvent in a range from or any number in between 99-95 wt %. In some embodiments, the multi-component solvent comprises water in a range from or any number in between 5-10 wt % and a water-miscible organic solvent in a range from or any number in between 95-90 wt %. In some embodiments, the multi-component solvent comprises water in a range from or any number in between 10-15 wt % and a water-miscible organic solvent in a range from or any number in between 90-85 wt %. In some embodiments, the multi-component solvent comprises water in a range from or any number in between 15-20 wt % and a water-miscible organic solvent in a range from or any number in between 85-80 wt %. In some embodiments, the multi-component solvent comprises water in a range from or any number in between 20-25 wt % and a water-miscible organic solvent in a range from or any number in between 80-75 wt %. In some embodiments, the multi-component solvent comprises water in a range from or any number in between 25-30 wt % and a water-miscible organic solvent in a range from or any number in between 75-70 wt %. In some embodiments, the multi-component solvent comprises water in a range from or any number in between 30-35 wt % and a water-miscible organic solvent in a range from or any number in between 70-65 wt %. In some embodiments, the multi-component solvent comprises water in a range from or any number in between 35-40 wt % and a water-miscible organic solvent in a range from or any number in between 65-60 wt %. In some embodiments, the multi-component solvent comprises water in a range from or any number in between 40-45 wt % and a water-miscible organic solvent in a range from or any number in between 60-55 wt %. In some embodiments, the multi-component solvent comprises water in a range from or any number in between 45-50 wt % and a water-miscible organic solvent in a range from or any number in between 65-50 wt %. In some embodiments, the multi-component solvent comprises water in a range from or any number in between 50-55 wt % and a water-miscible organic solvent in a range from or any number in between 50-45 wt %. In some embodiments, the multi-component solvent comprises water in a range from or any number in between 55-60 wt % and a water-miscible organic solvent in a range from or any number in between 45-40 wt %. In some embodiments, the multi-component solvent comprises water in a range from or any number in between 60-65 wt % and a water-miscible organic solvent in a range from or any number in between 40-35 wt %. In some embodiments, the multi-component solvent comprises water in a range from or any number in between 65-70 wt % and a water-miscible organic solvent in a range from or any number in between 35-30 wt %. In some embodiments, the multi-component solvent comprises water in a range from or any number in between 70-75 wt % and a water-miscible organic solvent in a range from or any number in between 30-25 wt %. In some embodiments, the multi-component solvent comprises water in a range from or any number in between 75-80 wt % and a water-miscible organic solvent in a range from or any number in between 25-20 wt %. In some embodiments, the multi-component solvent comprises water in a range from or any number in between 80-85 wt % and a water-miscible organic solvent in a range from or any number in between 20-15 wt %. In some embodiments, the multi-component solvent comprises water in a range from or any number in between 85-90 wt % and a water-miscible organic solvent in a range from or any number in between 15-10 wt %. In some embodiments, the multi-component solvent comprises water in a range from or any number in between 90-95 wt % and a water-miscible organic solvent in a range from or any number in between 10-5 wt %. In some embodiments, the multi-component solvent comprises water in a range from or any number in between 95-99 wt % and a water-miscible organic solvent in a range from or any number in between 5-1 wt %.

More typically, the volume ratio of water to water-miscible organic solvent is typically in the range of from or any number in between 1:6 to 6:1 (v:v). In some embodiments, the volume ratio is from or any number in between 1:4 to 4:1 (v:v). In some embodiments, the volume ratio is from or any number in between 1:4 to 3:1 (v:v) water:water-miscible organic solvent. In other embodiments, the volume ratio is from or any number in between 1:4 to 1:3 (v:v) water:water miscible organic solvent. In certain embodiments, the volume ratio is 1:1 (v:v) water:water-miscible organic solvent.

Crystallization can be initiated using either temperature reduction (cooling) or solvent removal methods described above. When temperature reduction is used to initiate crystallization, the temperature of the crystallization solution is typically reduced from a first temperature that is typically in the range of from or any number in between 60° C. to 220° C., such as e.g., 60, 70, 80, 90, 100, 110, 120, 130, 140, 150, 160, 180, 190, 200, 210, or 220° C. or within a range defined by any two of the aforementioned temperatures. When water is a component of the crystallization solvent, the first temperature is often at the upper end of this range, e.g., in the range of from or any number in between 100° C. to 220° C. or in the range of from or any number in between 150° C. to 220° C. such as e.g., 100, 110, 120, 130, 140, 150, 160, 180, 190, 200, 210, or 220° C. or within a range defined by any two of the aforementioned temperatures. In some embodiments, the first temperature is in the range of from or any number in between 60° C. to 180° C., such as e.g., 60, 70, 80, 90, 100, 110, 120, 130, 140, 150, 160, or 180° C. or within a range defined by any two of the aforementioned temperatures to a second temperature that is lower than the first temperature. In other embodiments, the first temperature is in the range of from or any number in between 70° C. to 150° C., such as e.g., 70, 80, 90, 100, 110, 120, 130, 140, or 150° C. or within a range defined by any two of the aforementioned temperatures. When the crystallization solution is cooled, it is typically cooled to a second temperature that is below 60° C., such as e.g., equal to or less than 60, 50, 40, 30, 20, 10, 5, or 0° C. or within a range defined by any two of the aforementioned temperatures. More typically, it is cooled to a second temperature below 50° C. or below 40° C. such as, e.g., equal to or less than 50, 40, 30, 20, 10, 5, or 0° C. or within a range defined by any two of the aforementioned temperatures.

Crystallization can also be initiated by removing a first portion of the crystallization solvent from the crystallization solution to produce an FDCA pathway product slurry, wherein the FDCA pathway product slurry comprises a first plurality of FDCA pathway product crystals of different particle sizes and a second portion of the crystallization solvent; and separating the plurality of FDCA pathway product crystals from the second portion of the first crystallization solvent. The first plurality of FDCA pathway product crystals may be optionally dissolved in the same or different crystallization solvent, and the process repeated to obtain a second plurality of FDCA pathway product crystals of different particle sizes.

Seed crystals of the FDCA pathway product may be added to further promote the initiation of crystallization. Other additives, such as anti-foaming agents or crystallization aids, may be added to the crystallization solution to promote the crystallization process, and enable the formation of a suspension containing FDCA crystals. Anti-foaming agents that are suitable for use in the practice of the present disclosure include, for example, silicones, surfactants, phosphates, alcohols, glycols, stearates and the like. Additives such as surfactants or electrolyte polymers may also influence the morphology and composition of the crystals formed. See, e.g., U.S. Pat. Nos. 5,296,639 and 6,534,680, which are incorporated herein by reference in their entireties. Other additives may function as a flow improver to prevent agglomeration of the crystalline product on storage (see for example U.S. Pat. No. 6,534,680).

FDCA pathway product crystals produced by the processes described herein can be separated from the solution (mother liquor) by centrifugation, filtration, or other suitable process for separating solids from liquids. The crystals can then be washed and dried using any suitable process known to those having ordinary skill in the art.

The crystallization processes described herein can be carried out as part of an integrated process for preparing FDCA pathway product crystals from a raw feed that comprises the FDCA pathway product. The set of process steps can be carried out in at least a first crystallization zone, a dissolution zone, and a second (refined) crystallization zone. The crystallization processes can also be carried out as part of an integrated process for preparing FDCA pathway product crystals from an oxidation feedstock comprising the furanic oxidation substrate and the oxidation solvent. In this process, the integrated crystallization process is further integrated with the oxidation reaction processes described herein. In this integrated process, effluent from at least one oxidation reaction zone is passed, as feedstock, into the integrated crystallization process. In the crystallization processes described herein, crystal separation operations (such as the use of a centrifuge) may optionally be deployed after each crystallization zone (for example between the crystallization zone and the next dissolution zone). Illustrative integrated processes for producing a crystalline FDCA preparation are depicted in FIGS. 6-9.

Figure 6:
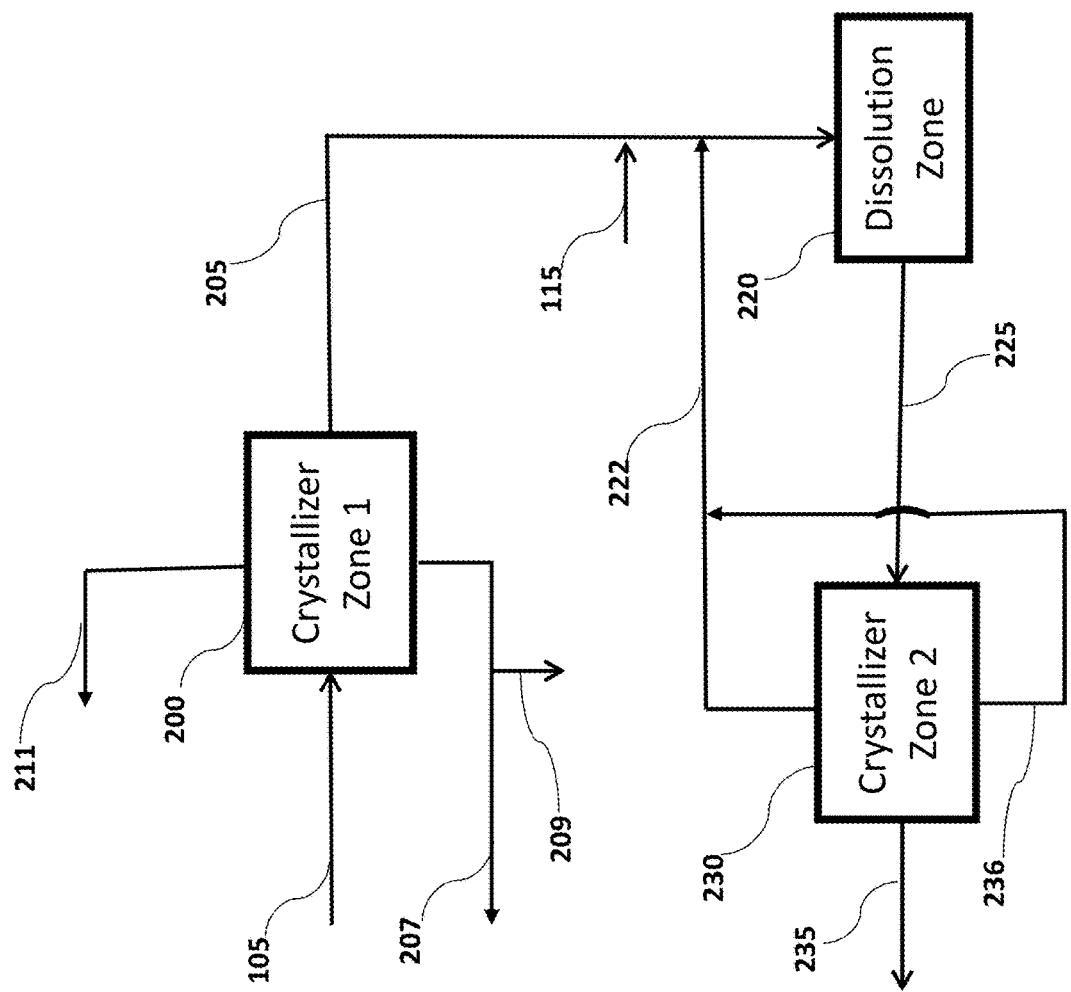
FIG. 6 depicts an integrated crystallization process for producing refined crystalline FDCA product from a feedstock that is the product stream of an oxidation reaction zone. The oxidation reaction zone product stream comprises FDCA and a multi-component solvent of water and a water-miscible light organic solvent. The process utilizes a solvent switch from the co-solvent to water between the first and second crystallization steps.

When the oxidation reaction zone product stream comprises a multi-component solvent that comprises water and a light organic solvent, the integrated process shown in FIG. 6 may be used. This process utilizes a solvent switch to water in the second (refined) crystallization zone. In this integrated process, an oxidation zone product stream 105 comprising water, a light organic solvent, and FDCA is passed into a first crystallization zone 200, to produce a solid crude FDCA crystal product stream 205, a water/light organic solvent vapor recycle stream 211 that is optionally recycled to an oxidation reaction zone, and a liquid water/light organic solvent recycle stream 207 that is also optionally recycled to an oxidation reaction zone. An optional purge stream 209 may be used to remove impurities from the liquid recycle stream 207. Solid crude FDCA crystal product stream 205 is fed into a dissolution zone 220 where solid crude FDCA crystal product is redissolved. Water 115 is fed into the solid crude FDCA crystal product stream 205 prior to passage of the latter into the dissolution zone 220 to produce a dissolution zone product stream 225 comprising solubilized FDCA in water. Dissolution zone product stream 225 is passed into a second (refined) crystallization zone 230 to produce a water vapor recycle stream 222, a liquid water recycle stream 236, and a refined crystallization product stream 235 that comprises refined FDCA crystals. Water vapor and liquid water recycle streams, 222 and 236, respectively, are both optionally fed into the solid crude FDCA crystal product stream 205.

Figure 7:
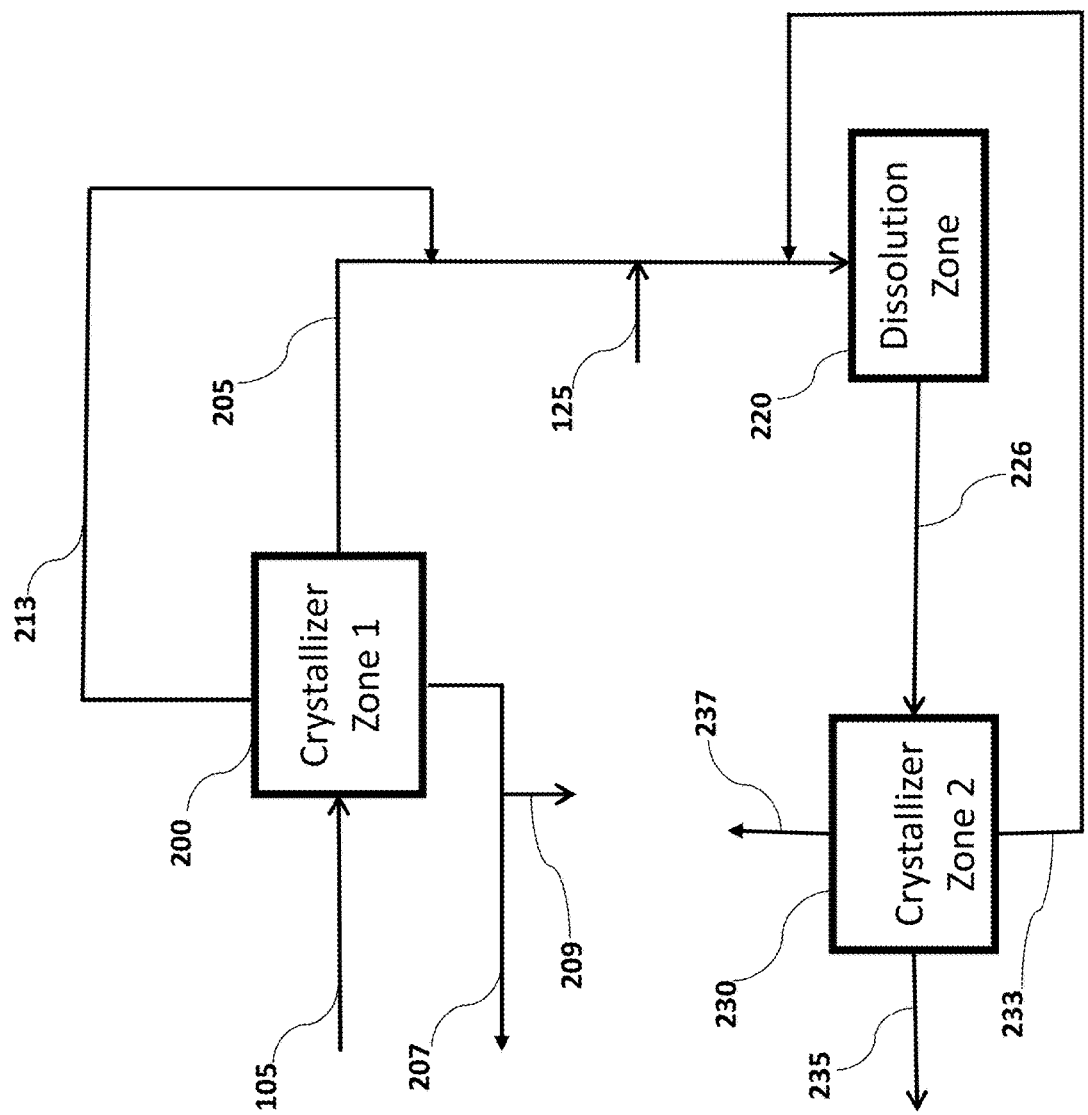
FIG. 7 depicts an integrated crystallization process for producing refined crystalline FDCA from a feedstock that is the product stream of an oxidation reaction zone. The process utilizes a multi-component solvent comprising water and a water-miscible light organic solvent.

When the oxidation reaction zone product stream comprises a multi-component solvent that comprises water and a light organic solvent, the integrated process shown in FIG. 7 may be used. In this integrated process, an oxidation zone product stream 105 comprising water, a light organic solvent, and FDCA is passed into a first crystallization zone 200, to produce crude FDCA crystal product stream 205, a water/light organic solvent vapor recycle stream 213 that is fed into the solid crude FDCA crystal product stream 205; and a water/light organic solvent liquid recycle stream 207 that is optionally recycled to an upstream oxidation reaction zone. An optional purge stream 209 may be used to remove impurities from the liquid recycle stream 207. Crude FDCA crystal product stream 205 is fed into a dissolution zone 220 where solid crude FDCA crystal product is redissolved. Make-up co-solvent (which may be water, the organic light solvent, or a solvent composition comprising both water and the light organic solvent) stream 125 is fed into the solid crude FDCA crystal product stream 205 prior to passage of the latter into the dissolution zone 220 to produce a dissolution zone product stream 226 comprising solubilized FDCA in the multi-component solvent. Dissolution zone product stream 226 is passed into a second (refined) crystallization zone 230 to produce a co-solvent vapor recycle stream 237, and a refined crystallization product stream 235 that comprises refined FDCA crystals. Co-solvent vapor recycle stream 237 is optionally recycled to the oxidation reaction zone. Co-solvent liquid recycle stream 233 is optionally fed into the solid crude FDCA crystal product stream 205.

Figure 8:
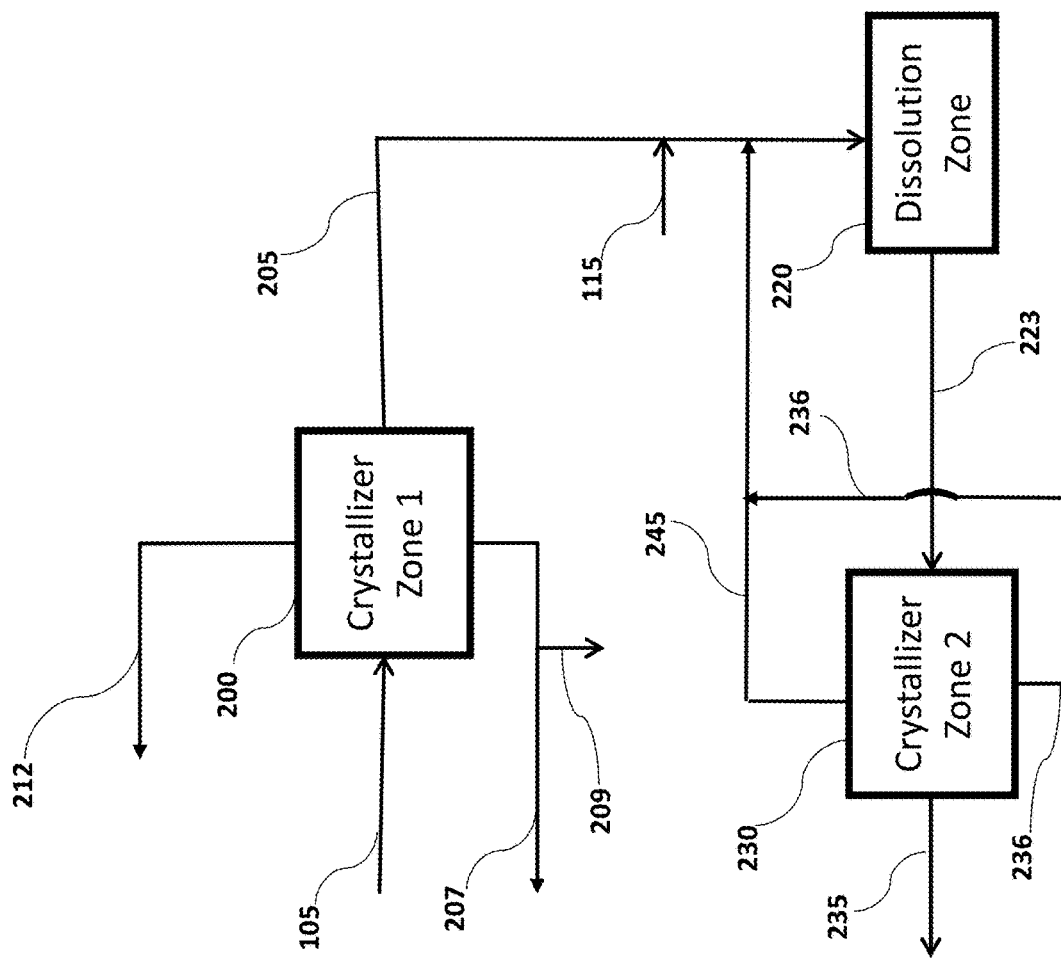
FIG. 8 depicts an integrated crystallization process for producing refined crystalline FDCA from a feedstock that is the product stream of an oxidation reaction zone. The oxidation reaction zone product stream comprises FDCA and a co-solvent of water and a water-miscible heavy organic solvent. The process utilizes a solvent switch from the co-solvent to water between the first and second crystallization steps.

In a further integrated process, when the oxidation reaction zone product stream comprises a multi-component solvent that comprises water and a heavy organic solvent, the process depicted in FIG. 8 may be used. This process utilizes a solvent switch to water in the second (refined) crystallization zone. In this integrated process, an oxidation zone product stream 105 comprising water, a heavy organic solvent, and FDCA is passed into a first crystallization zone 200, to produce a solid crude FDCA crystal product stream 205, a water vapor recycle stream 212 that is optionally recycled to an oxidation reaction zone, and a liquid water/heavy organic solvent recycle stream 207 that is also optionally recycled to an oxidation reaction zone. An optional purge stream 209 may be used to remove impurities from the liquid recycle stream 207. Solid crude FDCA crystal product stream 205 is fed into a dissolution zone 220 where solid crude FDCA crystal product is redissolved. Water stream 115 is fed into the solid crude FDCA crystal product stream 205 prior to passage of the latter into the dissolution zone 220 to produce a dissolution zone product stream 223 comprising solubilized FDCA in water. Dissolution zone product stream 223 is passed into a second (refined) crystallization zone 230 to produce a water vapor recycle stream 245, a liquid water recycle stream 236, and a refined crystallization product stream 235 that comprises refined FDCA crystals. Water vapor and liquid water recycle streams, 245 and 236, respectively, are both optionally fed into the solid crude FDCA crystal product stream 205.

Figure 9:
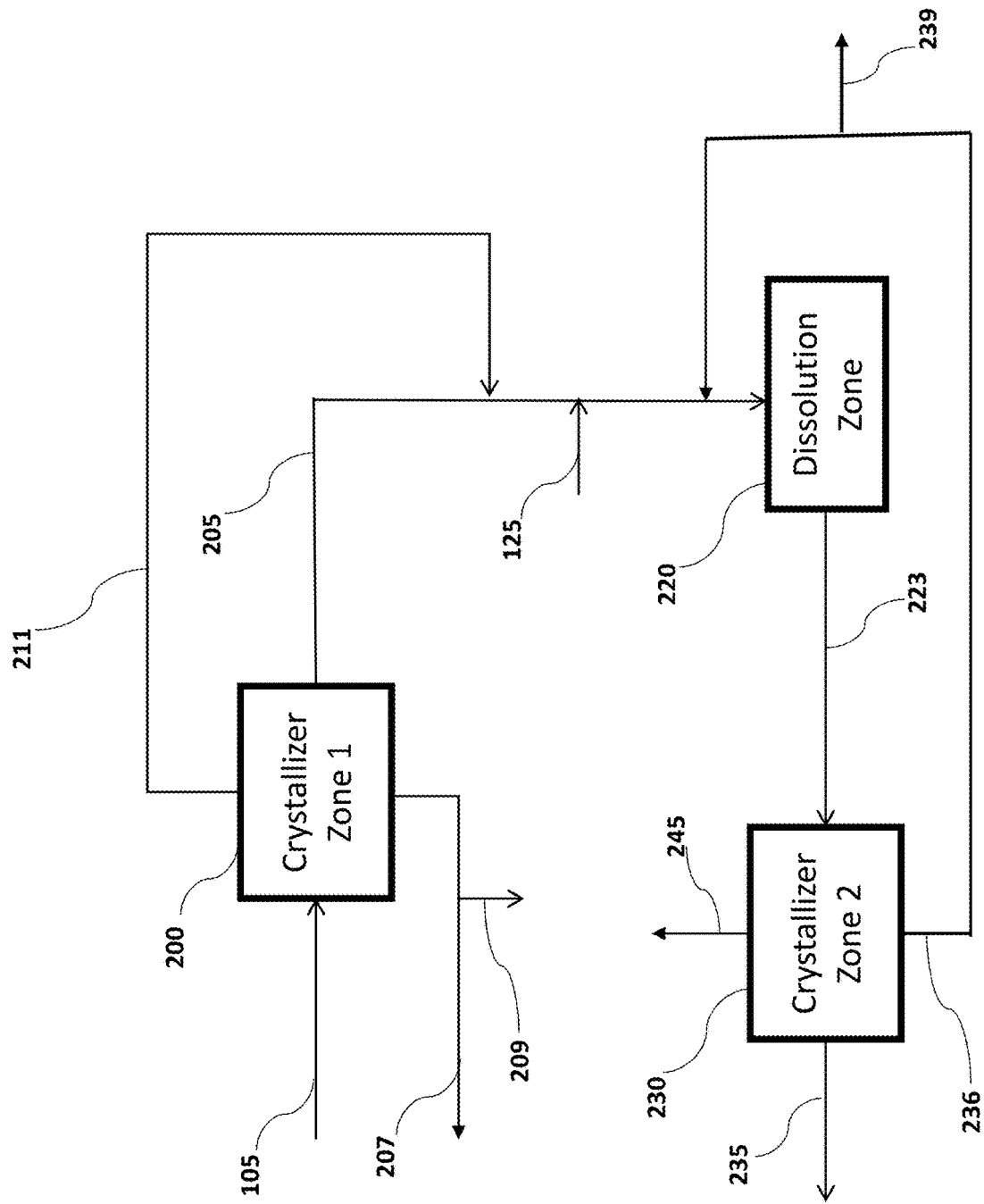
FIG. 9 depicts an integrated crystallization process for producing refined crystalline FDCA from a feedstock that is the product stream of an oxidation reaction zone. The oxidation reaction zone product stream comprises FDCA and a multi-component solvent of water and a water-miscible heavy organic solvent.

When the oxidation reaction zone product stream comprises a multi-component solvent (i.e., co-solvent) that comprises water and a heavy organic solvent, the integrated process shown in FIG. 9 may be used. In this integrated process, an oxidation zone product stream 105 comprising water, a heavy organic solvent, and FDCA is passed into a first crystallization zone 200, to produce a solid crude FDCA crystal product stream 205, a water vapor recycle stream 211 that is optionally passed into the solid crude FDCA crystal product stream 205, and a liquid water/heavy organic solvent recycle stream 207 that is optionally recycled upstream to an oxidation reaction zone. An optional purge stream 209 may be used to remove impurities from the liquid recycle stream 207. Solid crude FDCA crystal product stream 205 is fed into a dissolution zone 220 where solid crude FDCA crystal product is redissolved. Make up solvent stream 125 comprising water and heavy organic solvent is fed into the solid crude FDCA crystal product stream 205 prior to passage of the latter into the dissolution zone 220 to produce a dissolution zone product stream 223 comprising solubilized FDCA in water and heavy organic solvent. Dissolution zone product stream 223 is passed into a second (refined) crystallization zone 230 to produce a water vapor recycle stream 245, a liquid water/heavy organic solvent recycle stream 236, and a refined crystallization product stream 235 that comprises refined FDCA crystals. Water vapor stream 245 is optionally recycled upstream to an oxidation reaction zone. Liquid water/heavy organic solvent recycle stream 236 is optionally recycled to the solid crude FDCA crystal product stream 205. An optional purge stream 239 may be used to remove impurities from stream 236. The processes described herein are illustrative and variations to the processes are possible (e.g., process streams may be re-routed to alternative points in the processes) The crystalline product produced by the processes described herein exhibit desirable bulk properties. Thus, in a further embodiment, the present disclosure provides a crystalline FDCA composition comprising a plurality of FDCA crystals characterized by a distribution of particle sizes, wherein the distribution has a D50 in the range of from 50 μm up to 5000 μm. The crystalline FDCA preparation can be produced using the methods described above.

As used herein, the term "D50" refers to the median diameter of the particle size distribution. In some embodiments, the D50 is in the range of from or any number in between 50 μm to 2000 μm, or in the range of from or any number in between 100 μm to 3500 μm, and often in the range of from or any number in between 100 μm to 3000 μm. Typically the D50 of the particle size distribution is in the range of from or any number in between 100 μm to 750 μm, and more typically, the D50 in the range of from or any number in between 125 μm to 500 μm, and sometimes in the range of from or any number in between 125 μm to 450 μm, or from or any number in between 125 μm to 400 μm, and in some embodiments, in the range of from or any number in between 200 μm to 500 μm.

In some embodiments of the above, the crystalline FDCA preparation comprises less than 1 weight % FDCA crystals having a particle size less than 10 µm. In other embodiments, the crystalline FDCA preparation comprises less than 10 wt %, and more typically less than 9 wt %, less than 8 wt %, less than 7 wt %, less than 6 wt %, or less than 5 wt % FDCA crystals having a particle size less than 10 µm. In further embodiments, the crystalline FDCA preparations of the present disclosure typically comprise less than 10 wt %, less than 9 wt %, less than 8 wt %, less than 7 wt %, less than 6 wt %, less than 5 wt %, less than 4 wt %, less than 3 wt %, less than 2 wt %, or less than 1 wt % FDCA crystals having a particle size less than 4 µm.

Typically, the crystalline FDCA preparation comprises at least 98 wt % FDCA, and more typically, it comprises at least 99 wt % FDCA, and in some embodiments, it comprises greater than 99 wt % FDCA.

The crystallization processes of the present disclosure may be carried out using known industrial crystallizer systems that are suitable for carrying out solution phase crystallizations. Suitable systems include for example, batch crystallizers, continuous crystallizers (e.g., forced circulation crystallizers, draft-tube crystallizers, draft-tube-baffled crystallizers, or Oslo-type crystallizers, and the like), and other such crystallizer systems.

The crystalline FDCA preparations of the present disclosure are typically dry, and comprise less than 1 wt % water. Often, they comprise less than 0.9 wt %, or less than 0.8 wt %, or less than 0.7 wt %, or less than 0.6 wt %, or less than 0.5 wt %, or less than 0.4 wt %, or less than 0.3 wt %, or less than 0.2 wt % water or an amount of water that is within a range defined by any two of the aforementioned amounts.

In a further embodiment, the present disclosure provides a composition comprising FDCA and a multi-component solvent, wherein the multi-component solvent comprises water and a water-miscible aprotic organic solvent, and wherein the FDCA is present at a concentration of at least 5 wt %. In some embodiments, the FDCA is present at a concentration of at least 6 wt %, or at least 7 wt %, or at least 8 wt %, or at least 9 wt %, or at least 10 wt %, or at least 11 wt %, or at least 12 wt %, or at least 13 wt %, or at least 14 wt %, or at least 15 wt %. The composition comprising FDCA and a multi-component solvent can be a solution. The solution can contain FDCA that is solubilized such that the solution does not contain FDCA solids. The composition comprising FDCA and a multi-component solvent can be a solution (such that the solution does not contain FDCA solids) at room temperature or at a temperature up to 160° C. (such as e.g., 20, 30, 40, 50, 60, 70, 80, 90, 100, 110, 120, 130, 140, 150, or 160° C. or within a range defined by any two of the aforementioned temperatures). These compositions are useful in carrying out various unit operations that occur downstream of the oxidation step, including, for example, transesterification, polycondensation, or crystallization, and other downstream processes involved in the production of FDCA-based products. Typically, the water-miscible aprotic organic solvent is NMP or an ether, such as, for example, a glyme or dioxane.

In some embodiments, the water-miscible aprotic organic solvent species is at least 5 vol %, at least 10 vol %, at least 15 vol %, at least 20 vol %, at least 25 vol %, at least 30 vol %, at least 35 vol %, at least 40 vol %, at least 45 vol %, at least 50 vol %, at least 55 vol %, at least 60 vol %, at least 65 vol %, at least 70 vol %, at least 75 vol %, at least 80 vol %, at least 85 vol %, at least 90 vol %, or at least 95 vol % of the multi-component solvent system; and correspondingly, water is typically less than 95 vol %, less than 90 vol %, less than 85 vol %, less than 80 vol %, less than 75 vol %, less than 70 vol %, less than 65 vol %, less than 60 vol %, less than 55 vol %, less than 50 vol %, less than 45 vol %, less than 40 vol %, less than 35 vol %, less than 30 vol %, less than 25 vol %, less than 20 vol %, less than 15 vol %, less than 10 vol %, or less than 5 vol %, respectively, of the multi-component solvent or within a range defined by any two of the aforementioned amounts.

More typically, the volume ratio of water to water-miscible aprotic organic solvent is typically in the range of from 1:6 to 6:1. In some embodiments, the volume ratio is from 1:4 to 4:1 (v:v) or from 1:4 to 3:1 (v:v) water:water-miscible aprotic organic solvent In certain embodiments, the volume ratio is 1:1 (v:v) water:water-miscible aprotic organic solvent.

II. Catalyst Preparation

Heterogeneous oxidation catalysts employed in the processes described herein may be prepared by any one of a number of methods. For example, noble metals can be deposited onto the exterior and interior surfaces of the support material using methods such as, for example, incipient wetness, ion exchange, deposition-precipitation, and/or vacuum impregnation. When more than one metal is deposited onto the support, they may be deposited sequentially or simultaneously. After depositing the metals onto the surfaces of the catalyst support, the catalyst is typically dried at a temperature in the range of 20° C. to 120° C. (such as e.g., 20, 30, 40, 50, 60, 70, 80, 90, 100, 110, or 120° C. or within a range defined by any two of the aforementioned temperatures for a period of time that is in the range of from one hour up to twenty four hours e.g., 1, 2, 3, 4, 5, 6, 7, 8, 9, 10, 11, 12, 13, 14, 15, 16, 17, 18, 19, 20, 21, 22, 23, or 24 hours or within a range defined by any two of the aforementioned time periods. The catalyst can be dried under sub-atmospheric pressure conditions. In some embodiments, the catalyst is reduced after drying (e.g., by flowing 5% $H_2$ in $N_2$ at a temperature of at least 200° C. for a period of time (e.g., at least three hours). The catalyst may also be calcined in air at a temperature of at least 200° C. for a period of time of at least three hours.

When the heterogeneous oxidation catalyst comprises gold, the gold may be added to the support material as a solubilized constituent in a liquid. When the gold-liquid solution is mixed with the support material, a suspension of support material in the solubilized gold-containing liquid phase is formed. In this method, a base is then added to the suspension in order to form a precipitant of insoluble gold complex which deposits on the surfaces of the support material in a uniform fashion. In this deposition method, the solubilized gold constituent may be in the form of a gold salt (e.g., $HAuCl_4$, and the like). Although any base that can promote the formation of the insoluble gold complex is suitable, bases such as potassium hydroxide (KOH) and sodium hydroxide (NaOH), are typically employed. The resulting solids may be collected by known methods for separating solids from liquids, including, for example, filtration, centrifugation, and the like. The collected solids may be optionally washed, then optionally heated to dry. Heating may also be employed to reduce the gold complex on the support to gold (0). Heating may be conducted at temperatures in the range of from 60° C. to dry, and from 150° C. for reduction up to 500° C., at which temperature the gold can be effectively reduced (such as e.g., 60, 70, 80, 90, 100, 110, 120, 130, 140, 150, 160, 180, 190, 200, 210, 220, 230, 240, 250, 300, 350, 400, 450, or 500° C. or within a range defined by any two of the aforementioned temperatures). In various embodiments, the heating step may be conducted in the presence of a reducing atmosphere in order to promote the reduction of the complex to deposit the gold onto the support as gold (0). The duration of heating may vary from a few hours to a few days depending on various factors, including, for example, the objective of the heating step and the decomposition rate of the base which is added to form the insoluble complex. Typically, the heating time for the purpose of drying is in the range of from 2 to 24 hours (e.g., 2, 3, 4, 5, 6, 7, 8, 9, 10, 11, 12, 13, 14, 15, 16, 17, 18, 19, 20, 21, 22, 23, or 24 hours or within a range defined by any two of the aforementioned time periods), and for reducing the gold complex, in the range of from 1 to 4 hours (e.g., 1, 2, 3, or 4 hours or within a range defined by any two of the aforementioned time periods).

When the heterogeneous oxidation catalyst comprises platinum, the platinum is typically added to the support material by contacting the support material with a solution containing a soluble platinum precursor compound or with a platinum-containing colloid. Platinum may be deposited on the support material in the form of any one of a variety of compounds, such as, for example, platinum (II) nitrate, platinum (IV) nitrate, platinum oxynitrate, platinum (II) acetylacetonate (acac), tetraamineplatinum (II) nitrate, tetraamineplatinum (II) hydrogenphosphate, tetraamineplatinum (II) nitrate, tetraamineplatinum (II) hydrogenphosphate, tetraamineplatinum (II) nitrate, tetraamineplatinum (II) hydrogenphosphate, tetraamineplatinum (II) hydrogencarbonate, tetraamineplatinum (II) hydroxide, $H_2PtCl_6$, $PtCl_4$, $Na_2PtCl_4$, $K_2PtCl_4$, $(NH_4)_2PtCl_4$, $Pt(NH_3)_4Cl_2$, mixed $Pt(NH_2)_xCl_y$, $K_2Pt(OH)_6$, $Na_2Pt(OH)_6$, $(NMe_4)_2Pt(OH)_6$, and $[(C_2H_7NO)_2]Pt(OH)_6$, and the like. Typically, platinum is added to the support material as platinum (II) nitrate, platinum (IV) nitrate, platinum (II) acetylacetonate (acac), tetraamine platinum (II) hydroxide, $K_2PtCl_4$, or $K_2Pt(OH)_6$.

If a gold- and platinum-containing heterogeneous oxidation catalyst is desired, the platinum can be deposited onto the surfaces of the support material either before or after gold has been deposited, or alternatively, the platinum and gold can be deposited together. When platinum is added to a gold-containing heterogeneous oxidation catalyst, it can be added after deposition of the gold, and either before or after drying or after drying, and before or after reduction of the gold. When platinum is added to the catalyst support prior to the deposition of gold, the platinum employed is one which will not be re-dissolved upon addition of the base used to promote the deposition of gold onto the support.

After the platinum compound is added to the support material, the resulting platinum-containing support material is dried. Drying may be conducted at room temperature or at a temperature up to 120° C. (such as e.g., 20, 30, 40, 50, 60, 70, 80, 90, 100, 110, or 120, ° C. or within a range defined by any two of the aforementioned temperatures. Typically, drying is conducted at a temperature in the range of or any number in between 40° C. to 80° C., and often at a temperature of 60° C. (such as e.g., 40, 50, 60, 70, or 80° C. or within a range defined by any two of the aforementioned temperatures. Drying typically proceeds over a period of time in the range of from a few minutes to a few hours. Typically, the platinum-containing support material is dried over a period of time in the range of from or any number in between 6 hours to 24 hours (e.g., 6, 7, 8, 9, 10, 11, 12, 13, 14, 15, 16, 17, 18, 19, 20, 21, 22, 23, or 24 hours or within a range defined by any two of the aforementioned time periods). The drying can be conducted with a continuous or a staged temperature increase of from or any number in between 60° C. to 120° C. (such as e.g., 60, 70, 80, 90, 100, 110, or 120, ° C. or within a range defined by any two of the aforementioned temperatures) on a band calciner or belt dryer.

After drying the platinum-containing support material, the material is subjected to at least one thermal treatment in order to reduce the platinum (which is deposited as platinum (II) or platinum (IV)) to platinum (0). In certain embodiments, the thermal treatment(s) may be conducted under a forming gas atmosphere. Alternatively, a liquid reducing agent may be employed to reduce the platinum. For example, hydrazine or formaldehyde or formic acid or a salt thereof (e.g., sodium formate) or $NaH_2PO_2$ may be employed to effect the reduction of platinum.

The temperature(s) at which the thermal treatment(s) is (are) typically conducted in the range of from or any number in between 150° C. to 600° C. (such as e.g., 150, 200, 250, 300, 350, 400, 450, 500, 550, or 600° C. or within a range defined by any two of the aforementioned temperatures). In some embodiments, the temperatures of the thermal treatment(s) is (are) in the range of from or any number in between 200° C. to 500° C., and, more typically, in the range of from or any number in between 200° C. to 400° C. (such as e.g., 200, 250, 300, 350, or 400° C. or within a range defined by any two of the aforementioned temperatures). The thermal treatment is typically conducted for a period of time in the range of from or any number in between 1 hour to 8 hours or in some embodiments, in the range of from or any number in between 1 hour to 3 hours (e.g., 1, 2, 3, 4, 5, 6, 7, or 8 or within a range defined by any two of the aforementioned time periods).

III. Preparation of FDCA Derivatives and FDCA Polymers

Derivatives of FDCA can be readily prepared from the FDCA produced using the processes of the present disclosure. For example, in some embodiments, it may be desirable to further convert the FDCA pathway product(s) to an FDCA salt (e.g., by adding a base, such as, for example, sodium hydroxide, potassium hydroxide, sodium hydroxide, ammonia, and the like), an ester, an amide, a halide, and the like.

The dicarboxylic acid functionality of the FDCA makes it useful as a monomer, either as is or in derivatized form. FDCA derivatives that are useful as monomers for further polymerization, include FDCA esters, FDCA amides, FDCA halides, and the like. The resulting FDCA derivatives may be optionally purified by, for example, distillation, crystallization, and the like.

In one embodiment, the present disclosure provides a process for converting the FDCA to an ester of FDCA, the converting step comprising contacting the FDCA produced by the processes of the present disclosure with an alcohol under conditions sufficient to produce a corresponding FDCA monoester or FDCA diester. Alcohols suitable for use in the practice of the present disclosure include branched or unbranched, $C_1$-$C_{20}$ alcohols (e.g., aliphatic alcohols or aromatic $C_5$-$C_{20}$ alcohols and including, for example, diols or polyols). In some embodiments, the alcohol is a branched or unbranched, $C_1$-$C_{10}$ alcohol, $C_1$-$C_6$ alcohol, or a branched or unbranched, $C_1$-$C_4$ (i.e., methyl alcohol, ethyl alcohol, n-propyl alcohol, iso-propyl alcohol, 2-methylpropan-1-ol (i.e., isobutyl alcohol), 2-methyl-2-propanol (i.e., t-butyl alcohol), or n-butyl, and the like. $C_1$-$C_{12}$ polyols, including diols and other polyols, are also suitable for use in these processes. These include, for example, ethanediol (ethylene glycol), 1,3-propanediol, 1,4-butanediol, 2,3-butanediol, a hexanediol (e.g., 1,6-hexanediol, 1,2-hexanediol, 1,5-hexanediol, 2,5-hexanediol, and the like), a hexanetriol (e.g., 1,2,6-hexanetriol, 1,2,3-hexanetriol, 1,3,6-hexanetriol, and the like), bis(hydroxymethyl)benzene, 1,8-octanediol, 4-octene-1,8-diol, 1,9-nonanediol, 2-nonene-1,4-diol, 7-nonene-1,5-diol, 7-nonene-1,5-diol, 1,10-decanediol, or 1,12-dodecanediol, and the like, as well as any combination thereof. Conditions sufficient for promoting the formation of a mono- or di-ester of FDCA (i.e., "esterifying conditions") include, for example, contacting the FDCA with the desired alcohol in the presence of a catalyst, such as, for example, a mineral acid (such as, for example, HCl, or $H_2SO_4$, and the like) at a temperature in the range of from 50° C. to 150° C. (such as e.g., 50, 60, 70, 80, 90, 100, 110, 120, 130, 140, or 150° C. or within a range defined by any two of the aforementioned temperatures). Often, the alcohol is methanol and the ester of FDCA is the methyl ester of FDCA, and typically, it is the dimethyl ester of FDCA. In other embodiments, the alcohol is ethanol, and the ester of FDCA is the ethyl ester of FDCA, and typically, it is the diethyl ester of FDCA.

Figure 10:
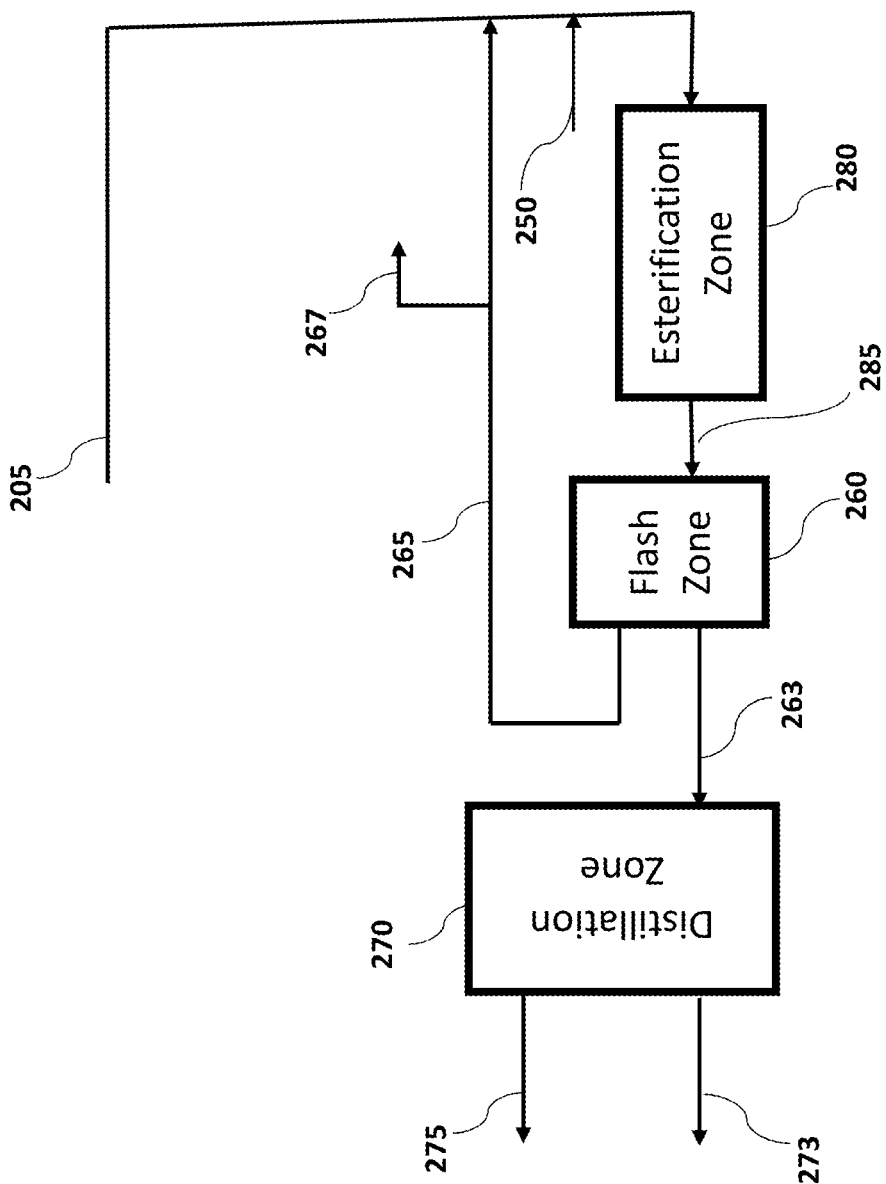
FIG. 10 depicts an integrated process for producing a purified dimethylester of FDCA by distillation.

An illustrative integrated process for producing purified dimethyl ester of FDCA by distillation is provided in FIG. 10. With reference to FIG. 10, a solid crude FDCA feedstock stream 205 is mixed with a methanol stream 250 and optionally a methanol/water vapor stream 265 prior to being passed into an esterification zone 280 where FDCA and methanol are subjected to conditions that promote esterification to produce an esterification zone product stream 285, which comprises the dimethyl ester of FDCA. Esterification zone product stream 285 is passed into a flash distillation zone, which comprises a flash distillation column, to produce a methanol/water vapor recycle stream 265 and a flash zone product stream 263 which comprises the dimethyl ester of FDCA. A portion of the water produced in the esterification zone may be removed from the methanol/water vapor recycle stream 265 in a water vapor purge stream 267. The methanol or methanol/water vapor recycle stream 265 is recycled to the FDCA feedstock stream 205. The flash zone product stream 263 is passed into a distillation column zone 270 to product an impurity stream 273 and a light stream 275 comprising purified dimethyl ester of FDCA.

Figure 11:
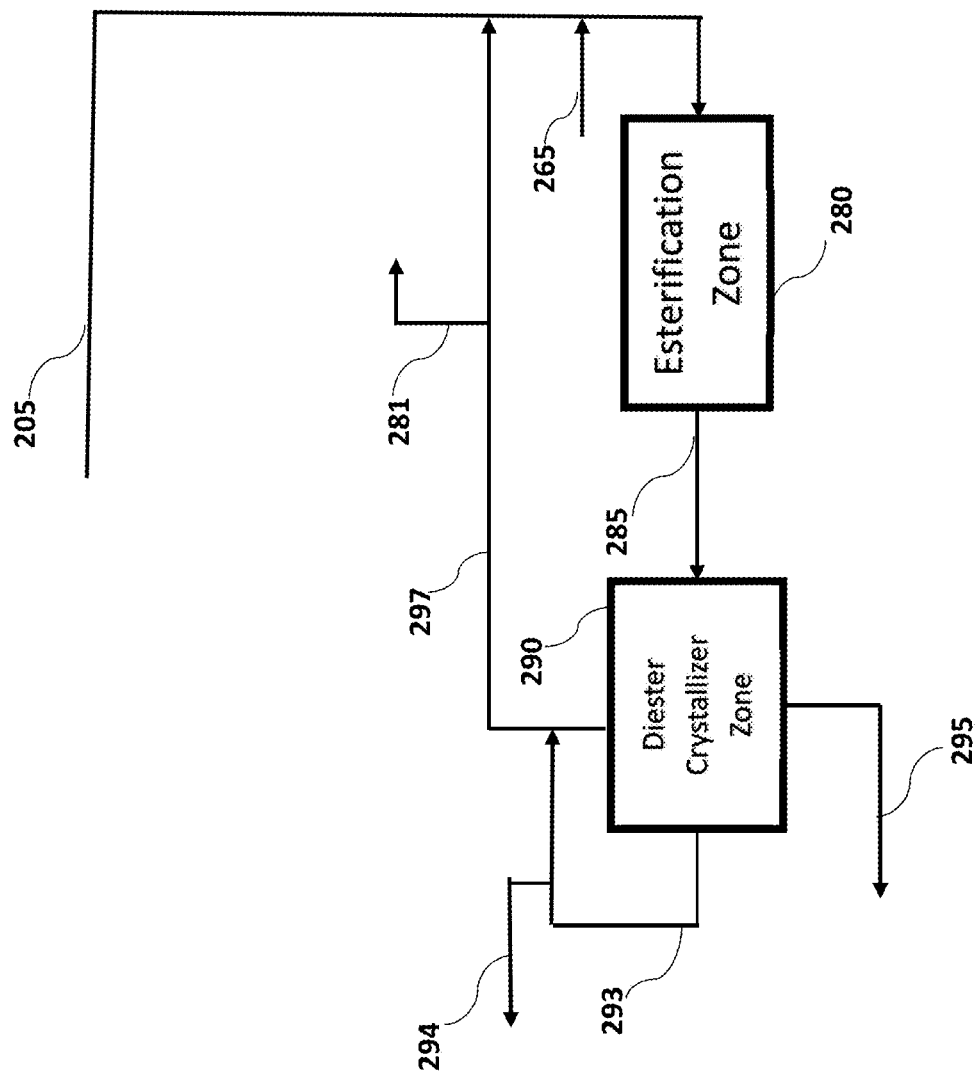
FIG. 11 depicts an integrated process for producing a purified dimethylester of FDCA by crystallization.

An alternative integrated process for producing purified dimethyl ester of FDCA that utilizes crystallization as the purification step is provided in FIG. 11. In this process, a solid crude FDCA feedstock stream 205 is mixed with a methanol make up stream 265 and optionally a vapor methanol/water stream 297 and subsequently passed into an esterification zone 280 where FDCA and methanol are subjected to conditions that promote esterification to produce an esterification zone product stream 285, which comprises the dimethyl ester of FDCA. Esterificaton zone product stream 285 is passed into a diester crystallizer zone 290, to produce a diester crystallizer zone product stream 295 that comprises the dimethyl ester of FDCA in crystalline form, a liquid recycle stream 293 that comprises methanol and water, and a vapor methanol/water stream 297. Liquid recycle stream 293 is passed into the vapor methanol/water stream 297. A portion of the water in the vapor methanol/water stream 297 may be removed in a water vapor purge stream 281. Optional purge stream 294 facilitates removal of impurity components from the vapor methanol/water stream 293.

In a another embodiment, the present disclosure provides a process for converting the FDCA or an FDCA ester to an FDCA amide, wherein the converting step comprises contacting the FDCA or FDCA ester produced by the processes of the present disclosure with an amino-substituted compound under conditions sufficient to produce a corresponding FDCA mono-amide or FDCA diamide. Conditions sufficient for promoting the formation of the mono- or di-amide of FDCA (i.e., amidation conditions") include, for example, contacting the FDCA or FDCA ester with the amine under conditions that are known to convert carboxylic acids or esters into amides. See, e.g., March's Advanced Organic Chemistry Eds. M. B. Smith and J. March; Wiley (2013), which is incorporated herein by reference. Amino-substituted compounds suitable for use in the practice of the present disclosure include, for example, $C_1$-$C_{20}$ aliphatic or aromatic amines. Typically, the amino-substituted compound is a $C_1$-$C_{10}$, or $C_1$-$C_6$ mono- or di-amine. Suitable amino-substituted compounds include, for example, 1,6-hexamethylenediamine, 1,5-pentamethylenediamine or 1,4-tetramethylenediamine, and the like.

In a further embodiment, the present disclosure provides a process for converting the FDCA to an FDCA halide, the converting step comprising contacting the FDCA produced by the processes of the present disclosure with a halogenating agent (e.g. $SOCl_2$) under conditions that are known to convert carboxylic acids into acyl halides. See for example March's Advanced Organic Chemistry Eds. M. B. Smith and J. March; Wiley (2013), which is incorporated herein by reference in its entirety.

Certain FDCA derivatives may be employed as FDCA-monomers, which are useful for producing polymers, such as, for example, polyesters, polyamides, and the like. As used herein, the term "FDCA-based monomers" refers to FDCA, as well as FDCA derivatives that have the ability to react with other monomers to form a polymer. Thus, in a further embodiment, the present disclosure provides a process for producing an FDCA-based polymer, the method comprising polymerizing an FDCA-based monomer of the present disclosure under conditions sufficient to produce the FDCA-based polymer. In some embodiments, the FDCA-based monomer is an FDCA derivative selected from the group consisting of an FDCA ester (i.e., a monoester or diester), an FDCA amide (i.e., an FDCA monoamide or an FDCA diamide), and an FDCA halide (e.g., an FDCA monochloride, an FDCA dichloride, and the like), and the like. In certain embodiments, the FDCA-based monomer is polymerized with a second monomer that is not the same as the first monomer. Second monomers that are suitable for use in the practice of the present disclosure include a polyol that has at least two hydroxyl groups.

Exemplary polyols that can be used as a suitable co-monomer include ethanediol (ethylene glycol), 1,3-propanediol, 1,4-butanediol, 2,3-butanediol, a hexanediol (e.g., 1,6-hexanediol, 1,2-hexanediol, 1,5-hexanediol, 2,5-hexanediol, and the like), a hexanetriol (e.g., 1,2,6-hexanetriol, 1,2,3-hexanetriol, 1,3,6-hexanetriol, and the like), bis(hydroxymethyl)benzene, 1,8-octanediol, 4-octene-1,8-diol, 1,9-nonanediol, 2-nonene-1,4-diol, 7-nonene-1,5-diol, 7-nonene-1,5-diol, 1,10-decanediol, or 1,12-dodecanediol, and the like, as well as any combination thereof. Typically, the polyol is a diol. Exemplary dicarboxylic acids include, for example, succinic acid, or adipic acid, and the like. Exemplary hydroxyacids include, for example, lactic acid, succinic acid, malic acid, salicylic acid, syringic acid, or ferulic acid, and the like. Exemplary sugar alcohols include, for example, isosorbide, isomannide, or isoidide, and the like. Typically, the FDCA-based monomer is selected from the group consisting of FDCA and dimethyl FDCA ester and a second monomer is employed that is a polyol.

When the FDCA-based monomer is FDCA, the second monomer can be an aliphatic or aromatic diamine or an aliphatic or aromatic polyol (e.g., a diol, or a triol, and the like). Suitable diamines include, for example, 1,6-hexamethylenediamine, 1,5-pentamethylenediamine, or 1,4-tetramethylenediamine, and the like. Suitable polyols include those described above.

The FDCA-based polymers of the present disclosure are typically produced using a polycondensation reaction, either in a solution polymerization or melt polymerization. In some embodiments, the polymerization step is preceded by a transesterification step. The polycondensation reactions are typically carried out in the presence of a catalyst, such as, for example, dibutyltin (IV) oxide, titanium (IV) isopropoxide, antimony (III) oxide (see, e.g., G.-J. M. Gruter, et al., *Comb. Chem. High Throughput Screening* (2012) 15:180-188, which is incorporated herein by reference.

In a specific embodiment, the present disclosure provides a method for producing an FDCA-based polyester, the method comprising contacting an FDCA-monomer selected from the group consisting of FDCA and FDCA dimethyl ester with a $C_1$-$C_{20}$ polyol at a temperature in the range of from 120° C. to 225° C. (such as e.g., 120, 130, 140, 150, 160, 180, 190, 200, 210, or 225° C. or within a range defined by any two of the aforementioned temperatures) to form a reaction mixture for producing the corresponding dihydroxy $C_1$-$C_{20}$ FDCA ester (in an esterification or transesterification step, respectively), then increasing the temperature of the reaction mixture to a temperature in the range of from 180° C. to 250° C. (such as e.g., 180, 190, 200, 210, 220, 230, 240, or 250° C. or within a range defined by any two of the aforementioned temperatures) to produce the corresponding FDCA-based polyester (in a polycondensation step). Typically, the $C_1$-$C_{20}$ FDCA polyol is a diol selected from the group consisting of ethylene glycol, 1,3-propanediol, 1,4-butanediol, 2,3-butanediol, and 1,6-hexanediol. In certain embodiments the molecular weight of the resultant polyester can be further increased by a third stage solid state polymerization in which the polymeric material (in the form of pellets, granules, flakes or chips and the like) is subjected to a certain amount of time, such as 1-24 hours (e.g., 1, 2, 3, 4, 5, 6, 7, 8, 9, 10, 11, 12, 13, 14, 15, 16, 17, 18, 19, 20, 21, 22, 23, or 24 hours or within a range defined by any two of the aforementioned time periods)) at elevated temperatures above the glass transition temperature and below the melting temperature of the polyester. The polycondensation methods are typically conducted at pressures below 1 atmosphere.

IV. Production of Furanic Oxidation Substrate

While furanic oxidation substrate material can be readily purchased, it may be desirable in certain circumstances to produce the furanic oxidation substrate. The present disclosure provides a process for producing a furanic oxidation substrate, the process comprising:
(a°) contacting a carbohydrate feedstock comprising a sugar and a dehydration solvent with a catalyst under conditions sufficient to form a (dehydration) reaction mixture for dehydrating the sugar to produce the furanic oxidation substrate (referred to herein as the "dehydration process"). Typically, the sugar is a hexose, such as, for example, glucose, galactose, mannose, idose, a ketohexose, fructose, levulose, sorbose, tagatose, or allose, and the like. Usually, the sugar is glucose or fructose. Often, the sugar is fructose.

The term "dehydration solvent" refers to a solvent in which both the sugar and the furanic oxidation substrate are each separately soluble at a minimum level of at least 2% by weight at the temperature at which the dehydration reaction is carried out. Typically, the dehydration solvent is one in which the furanic oxidation substrate has a solubility of at least 3 wt %, at least 4 wt %, at least 5 wt %, at least 6 wt %, at least 7 wt %, at least 8 wt %, at least 9 wt %, at least 10 wt %, at least 11 wt %, at least 12 wt %, at least 13 wt %, at least 14 wt %, at least 15 wt %, at least 17%, at least 19%, at least 21%, at least 23%, or at least 25% as measured at the temperature at which the dehydration reaction is carried out. In some embodiments, the concentration of furanic oxidation substrate in the dehydration solvent ranges from or any number in between 2-4 wt %, 3-5 wt %, 4-6 wt %, 5-7 wt %, 6-8 wt %, 7-9 wt %, 8-10 wt %, 9-11 wt %, 10-12 wt %, 11-13 wt %, 12-14 wt %, 13-15 wt %, 14-16 wt %, 15-17 wt %, 16-18 wt %, 17-19 wt %, 18-20 wt %, 19-21 wt %, 20-22 wt %, 21-23 wt %, 22-24 wt %, or 23-25 wt % or within a range defined by any of two of the aforementioned weight percentages. Typically, the dehydration solvent comprises water and/or a water-miscible organic solvent. More typically, the dehydration solvent is a multi-component solvent. Usually, the multi-component solvent employed in the dehydration process comprises water and a water-miscible aprotic organic solvent. Water-miscible aprotic organic solvents and multi-component solvent compositions that are suitable for use in the dehydration process are the same as those that are suitable for use in the FDCA pathway product-generating processes as described hereinabove. In some embodiments, the water-miscible aprotic organic solvent is N-Methyl-2-Pyrrolidone (NMP). In some embodiments, the carbohydrate feedstock comprises fructose and the furanic oxidation substrate comprises HMF.

Exemplary water-miscible aprotic solvents suitable for use in dehydration solvent include tetrahydrofuran, a glyme, dioxane, a dioxolane, dimethylformamide, dimethylsulfoxide, sulfolane, acetone, N-methyl-2-pyrrolidone ("NMP"), methyl ethyl ketone ("MEK"), gamma-valerolactone, and the like. Preferably, the water-miscible aprotic organic solvent is an ether, such as, for example, a glyme, dioxane (1,4-dioxane), a dioxolane (e.g., 1,3-dioxolane), tetrahydrofuran, and the like. Glymes that are suitable for use in the practice of the present disclosure include, for example, monoglyme (1,2-dimethoxyethane, "DME"), ethyl glyme, diglyme (diethylene glycol dimethyl ether), ethyl diglyme, triglyme, butyl diglyme, tetraglyme, a polyglyme, a highly ethoxylated diether of a high molecular weight alcohol ("higlyme"), and the like. Often, the dehydration solvent is a multi-component solvent comprising water and a water-miscible aprotic organic solvent that is glyme, diglyme, or dioxane.

In some embodiments, the water-miscible organic solvent species is at least 5 volume % (vol %), at least 10 vol %, at least 15 vol %, at least 20 vol %, at least 25 vol %, at least 30 vol %, at least 35 vol %, at least 40 vol %, at least 45 vol %, at least 50 vol %, at least 55 vol %, at least 60 vol %, at least 65 vol %, at least 70 vol %, at least 75 vol %, at least 80 vol %, at least 85 vol %, at least 90 vol %, or at least 95 vol % of the multi-component solvent; and correspondingly, water is typically less than 95 vol %, less than 90 vol %, less than 85 vol %, less than 80 vol %, less than 75 vol %, less than 70 vol %, less than 65 vol %, less than 60 vol %, less than 55 vol %, less than 50 vol %, less than 45 vol %, less than 40 vol %, less than 35 vol %, less than 30 vol %, less than 25 vol %, less than 20 vol %, less than 15 vol %, less than 10 vol %, or less than 5 vol %, respectively, of the multi-component system.

In some embodiments, the multi-component solvent comprises water in a range from or any number in between 1-5 wt % and a water-miscible organic solvent in a range from or any number in between 99-95 wt %. In some embodiments, the multi-component solvent comprises water in a range from or any number in between 5-10 wt % and a water-miscible organic solvent in a range from or any number in between 95-90 wt %. In some embodiments, the multi-component solvent comprises water in a range from or any number in between 10-15 wt % and a water-miscible organic solvent in a range from or any number in between 90-85 wt %. In some embodiments, the multi-component solvent comprises water in a range from or any number in between 15-20 wt % and a water-miscible organic solvent in a range from or any number in between 85-80 wt %. In some embodiments, the multi-component solvent comprises water in a range from or any number in between 20-25 wt % and a water-miscible organic solvent in a range from or any number in between 80-75 wt %. In some embodiments, the multi-component solvent comprises water in a range from or any number in between 25-30 wt % and a water-miscible organic solvent in a range from or any number in between 75-70 wt %. In some embodiments, the multi-component solvent comprises water in a range from or any number in between 30-35 wt % and a water-miscible organic solvent in a range from or any number in between 70-65 wt %. In some embodiments, the multi-component solvent comprises water in a range from or any number in between 35-40 wt % and a water-miscible organic solvent in a range from or any number in between 65-60 wt %. In some embodiments, the multi-component solvent comprises water in a range from or any number in between 40-45 wt % and a water-miscible organic solvent in a range from or any number in between 60-55 wt %. In some embodiments, the multi-component solvent comprises water in a range from or any number in between 45-50 wt % and a water-miscible organic solvent in a range from or any number in between 65-50 wt %. In some embodiments, the multi-component solvent comprises water in a range from or any number in between 50-55 wt % and a water-miscible organic solvent in a range from or any number in between 50-45 wt %. In some embodiments, the multi-component solvent comprises water in a range from or any number in between 55-60 wt % and a water-miscible organic solvent in a range from or any number in between 45-40 wt %. In some embodiments, the multi-component solvent comprises water in a range from or any number in between 60-65 wt % and a water-miscible organic solvent in a range from or any number in between 40-35 wt %. In some embodiments, the multi-component solvent comprises water in a range from or any number in between 65-70 wt % and a water-miscible organic solvent in a range from or any number in between 35-30 wt %. In some embodiments, the multi-component solvent comprises water in a range from or any number in between 70-75 wt % and a water-miscible organic solvent in a range from or any number in between 30-25 wt %. In some embodiments, the multi-component solvent comprises water in a range from or any number in between 75-80 wt % and a water-miscible organic solvent in a range from or any number in between 25-20 wt %. In some embodiments, the multi-component solvent comprises water in a range from or any number in between 80-85 wt % and a water-miscible organic solvent in a range from or any number in between 20-15 wt %. In some embodiments, the multi-component solvent comprises water in a range from or any number in between 85-90 wt % and a water-miscible organic solvent in a range from or any number in between 15-10 wt %. In some embodiments, the multi-component solvent comprises water in a range from or any number in between 90-95 wt % and a water-miscible organic solvent in a range from or any number in between 10-5 wt %. In some embodiments, the multi-component solvent comprises water in a range from or any number in between 95-99 wt % and a water-miscible organic solvent in a range from or any number in between 5-1 wt %.

In some embodiments, the volume ratio of water to water-miscible organic solvent is in the range from or any number in between 1:6 to 6:1. In certain embodiments, the volume ratio is from or any number in between 1:4 to 4:1 water:water-miscible organic solvent. In other embodiments, the volume ratio is from or any number in between 1:4 to 3:1 water:water miscible organic solvent. In other embodiments, the volume ratio is from or any number in between 1:3 to 3:1 water:water miscible organic solvent. In certain embodiments, the volume ratio is 1:1 water:water-miscible organic solvent.

In some embodiments, the multi-component solvent comprises water and two different water-miscible organic solvents. Typically both of the water-miscible organic solvents are water-miscible aprotic organic solvents. Each of the two water-miscible aprotic solvents can be independently selected from the group of tetrahydrofuran, a glyme, a dioxane, a dioxolane, dimethylformamide, dimethylsulfoxide, sulfolane, acetone, N-methyl-2-pyrrolidone ("NMP"), methyl ethyl ketone ("MEK"), and gamma-valerolactone. One or both of the water-miscible aprotic organic solvent can be an ether, such as, for example, a glyme, dioxane (for example 1,4-dioxane), dioxolane (e.g., 1,3-dioxolane), tetrahydrofuran, and the like. Glymes include, for example, monoglyme (1,2-dimethoxyethane, "DME"), ethyl glyme, diglyme (diethylene glycol dimethyl ether), ethyl diglyme, triglyme, butyl diglyme, tetraglyme, a polyglyme, a highly ethoxylated diether of a high molecular weight alcohol ("higlyme"), and the like.

In some embodiments, the volume ratio of water to the first and second water-miscible organic solvent is approximately 1:1:1 (v:v:v). In some embodiments, the volume ratio of water to the first and second water-miscible organic solvent is approximately 1:2:1 (v:v:v). In some embodiments, the volume ratio of water to the first and second water-miscible organic solvent is approximately 1:2:2 (v:v:v). In some embodiments, the volume ratio of water to the first and second water-miscible organic solvent is approximately 2:1:1 (v:v:v).

In some embodiments, the multi-component solvent for the dehydration solvent comprises water and two different water-miscible organic solvents with the relative amounts of water to the first and second water-miscible organic solvents as shown in Table B.

TABLE B

| Weight percent of water in multi-component solvent system | Weight percent of first water-miscible organic solvent in multi-component solvent system | Weight percent of second water-miscible organic solvent in multi-component solvent system |
|---|---|---|
| 1-5% | 90-98% | 1-5% |
| 1-5% | 85-94% | 5-10% |
| 1-5% | 80-89% | 10-15% |
| 1-5% | 75-84% | 15-20% |

TABLE B-continued

| Weight percent of water in multi-component solvent system | Weight percent of first water-miscible organic solvent in multi-component solvent system | Weight percent of second water-miscible organic solvent in multi-component solvent system |
|---|---|---|
| 1-5% | 70-79% | 20-25% |
| 1-5% | 65-74% | 25-30% |
| 1-5% | 60-69% | 30-35% |
| 1-5% | 55-64% | 35-40% |
| 1-5% | 50-59% | 40-45% |
| 1-5% | 45-54% | 45-50% |
| 1-5% | 40-49% | 50-55% |
| 1-5% | 35-44% | 55-60% |
| 1-5% | 30-39% | 60-65% |
| 1-5% | 25-34% | 65-70% |
| 1-5% | 20-29% | 70-75% |
| 1-5% | 15-24% | 75-80% |
| 1-5% | 10-19% | 80-85% |
| 1-5% | 5-14% | 85-90% |
| 1-5% | 1-9% | 90-94% |
| 5-10% | 85-94% | 1-5% |
| 5-10% | 80-90% | 5-10% |
| 5-10% | 75-85% | 10-15% |
| 5-10% | 70-80% | 15-20% |
| 5-10% | 65-75% | 20-25% |
| 5-10% | 60-70% | 25-30% |
| 5-10% | 55-65% | 30-35% |
| 5-10% | 50-60% | 35-40% |
| 5-10% | 45-55% | 40-45% |
| 5-10% | 40-50% | 45-50% |
| 5-10% | 35-45% | 50-55% |
| 5-10% | 30-40% | 55-60% |
| 5-10% | 25-35% | 60-65% |
| 5-10% | 20-30% | 65-70% |
| 5-10% | 15-25% | 70-75% |
| 5-10% | 10-20% | 75-80% |
| 5-10% | 5-15% | 80-85% |
| 5-10% | 1-10% | 85-89% |
| 10-15% | 80-89% | 1-5% |
| 10-15% | 75-85% | 5-10% |
| 10-15% | 70-80% | 10-15% |
| 10-15% | 65-75% | 15-20% |
| 10-15% | 60-70% | 20-25% |
| 10-15% | 55-65% | 25-30% |
| 10-15% | 50-60% | 30-35% |
| 10-15% | 45-55% | 35-40% |
| 10-15% | 40-50% | 40-45% |
| 10-15% | 35-45% | 45-50% |
| 10-15% | 30-40% | 50-55% |
| 10-15% | 25-35% | 55-60% |
| 10-15% | 20-30% | 60-65% |
| 10-15% | 15-25% | 65-70% |
| 10-15% | 10-20% | 70-75% |
| 10-15% | 5-15% | 75-80% |
| 10-15% | 1-10% | 80-84% |
| 15-20% | 75-84% | 1-5% |
| 15-20% | 70-80% | 5-10% |
| 15-20% | 65-75% | 10-15% |
| 15-20% | 60-70% | 15-20% |
| 15-20% | 55-65% | 20-25% |
| 15-20% | 50-60% | 25-30% |
| 15-20% | 45-55% | 30-35% |
| 15-20% | 40-50% | 35-40% |
| 15-20% | 35-45% | 40-45% |
| 15-20% | 30-40% | 45-50% |
| 15-20% | 25-35% | 50-55% |
| 15-20% | 20-30% | 55-60% |
| 15-20% | 15-25% | 60-65% |
| 15-20% | 10-20% | 65-70% |
| 15-20% | 5-15% | 70-75% |
| 15-20% | 1-10% | 75-79% |
| 20-25% | 70-79% | 1-5% |
| 20-25% | 65-75% | 5-10% |
| 20-25% | 60-70% | 10-15% |
| 20-25% | 55-65% | 15-20% |
| 20-25% | 50-60% | 20-25% |
| 20-25% | 45-55% | 25-30% |
| 20-25% | 40-50% | 30-35% |
| 20-25% | 35-45% | 35-40% |
| 20-25% | 30-40% | 40-45% |
| 20-25% | 25-35% | 45-50% |
| 20-25% | 20-30% | 50-55% |
| 20-25% | 15-25% | 55-60% |
| 20-25% | 10-20% | 60-65% |
| 20-25% | 5-15% | 65-70% |
| 20-25% | 1-10% | 70-74% |
| 25-30% | 65-74% | 1-5% |
| 25-30% | 60-70% | 5-10% |
| 25-30% | 55-65% | 10-15% |
| 25-30% | 50-60% | 15-20% |
| 25-30% | 45-55% | 20-25% |
| 25-30% | 40-50% | 25-30% |
| 25-30% | 35-45% | 30-35% |
| 25-30% | 30-40% | 35-40% |
| 25-30% | 25-35% | 40-45% |
| 25-30% | 20-30% | 45-50% |
| 25-30% | 15-25% | 50-55% |
| 25-30% | 10-20% | 55-60% |
| 25-30% | 5-15% | 60-65% |
| 25-30% | 1-10% | 65-69% |
| 30-35% | 60-69% | 1-5% |
| 30-35% | 55-65% | 5-10% |
| 30-35% | 50-60% | 10-15% |
| 30-35% | 45-55% | 15-20% |
| 30-35% | 40-50% | 20-25% |
| 30-35% | 35-45% | 25-30% |
| 30-35% | 30-40% | 30-35% |
| 30-35% | 25-35% | 35-40% |
| 30-35% | 20-30% | 40-45% |
| 30-35% | 15-25% | 45-50% |
| 30-35% | 10-20% | 50-55% |
| 30-35% | 5-15% | 55-60% |
| 30-35% | 1-10% | 60-64% |
| 35-40% | 55-64% | 1-5% |
| 35-40% | 50-60% | 5-10% |
| 35-40% | 45-55% | 10-15% |
| 35-40% | 40-50% | 15-20% |
| 35-40% | 35-45% | 20-25% |
| 35-40% | 30-40% | 25-30% |
| 35-40% | 25-35% | 30-35% |
| 35-40% | 20-30% | 35-40% |
| 35-40% | 15-25% | 40-45% |
| 35-40% | 10-20% | 45-50% |
| 35-40% | 5-15% | 50-55% |
| 35-40% | 1-10% | 55-59% |
| 40-45% | 50-59% | 1-5% |
| 40-45% | 45-55% | 5-10% |
| 40-45% | 40-50% | 10-15% |
| 40-45% | 35-45% | 15-20% |
| 40-45% | 30-40% | 20-25% |
| 40-45% | 25-35% | 25-30% |
| 40-45% | 20-30% | 30-35% |
| 40-45% | 15-25% | 35-40% |
| 40-45% | 10-20% | 40-45% |
| 40-45% | 5-15% | 45-50% |
| 40-45% | 1-10% | 50-54% |
| 45-50% | 45-54% | 1-5% |
| 45-50% | 40-50% | 5-10% |
| 45-50% | 35-45% | 10-15% |
| 45-50% | 30-40% | 15-20% |
| 45-50% | 25-35% | 20-25% |
| 45-50% | 20-30% | 25-30% |
| 45-50% | 15-25% | 30-35% |
| 45-50% | 10-20% | 35-40% |
| 45-50% | 5-15% | 40-45% |
| 45-50% | 1-10% | 45-49% |
| 50-55% | 40-49% | 1-5% |
| 50-55% | 35-45% | 5-10% |
| 50-55% | 30-40% | 10-15% |
| 50-55% | 25-35% | 15-20% |
| 50-55% | 20-30% | 20-25% |

TABLE B-continued

| Weight percent of water in multi-component solvent system | Weight percent of first water-miscible organic solvent in multi-component solvent system | Weight percent of second water-miscible organic solvent in multi-component solvent system |
|---|---|---|
| 50-55% | 15-25% | 25-30% |
| 50-55% | 10-20% | 30-35% |
| 50-55% | 5-15% | 35-40% |
| 50-55% | 1-10% | 40-44% |
| 55-60% | 35-44% | 1-5% |
| 55-60% | 30-40% | 5-10% |
| 55-60% | 25-35% | 10-15% |
| 55-60% | 20-30% | 15-20% |
| 55-60% | 15-25% | 20-25% |
| 55-60% | 10-20% | 25-30% |
| 55-60% | 5-15% | 30-35% |
| 55-60% | 1-10% | 35-39% |
| 60-65% | 30-39% | 1-5% |
| 60-65% | 25-35% | 5-10% |
| 60-65% | 20-30% | 10-15% |
| 60-65% | 15-25% | 15-20% |
| 60-65% | 10-20% | 20-25% |
| 60-65% | 5-15% | 25-30% |
| 60-65% | 1-10% | 30-34% |
| 65-70% | 25-34% | 1-5% |
| 65-70% | 20-30% | 5-10% |
| 65-70% | 15-25% | 10-15% |
| 65-70% | 10-20% | 15-20% |
| 65-70% | 5-15% | 20-25% |
| 70-75% | 20-29% | 1-5% |
| 70-75% | 15-25% | 5-10% |
| 70-75% | 10-20% | 10-15% |
| 70-75% | 5-15% | 15-20% |
| 75-80% | 15-24% | 1-5% |
| 75-80% | 10-20% | 5-10% |
| 75-80% | 5-15% | 10-15% |

The concentration of sugar in the carbohydrate feedstock is typically in the range of from or any number in between 2 wt % to 80 wt % or from or any number in between 5 wt % to 80 wt %. In various embodiments, the concentration of sugar is in the range of from or any number in between 20 wt % to 80 wt %. In some embodiments, the concentration of sugar in the carbohydrate feedstock is in the range of from or any number in between 5 wt % to 20 wt %. In other embodiments, the concentration of sugar in the carbohydrate feedstock is in the range of from or any number in between 5 wt % to 40 wt %. In some embodiments, the concentration of sugar in the carbohydrate feedstock ranges from or any number in between 5-15 wt %, 10-20 wt %, 15-25 wt %, 20-30 wt %, 25-35 wt %, 30-40 wt %, 35-45 wt %, 40-50 wt %, 45-55 wt %, 50-60 wt %, 55-65 wt %, 60-70 wt %, 65-75 wt % or 70-80 wt %, or within a range defined by any two of the aforementioned weight percentages.

Catalysts that are suitable for use in the dehydration process include homogeneous catalysts, including, for example, homogeneous acid catalysts, and the like, as well as heterogeneous catalysts. Suitable homogeneous acid catalysts include, for example, an inorganic acid, such as, for example, a mineral acid (e.g., $H_2SO_4$, $HNO_3$, HCl, HBr, or HI, and the like, as well as any combination of two or more thereof), a Brønsted acid (e.g., HCl, HI, $H_2SO_4$, $HNO_3$, $H_3PO_4$, oxalic acid, methanesulfonic acid, or trifluoromethanesulfonic acid, and the like, as well as any combination of any two or more thereof), a Lewis acid (e.g., a borontrihalide, an organoborane, an aluminum trihalide, a phosphorus pentafluoride, an antimony pentafluoride, a rare earth metal triflate, a metal halide (e.g., $ZnCl_2$ and $ZnBr_2$), a metal trifluoroacetate or a metal cation ether complex, and the like, as well as any combination of two or more thereof), an organic acid (e.g., triflic acid, methansulfonic acid, benzenesulfonic acid, p-toluene sulfonic acid, oxalic acid, or levulinic acid, and the like, as well as any combination of two or more thereof), and any combination thereof.

Quantities of homogeneous catalyst employed are typically in the range of from or any number in between 0.1 to 25 mol %, and more typically in the range of from or any number in between 0.5 to 5 mol % (wherein, mol % is calculated on the basis of moles of sugar, e.g., hexose). Heterogeneous catalysts that are suitable for use in the practice of the present disclosure include an acid-functionalized resin, an acidified carbon, a zeolite, a micro- and/or meso-porous metal oxide, a sulfonated metal oxide, a phosphonated metal oxide, a clay, or a polyoxometallate, and combinations thereof. Preferred heterogeneous catalysts include acid-functionalized resins. The heterogeneous catalyst loading is typically in the range of or any number in between 1 g/L to 20 g/L in a slurry reactor, (such as e.g., 1, 2, 3, 4, 5, 6, 7, 8, 9, 10, 11, 12, 13, 14, 15, 16, 17, 18, 19 or 20 g/L) and in the range of from or any number in between 200 g/L to 1500 g/L (such as e.g., 200, 300, 400, 500, 600, 700, 800, 900, 1000, 1100, 1200, 1300, 1400, or 1500 g/L) in a fixed bed reactor. The skilled artisan will recognize that the heterogeneous catalyst loading will vary depending on the specific type of reactor used, but can readily determine the loading based on these guidelines.

In a further specific embodiment, the present disclosure provides a process for producing a furanic oxidation substrate, the process comprising:

(a°) contacting a carbohydrate feedstock comprising a sugar and a dehydration solvent with an acid catalyst under conditions sufficient to form a (dehydration) reaction mixture for dehydrating the sugar to produce a furanic oxidation substrate, wherein the acid catalyst is an acid selected from the group consisting of HBr, $H_2SO_4$, $HNO_3$, HCl, HI, $H_3PO_4$, triflic acid, methansulfonic acid, benzenesulfonic acid, and p-toluene sulfonic acid, wherein when the acid catalyst is not HBr, the reaction mixture further comprises a bromide salt, and wherein the dehydration solvent comprises NMP. Typically, the acid catalyst is a homogeneous acid catalyst. Suitable organic acids include those mentioned hereinabove. Suitable bromide salts include LiBr, NaBr, KBr, $MgBr_2$, $CaBr_2$, $ZnBr_2$, or ammonium bromide salts having the chemical structure of $R_4N^+Br^-$, where R is a $C_1$-$C_6$ alkyl group. Exemplary ammonium bromide salts include, but are not limited to, tetramethylammonium bromide, tetraethylamminium bromide, tetrapropylammonium bromide, or tetrabutylammonium bromide, and the like. The quantity of bromide salt employed is typically in molar excess of the acid present in the reaction mixture.

Quantities of acid catalyst employed are typically in the range of from or any number in between 0.1 to 25 mol %, and more typically in the range of from or any number in between 0.5 to 5 mol % (wherein, mol % is calculated on the basis of moles of sugar, e.g., hexose). In some embodiments, the amount of acid catalyst in the reaction mixture for dehydrating the sugar results in the reaction mixture having an acidic pH. In some embodiments, the amount of acid catalyst in the reaction mixture for dehydrating the sugar results in the reaction mixture having a pH of less than 6. In some embodiments, the amount of acid catalyst in the reaction mixture for dehydrating the sugar results in the reaction mixture having a pH of less than 5. In some embodiments, the amount of acid catalyst in the reaction mixture for dehydrating the sugar results in the reaction mixture having a pH of less than 4. In some embodiments, the amount of acid catalyst in the reaction mixture for dehydrating the sugar results in the reaction mixture having a pH of less than 3. In some embodiments, the amount of acid catalyst in the reaction mixture for dehydrating the sugar results in the reaction mixture having a pH of less than 2. In some embodiments, the amount of acid catalyst in the reaction mixture for dehydrating the sugar results in the reaction mixture having a pH of less than 1.

The dehydration reaction mixtures described hereinabove are typically maintained at a temperature in the range of from or any number in between 50° C. to 250° C., (such as e.g., 50, 60, 70, 80, 90, 100, 110, 120, 130, 140, 150, 160, 180, 190, 200, 210, 220, 230, 240, or 250° C. or within a range defined by any two of the aforementioned temperatures) and a pressure in the range of from or any number in between 1 atm to 15 atm, or from or any number in between 2 atm to 15 atm (such as e.g., 1, 2, 3, 4, 5, 6, 7, 8, 9, 10, 11, 12, 13 14, or 15 atm). More typically, the dehydration reaction mixture is maintained at a temperature in the range of from or any number in between 80° C. to 180° C. (such as e.g., 80, 90, 100, 110, 120, 130, 140, 150, 160, 180° C. or within a range defined by any two of the aforementioned temperatures). In some embodiments, the dehydration mixture is maintained at a temperature in the range of from or any number in between 80° C. and 160° C., or 80° C. and 150° C., or 80° C. and 140° C., or 80 and 130° C., or 80° C. and 120° C., or 80° C. and 110° C., or 80° C. and 100° C. In some embodiments, the dehydration mixture is maintained at a temperature that is less than 110° C., or less than 100° C. Applicants have discovered that the dehydration mixture of the present disclosure can provide surprisingly high yields of furanic oxidation substrate at relatively low temperatures of less than 110° C., such as less than 100° C.

To minimize production of undesired products, and maximize yield of the furanic oxidation substrate, it may be desirable to carry out the dehydration reaction to a partial conversion endpoint, as described in WO 2015/113060 (which is incorporated herein by reference), by quenching the reaction, and separating and recycling unconverted sugar, by, for example, filtration. When the furanic oxidation substrate is generated by the dehydration reaction, it is present in a dehydration product solution. As used herein, the term "dehydration product solution" refers to a solution comprising the furanic oxidation substrate and the dehydration solvent. The dehydration product solution can be a mixture that includes dissolved furanic oxidation substrate and one or more components that are not dissolved, wherein the one or more components that are not dissolved are selected from humin and unreacted sugar. The furanic oxidation substrate may be optionally separated from one or more components selected from the group consisting of a humin and an unreacted sugar and/or isolated from the dehydration product solution, and optionally further purified. In one such embodiment, the dehydration product solution is subjected to a membrane to effect the separation of the furanic oxidation substrate from one or more components selected from the group consisting of a humin and an unreacted sugar. Membranes suitable for use for such separation include nanofiltration membranes, ultrafiltration membranes, and combination thereof.

The dehydration product solution may be used as a feedstock for producing an FDCA pathway product or derivative thereof, or another subsequent process that utilizes the furanic oxidation substrate. Typically, the furanic oxidation substrate is HMF.

The dehydration of the carbohydrate feedstock to produce the furanic oxidation substrate can produce the furanic oxidation substrate in yield that is typically at least 60% (on a molar basis). In some embodiments, the yield is at least 70%, and in other embodiments, it is at least 80%, at least 90%, at least 95%, at least 98% or at least 99%. In some embodiments, the yield ranges from between 60-65%, 62-67%, 65-70%, 67-72%, 70-75%, 72-77%, 75-80%, 77-82%, 80-85%, 82-87%, 85-90%, 87-92%, 90-95%, 92-97%, 95-98%, or 97-99%, or is within a range defined by any two of the aforementioned percentages.

In a specific embodiment, prior to step (a) of the FDCA pathway product-generating oxidation processes of the present disclosure, step (a°) is carried out to produce a furanic oxidation substrate in a dehydration product solution. The dehydration product solution can be used either directly or indirectly (i.e., with one or more intervening pre-treatment step(s)), as the oxidation feedstock for step (a). The pre-treatment step(s) may include a separation step (e.g., filtration or membrane separation step (such as, for example ultrafiltration or nanofiltration), chromatography, ion exchange, and the like), a distillation step (to remove all or a portion of a component solvent), or other similar step/process suitable for amending the composition of the dehydration product solution to conform to a desired composition or form of the oxidation feedstock to be used in step (a). In this embodiment, the dehydration solvent typically comprises at least one solvent species in common with the oxidation solvent. One or more additional solvent species may be added to the dehydration product solution during a pre-treatment step to formulate the dehydration product solution into a desired oxidation feedstock composition for use in step (a). To illustrate, the dehydration solvent may be a water-miscible aprotic organic solvent. After conducting step (a°), but before performing step (a), water can be added to the dehydration product solution in a pre-treatment step, and the resulting oxidation feedstock, comprising the furanic oxidation substrate and oxidation solvent (i.e., in this example, a multi-component solvent made up of the water-miscible aprotic organic solvent and water) can be used in step (a). Alternatively, the dehydration product solution can be used directly (i.e., as is) as the oxidation feedstock for step (a). In this embodiment, the dehydration production solution comprises a dehydration solvent that is typically a multi-component solvent comprising water and an aprotic organic solvent (i.e., a multi-component solvent that is suitable for use as the oxidation solvent).

The foregoing and other aspects of the disclosure may be better understood in connection with the following non-limiting examples.

EXAMPLES

Example 1

FDCA Solubility Characterization

Solvents were screened for the ability to dissolve FDCA. 10 ml of a candidate solvent was heated to a certain temperature and FDCA (Product No. F0710, TCI America) was added by small portions to the heated candidate solvent until the FDCA amount exceeded the solubility limit. After that, small volumes of solvent were added until the excess solids were completely dissolved. The experiment was repeated two times at each temperature and the average was taken as FDCA solubility. Five solvents were tested: (1) deionized water; (2) diglyme; (3) dioxane; (4) a 1:1 by volume mixture of diglyme with deionized water; and (5) a 4:1 by volume mixture of dioxane with deionized water. The results are depicted in FIG. 3 as a plot of FDCA Solubility (Weight %) as a function of temperature (° C.). The results show that FDCA appears to have relatively low solubilities in each of water, diglyme, and dioxane in the temperature range of 25° C. to 100° C. However, when each of the organic solvents was combined with water, the resulting co-solvent appeared to provide a synergistic enhancement in FDCA solubilizing capability. For example, at 100° C., although FDCA solubility in water and diglyme individually was less than 1% (by weight) and less than 2% (by weight), respectively, FDCA solubility reached 9% (by weight) when the two solvents were combined in a co-solvent system of 1:1 ratio of deionized water:diglyme, by volume. Similarly, at 100° C., although FDCA solubility in water and dioxane individually was less than 1% (by weight) and less than 2% (by weight), respectively, the FDCA solubility trend line for the co-solvent system of 1:4 ratio of deionized water:dioxane, by volume, indicates 9% (by weight) FDCA solubility.

Example 2

Preparation of Heterogeneous Oxidation Catalyst (3 wt % Pt/Silica)

A metal precursor solution was first prepared by mixing 0.152 ml of a solution of $Pt(NH_3)_4(OH)_2$ (containing 101.8 mg Pt/ml) with 0.047 ml of de-ionized water. This solution was used to impregnate 0.5 g of silica (Cariact Q-50, BET specific surface area 80 $m^2/g$, mean pore diameter 50 nm, particle size 75-150 μm, Fuji Silysia Corporation). After impregnation, the material was dried at 120° C. for two hours, then reduced under a flow of 6% $H_2$ in argon at 300° C. for two hours. After cooling, the material was passivated under a flow of 0.5% $O_2$ in nitrogen for 15 minutes. The resultant material, containing a 3 wt % Pt loading, was used for catalytic activity testing, as described in Example 11, without any further pretreatment.

Examples 3 and 4

Preparation of Heterogeneous Oxidation Catalyst (2.5 wt % Pt/Silica and 4 wt % Pt/Silica)

Heterogeneous oxidation catalysts were prepared as described in Example 2 except that 0.204 ml of $Pt(NH_3)_4(OH)_2$ solution (containing 62.8 mg Pt/ml) and 0.546 ml of deionized water, was used to prepare heterogeneous oxidation catalysts with platinum loadings of 2.5 wt % (Example 3) and 0.205 ml of $Pt(NH_3)_4(OH)_2$ solution (containing 101.8 mg Pt/ml) and 0.42 ml de-ionized water were used to prepare catalyst with a platinum loading of 4 wt % (Example 4). The resultant materials were used for catalytic activity testing as described in Example 11.

Example 5

Preparation of Heterogeneous Oxidation Catalyst (3 wt % Pt/$ZrO_2$)

A metal precursor solution was first prepared by mixing 0.152 ml of a solution of $Pt(NH_3)_4(OH)_2$ (containing 101.8 mg Pt/ml) with 0.048 ml of deionized water. This solution was used to impregnate 0.5 g $ZrO_2$ (SZ31163, BET specific surface area 55 $m^2/g$, bimodal pore size distributions with mean pore diameters of 16 and 60 nm, particle size <150 μm, Saint Gobain). After impregnation, the material was dried at 120° C. for 2 hours and then reduced under a flow of 6% $H_2$ in argon at 300° C. for 2 hours. After cooling, the material was passivated under a flow of 0.5% $O_2$ in nitrogen for 15 minutes. The resultant material, containing a 3 wt % Pt loading, was used for catalytic activity testing, as described in Example 11, without any further pretreatment.

Example 6

Preparation of Heterogeneous Oxidation Catalyst (4 wt % Pt/$ZrO_2$)

The heterogeneous oxidation catalyst was prepared as described in Example 5 except 0.205 ml of the same $Pt(NH_3)_4(OH)_2$ solution was used to prepare a material with a platinum loading of 4 wt %. The resultant material was used for catalytic testing as described in Example 11.

Example 7

Preparation of Heterogeneous Oxidation Catalyst (3 wt % Pt/$Al_2O_3$)

A metal precursor solution was first prepared by mixing 0.152 ml of a solution of $Pt(NH_3)_4(OH)_2$ (containing 101.8 mg Pt/ml) with 0.298 ml of deionized water. This solution was used to impregnate 0.5 g $Al_2O_3$ (SA 31132, BET specific surface area 55 $m^2/g$, bimodal with mean pore diameters of 25 and 550 nm, particle size <150 μm, Saint Gobain). After impregnation, the material was dried at 120° C. for 2 hours. Finally, the material was reduced under flow of 6% $H_2$ in argon at 300° C. for 2 hours. After cooling, the material was passivated under a flow of 0.5% $O_2$ in nitrogen for 15 minutes. The resultant material, containing a 3 wt % Pt loading, was used for catalytic activity testing, as described in Example 11, without any further pretreatment.

Example 8

Preparation of Heterogeneous Oxidation Catalyst (4 wt % Pt/$Al_2O_3$)

The heterogeneous oxidation catalyst in this example was prepared in the manner described in Example 7, except that 0.205 ml of the same $Pt(NH_3)_4(OH)_2$ solution and 0.245 ml of de-ionized water were used to prepare a metal precursor solution that was used to prepare material with a platinum loading of 4 wt %. The resultant material was used for catalytic activity testing as described in Example 11.

Examples 9 and 10

Preparation of Heterogeneous Oxidation Catalysts 2 wt % Pt, 1 wt % Au/Silica; 1 wt % Pt, 2 wt % Au/Silica A metal precursor solution was first prepared by mixing 0.018 ml of a solution of $PtONO_3$ (containing 100 mg Pt/ml) with 0.009 ml of a solution of $(NH_4)_2AuO_2$ (containing 100 mg Au/ml) and 0.09 ml of deionized water (Example 9), and correspondingly mixing 0.009 ml of the $PtONO_3$ solution (containing 100 mg Pt/ml) with 0.018 ml of $(NH_4)_2AuO_2$ solution (containing 100 mg Au/ml) and 0.09 ml deionized water (Example 10). Each solution was used to impregnate 0.1 g of silica (Cariact Q-50, particle size 75-150 μm, specific surface area 80 $m^2/g$, mean pore diameter 50 nm, Fuji Silisia Corporation). After impregnation, material was reduced under flow of 6% $H_2$ in argon at 350° C. for 3 hours. After cooling, the material was passivated under a flow of 0.5% $O_2$ in nitrogen for 15 minutes. The resultant materials, containing a 2 wt % Pt loading and a 1 wt % Au loading (Example 9) and containing a 1 wt % Pt, 2 wt % Au loading (Example 10) were used for catalytic activity testing, as described in Example 11, without any further pretreatment.

Example 11

Catalyst Performance Assay and Production of FDCA Pathway Products

Catalyst testing was conducted within 1 ml glass vials housed in a 96-well insert situated in a high pressure high throughput reactor. See Diamond, G. M., Murphy, V., Boussie, T. R., in *Modern Applications of High Throughput R&D in Heterogeneous Catalysis*, (eds, Hagemeyer, A. and Volpe, A. Jr. Bentham Science Publishers 2014, Chapter 8, 299-309); see also U.S. Pat. No. 8,669,397, both of which are incorporated herein by reference. 20 mg of each catalyst was placed into the reactor along with 0.8 ml of a 0.5 M HMF solution prepared in a 4:1 (v/v) dioxane:$H_2O$ mixture (this corresponds to 6 wt % of HMF). The 1 ml reaction vials within the insert were each covered with a Teflon sheet, a silicon mat and a steel gas diffusion plate each containing pin-holes to enable gas entry. The insert was placed within a pressure vessel which was leak tested under nitrogen pressure. The atmosphere within the reactor was then replaced by oxygen and the reactor was heated to 90° C. and shaken at 500 rpm for 20 hours, and at 200 psig oxygen pressure. After the reaction was completed, the shaking was stopped and the reactor was cooled down to room temperature. Samples were prepared for HPLC analysis by sampling from each reactor and diluting the sample by a factor of 200 with a 4:1 dioxane:$H_2O$ mixture. Reaction products were hydroxymethylfurancarboxylic acid (HMFCA), formylfurancarboxylic acid (FFCA), diformylfuran (DFF) and FDCA. The results are shown in Table 1.

At the relatively low metal loadings reported above, the BET specific surface areas of the solid support materials are believed to remain unchanged in the formulated heterogeneous oxidation catalyst.

Example 12

Preparation and Testing of Carbon-Supported Catalysts

An aqueous solution (0.10 ml) containing 10 mg/ml Au added in the form of $Me_4NAuO_2$ and 20 mg/ml Pt added in the form of $PtO(NO_3)$ was added to carbon black powder (100 mg) of Cabot Monarch 570. The mixture was agitated to impregnate the carbon black support and was dried in a 70° C. oven overnight under a dry air purge. The sample was then reduced at 350° C. under forming gas (5% $H_2$ and 95% $N_2$) atmosphere for 2 hours with 5° C./min temperature ramp rate. The final catalyst was composed of ca. 1.0 wt % Au and 2.0 wt % Pt. By using other carbon black and adjusting amount of Au and Pt in solution, different catalysts with various Au and Pt loadings on a variety of commercial carbon black powders or particles from extrudates were prepared in a similar manner. The compositions for these catalysts are listed in Table 2, hereinbelow.

These catalysts were tested for hydroxymethylfurfural (HMF) oxidation using the following testing protocol. Catalyst (10 mg) was weighed into a glass vial insert followed by addition of an aqueous HMF solution (250 μl of 0.50 M or 6.0 wt % in 1,4-dioxane:water (4:1 v/v)). The glass vial insert was loaded into a reactor and the reactor was closed. The atmosphere in the reactor was replaced with oxygen and pressurized to 200 psig at room temperature. The reactor was heated to 110° C. and maintained at the respective temperature for 4 hours, or 90° C. and maintained at the respective temperature for 20 hours, while the vial was shaken. After that, shaking was stopped and reactor was cooled to 40° C. The pressure in the reactor was then slowly released. The glass vial insert was removed from the reactor and centrifuged. The solution was diluted with 1,4-dioxane:water (4:1 v/v) and analyzed by HPLC with a UV detector to determine the yield of 2,5-furandicarboxylic acid (FDCA). The results are presented in Table 2.

TABLE 1

Catalyst Composition and Performance.

| Example | BET Specific Surface Area | Mean Pore Diameter | Support | Pt, wt % | Au, wt % | HMFCA Yield % | DFF Yield % | FFCA Yield % | FDCA Yield % |
|---|---|---|---|---|---|---|---|---|---|
| 2 | 75 | 50 nm | $SiO_2$ | 3 | 0 | 0 | 0 | 1 | 91 |
| 3 | 75 | 50 nm | $SiO_2$ | 4 | 0 | 0 | 0 | 2 | 81 |
| 4 | 75 | 50 nm | $SiO_2$ | 2.5 | 0 | 0 | 0 | 4 | 85 |
| 5 | 55 | Bimodal 16 nm & 60 nm | $ZrO_2$ | 3 | 0 | 0 | 0 | 31 | 52 |
| 6 | 55 | Bimodal 16 nm & 60 nm | $ZrO_2$ | 4 | 0 | 0 | 0 | 21 | 56 |
| 7 | 55 | Bimodal 25 nm & 550 nm | $Al_2O_3$ | 3 | 0 | 0 | 0 | 32 | 37 |
| 8 | 55 | Bimodal 25 nm & 550 nm | $Al_2O_3$ | 4 | 0 | 0 | 0 | 30 | 36 |
| 9 | 75 | 50 nm | $SiO_2$ | 2 | 1 | 0 | 0 | 30 | 43 |
| 10 | 75 | 50 nm | $SiO_2$ | 1 | 2 | 2 | 10 | 40 | 10 |

TABLE 2

Catalyst Composition and Performance.

| Carbon Support | BET Surface Area m²/g | Mean Pore Diameter (nm) | Screening Condition | Metal Loading | FDCA Yield (mol %) |
|---|---|---|---|---|---|
| Cabot Monarch 120 | 23 | 28 | 90° C./20 h | 3.0 wt % Pt | 82 |
| Cabot Monarch 280 | 30 | 18 | 90° C./20 h | 3.0 wt % Pt | 88 |
| Cabot Monarch 280 | 30 | 18 | 90° C./20 h | 1.0 wt % Au 2.0 wt % Pt | 60 |
| Cabot Monarch 570 | 102 | 14 | 90° C./20 h | 3.0 wt % Pt | 84 |
| Cabot Monarch 570 | 102 | 14 | 90° C./20 h | 1.0 wt % Au 2.0 wt % Pt | 68 |
| Cabot Monarch 700 | 181 | 12 | 90° C./20 h | 3.0 wt % Pt | 81 |
| Cabot Monarch 700 | 181 | 12 | 90° C./20 h | 1.0 wt % Au 2.0 wt % Pt | 73 |
| Sid Richardson SC159 | 231 | 13 | 90° C./20 h | 3.0 wt % Pt | 70 |
| Timcal Ensaco 150G | 47 | 14 | 90° C./20 h | 3.0 wt % Pt | 82 |
| Timcal Ensaco 250G | 64 | 14 | 90° C./20 h | 3.0 wt % Pt | 79 |

TABLE 2-continued

Catalyst Composition and Performance.

| Carbon Support | BET Surface Area $m^2/g$ | Mean Pore Diameter (nm) | Screening Condition | Metal Loading | FDCA Yield (mol %) |
|---|---|---|---|---|---|
| Cabot Monarch 120 | 23 | 28 | 110° C./4 h | 3.0 wt % Pt | 65 |
| Cabot Monarch 280 | 30 | 18 | 110° C./4 h | 3.0 wt % Pt | 73 |
| Cabot Monarch 570 | 102 | 14 | 110° C./4 h | 3.0 wt % Pt | 62 |
| Cabot Monarch 700 | 181 | 12 | 110° C./4 h | 3.0 wt % Pt | 67 |
| Timcal Ensaco 150G | 47 | 14 | 110° C./4 h | 3.0 wt % Pt | 71 |

Example 13

Crystallization of FDCA from a Multi-Component Solvent Comprising Water and an Aprotic Organic Solvent 0.5 g FDCA was weighed into 2 vials with magnetic stirrers. In Vial 1, 3 ml $H_2O$ and 2 ml glyme were added. In Vial 2, 2 ml $H_2O$ and 3 ml glyme was added. Insoluble milky white suspensions formed at room temperature. The vials were heated with stirring to 140° C. in an oil bath. The suspension in Vial 1 turned into a clear solution with full apparent FDCA solubility at ~130° C. The suspension in Vial 2 turned into a clear solution with full apparent FDCA solubility at ~110° C. As the temperature of the clear solutions were slowly reduced to room temperature, FDCA crystallized to produce purified FDCA.

Description of Analytical Method

The analytical instrumentation used in the following examples was a Thermo Scientific Dionex Ultimate System fitted with a Thermo Scientific Hypercarb 3 μm 3×50 mm analytical column and a 3000 RS Variable Wavelength UV/Vis Detector.

Example 14

Preparation of 40 g Heterogeneous Oxidation Catalyst (3.0 wt. % Pt/Carbon)

A metal precursor solution was first prepared by mixing 5.64 ml of a solution of platinum nitrate (containing 219 mg Pt/ml from Heraeus Group) and 94.4 ml of deionized water. This solution was used to impregnate 40.0 g of carbon powder (Continental N234 carbon black powder, BET surface area 117 $m^2/g$, average pore diameter 14 nm). After impregnation, the material was dried at 100° C. for 3 hours and then reduced under a flow of 5% $H_2$ in nitrogen at 350° C. for 3 hours with 5° C./min temperature ramp rate. After cooling, the material was passivated under a flow of 0.5% $O_2$ in nitrogen for 15 minutes. The resultant material, containing a 3.0 wt. % Pt loading, was used for catalytic activity testing as described in Example 15, without any further pretreatment.

Example 15

Testing of Carbon-Supported Catalyst in Parr Pressure Reactor

Catalyst testing was conducted in a 300 ml Parr stainless steel autoclave pressure reactor. Catalyst was weighed (e.g., 8.00 g of 3.0 wt. % Pt/Continental $N_{234}$ carbon black powder) and placed into reactor, along with a substrate HMF (5-(hydroxymethyl)furfural) solution (100 g 6.0 wt. % prepared in either a 65 wt. % DME/35 wt. % $H_2O$ solvent mixture or a 60 wt. % 1,4-Dioxane/40 wt. % $H_2O$ solvent mixture). The reactor was assembled and a magnetic drive coupled stirrer was attached.

The reactor was pressurized with process gas ($O_2$) to desired pressure with stirring (1000 rpm) at ambient temperature, followed by heating to target temperature and holding at that temperature for the planned reaction time. After the ascribed reaction time, the reactor was cooled with stirring lowered to ca. 200 rpm, and vented slowly at 30° C.

Dimethyl sulfoxide (DMSO) was added to the reactor for the first step dilution. After stirring for ca. 30 min, the product solution was centrifuged and further diluted with de-ionized water for HPLC analysis.

The reaction products were 5-Hydroxymethyl-furan-2-carboxylic acid (HMFCA), 2,5-Furandicarboxaldehyde (DFF), 5-Formylfuran-3-carboxylic acid (FFCA), and 2,5-Furandicarboxylic Acid (FDCA). Each of above products as well as any remaining HMF was quantified through a calibration curve for each analyte by plotting the relative concentration vs. the relative detector response of calibration standard samples and fit to a parabolic expression. Results are summarized in Table 3.

TABLE 3

Catalyst Performance in Parr Pressure Reactor.

| Run No. | Catalyst (g) | Temp. (° C.) | $O_2$ Pressure (psig) | Reaction Time (min) | Yield Solvent | FFCA Yield (mol %) | FDCA Yield (mol %) | Mass Balance (mol %) |
|---|---|---|---|---|---|---|---|---|
| 1 | 8.00 | 120 | 200 | 90 | 65 wt. % DME/ 35 wt. % $H_2O$ | 1.1 | 90.0 | 91.1 |
| 3 | 8.00 | 110 | 250 | 90 | 65 wt. % DME/ 35 wt. % $H_2O$ | 4.9 | 91.3 | 96.2 |
| 4 | 8.00 | 110 | 250 | 120 | 60 wt. % Dioxane/ 40 wt. % $H_2O$ | 2.7 | 92.4 | 95.1 |

Mass balance represent the sum of the mol % yields of HMF, HMFCA, DFF, FFCA and FDCA.

Example 16

Preparation and Testing of a Variety of Carbon-Supported Catalysts

An aqueous solution (0.60 ml) containing 10 mg/ml Pt in the form of platinum nitrate was added to carbon black powder (200 mg), and the resultant material was agitated to impregnate the supports. The samples were then dried in an oven at 70° C. overnight, and reduced at 350° C. under a forming gas (5% $H_2$ and 95% $N_2$) atmosphere for 3 hours with 5° C./min temperature ramp rate to produce catalyst with a composition of 3.0 wt. % Pt. By using other carbon black supports, Pt precursors, and adjusting amount of Pt in solution, different catalysts with various Pt loadings on a variety of commercial carbon black powders, particles from extrudates, or extrudates can be prepared in a similar manner.

These catalysts were tested for 5-(Hydroxymethyl)furfural (HMF) oxidation using the following testing protocol. Catalyst (10 mg) was weighed into a 1 ml glass vial insert followed by addition of an HMF solution (250 al of 6.0 wt. % or 0.50 M in 23 wt. % Diglyme/77 wt. % $H_2O$). The glass vial insert was loaded into a reactor and the reactor was closed. The atmosphere in the reactor was replaced with oxygen and pressurized to 200 psig at ambient temperature. The reactor was heated to 110° C. and maintained at the respective temperature for 3 hours while the vial was shaken. After that, shaking was stopped and reactor was cooled to 40° C. Pressure in the reactor was then slowly released. The glass vial insert was removed from the reactor and centrifuged. The solution was diluted with dimethyl sulfoxide (DMSO) followed by 1,4-dioxane:water (2:1 v/v) and analyzed by HPLC with a UV detector to determine the yield of 2,5-furandicarboxylic acid (FDCA). Results are presented in Table 4.

TABLE 4

Catalyst Performance.

| Carbon Support | BET Surface Area ($m^2/g$) | FDCA Yield (mol %) |
| --- | --- | --- |
| Orion Arosperse 15 | 9 | 66 |
| Asbury A99 | 19 | 44 |
| Orion Lamp Black 101 | 20 | 82 |
| Cabot Monarch 120 | 23 | 80 |
| Cabot Monarch 280 | 30 | 82 |
| Asbury 5375R | 30 | 77 |
| Asbury 5365R | 34 | 81 |
| Asbury 5345 | 37 | 80 |
| Continental N550 | 38 | 80 |
| Continental N120 | 39 | 80 |
| Arosperse 5-183A | 42 | 79 |
| Timcal Ensaco 150G | 47 | 77 |
| Timcal Ensaco 250G | 56 | 80 |
| Timcal Ensaco 260G | 63 | 79 |
| Asbury 5348R | 65 | 80 |
| Asbury 5358R | 67 | 81 |
| Orion N330 | 76 | 78 |
| Continental N330-C | 77 | 80 |
| Cabot Monarch 570 | 102 | 77 |
| Orion HiBlack 40B2 | 109 | 58 |
| Continental N234 | 117 | 81 |
| Orion Arosperse 138 | 120 | 74 |
| Sid Richardson Ground N115 | 128 | 70 |
| Sid Richardson SC419 | 136 | 76 |
| Sid Richardson Ground SR155 | 146 | 63 |
| Orion HP-160 | 158 | 59 |
| Aditya Birla CDX-KU | 167 | 63 |
| Aditya Birla CSCUB | 169 | 64 |
| Cabot Monarch 700 | 181 | 65 |
| Orion Hi-Black 50 LB | 183 | 69 |
| Aditya Birla R2000B | 187 | 67 |
| Orion Hi-Black 50L | 193 | 73 |
| Asbury 5302 | 211 | 68 |
| Asbury 5303 | 219 | 65 |
| Cabot Vulcan XC72 | 231 | 62 |
| Sid Richardson SC159 | 231 | 51 |
| Orion Hi-Black 600 L | 235 | 70 |

TABLE 4-continued

Catalyst Performance.

| Carbon Support | BET Surface Area ($m^2/g$) | FDCA Yield (mol %) |
| --- | --- | --- |
| Aditya Birla R250OUB | 247 | 46 |
| Orion Printex L 6 | 250 | 54 |
| Asbury 5379 | 271 | 52 |
| Asbury 5368 | 303 | 68 |
| Aditya Birla R3500B | 320 | 60 |
| Orion Color Black FW 2 | 350 | 61 |
| Aditya Birla R5000U2 | 583 | 61 |
| Cabot Norit Darco 12x20L1 | 592 | 12 |
| Orion Color Black FW 255 | 650 | 58 |
| Timcal Ensaco 350G | 770 | 31 |

Example 17

Testing of Carbon-Supported Powder Catalysts in a Variety of Solvent Compositions A selection of above catalysts were tested for 5-(Hydroxymethyl)furfural (HMF) oxidation with very similar testing protocol by using 10 mg 3.0 wt. % Pt on carbon black powder (prepared from platinum nitrate) in an HMF solution (250 al of 6.0 wt. % or 0.50 M in a variety of solvent mixtures of water with DME, 1,4-dioxane and diglyme). The glass vial insert was loaded into a reactor and the reactor was closed. The atmosphere in the reactor was replaced with oxygen and pressurized to 200 psig at ambient temperature. The reactor was heated to 110° C. and maintained at the respective temperature for 3 hours while the vial was shaken. After that, shaking was stopped and reactor was cooled to 40° C. The pressure in the reactor was then slowly released. The glass vial insert was removed from the reactor and centrifuged. The solution was diluted with dimethyl sulfoxide (DMSO) followed by 1,4-dioxane:water (2:1 v/v) and analyzed by HPLC with a UV detector to determine the yield of 2,5-furandicarboxylic acid (FDCA). The results are presented in Table 5.

TABLE 5

Powder Catalyst Performance in Various Solvent Compositions

| Carbon Support | BET Surface Area ($m^2/g$) | Solvent | FDCA Yield (mol %) |
| --- | --- | --- | --- |
| Asbury 5358R | 67 | 50 wt. % DME/50 wt. % $H_2O$ | 81 |
| Asbury 5375R | 30 | 50 wt. % DME/50 wt. % $H_2O$ | 72 |
| Cabot Monarch 280 | 30 | 50 wt. % DME/50 wt. % $H_2O$ | 79 |
| Continental N234 | 117 | 50 wt. % DME/50 wt. % $H_2O$ | 81 |
| Continental N330 | 77 | 50 wt. % DME/50 wt. % $H_2O$ | 81 |
| Orion Arosperse 5-183A | 42 | 50 wt. % DME/50 wt. % $H_2O$ | 79 |
| Orion Lamp Black 101 | 20 | 50 wt. % DME/50 wt. % $H_2O$ | 81 |
| Timcal Ensaco 250G | 56 | 50 wt. % DME/50 wt. % $H_2O$ | 80 |
| Asbury 5358R | 67 | 90 wt. % DME/10 wt. % $H_2O$ | 51 |
| Asbury 5375R | 30 | 90 wt. % DME/10 wt. % $H_2O$ | 31 |
| Cabot Monarch 280 | 30 | 90 wt. % DME/10 wt. % $H_2O$ | 50 |
| Continental N234 | 117 | 90 wt. % DME/10 wt. % $H_2O$ | 50 |
| Continental N330 | 77 | 90 wt. % DME/10 wt. % $H_2O$ | 54 |
| Orion Arosperse 5-183A | 42 | 90 wt. % DME/10 wt. % $H_2O$ | 50 |
| Orion Lamp Black 101 | 20 | 90 wt. % DME/10 wt. % $H_2O$ | 51 |
| Timcal Ensaco 250G | 56 | 90 wt. % DME/10 wt. % $H_2O$ | 50 |
| Asbury 5358R | 67 | 50 wt. % Dioxane/50 wt. % $H_2O$ | 73 |
| Asbury 5375R | 30 | 50 wt. % Dioxane/50 wt. % $H_2O$ | 60 |

TABLE 5-continued

Powder Catalyst Performance in Various Solvent Compositions

| Carbon Support | BET Surface Area ($m^2/g$) | Solvent | FDCA Yield (mol %) |
|---|---|---|---|
| Cabot Monarch 280 | 30 | 50 wt. % Dioxane/50 wt. % $H_2O$ | 73 |
| Continental N234 | 117 | 50 wt. % Dioxane/50 wt. % $H_2O$ | 71 |
| Continental N330 | 77 | 50 wt. % Dioxane/50 wt. % $H_2O$ | 74 |
| Orion Arosperse 5-183A | 42 | 50 wt. % Dioxane/50 wt. % $H_2O$ | 72 |
| Orion Lamp Black 101 | 20 | 50 wt. % Dioxane/50 wt. % $H_2O$ | 74 |
| Timcal Ensaco 250G | 56 | 50 wt. % Dioxane/50 wt. % $H_2O$ | 76 |
| Asbury 5358R | 67 | 82 wt. % Dioxane/18 wt. % $H_2O$ | 53 |
| Asbury 5375R | 30 | 82 wt. % Dioxane/18 wt. % $H_2O$ | 30 |
| Cabot Monarch 280 | 30 | 82 wt. % Dioxane/18 wt. % $H_2O$ | 54 |
| Continental N234 | 117 | 82 wt. % Dioxane/18 wt. % $H_2O$ | 48 |
| Continental N330 | 77 | 82 wt. % Dioxane/18 wt. % $H_2O$ | 52 |
| Orion Arosperse 5-183A | 42 | 82 wt. % Dioxane/18 wt. % $H_2O$ | 48 |
| Orion Lamp Black 101 | 20 | 82 wt. % Dioxane/18 wt. % $H_2O$ | 53 |
| Timcal Ensaco 250G | 56 | 82 wt. % Dioxane/18 wt. % $H_2O$ | 50 |
| Asbury 5358R | 67 | 23 wt. % Diglyme/77 wt. % $H_2O$ | 75 |
| Asbury 5375R | 30 | 23 wt. % Diglyme/77 wt. % $H_2O$ | 73 |
| Cabot Monarch 280 | 30 | 23 wt. % Diglyme/77 wt. % $H_2O$ | 77 |
| Continental N234 | 117 | 23 wt. % Diglyme/77 wt. % $H_2O$ | 75 |
| Continental N330 | 77 | 23 wt. % Diglyme/77 wt. % $H_2O$ | 77 |
| Orion Arosperse 5-183A | 42 | 23 wt. % Diglyme/77 wt. % $H_2O$ | 76 |
| Orion Lamp Black 101 | 20 | 23 wt. % Diglyme/77 wt. % $H_2O$ | 79 |
| Timcal Ensaco 250G | 56 | 23 wt. % Diglyme/77 wt. % $H_2O$ | 76 |
| Asbury 5358R | 67 | 50 wt. % Diglyme/50 wt. % $H_2O$ | 75 |
| Asbury 5375R | 30 | 50 wt. % Diglyme/50 wt. % $H_2O$ | 68 |
| Cabot Monarch 280 | 30 | 50 wt. % Diglyme/50 wt. % $H_2O$ | 73 |
| Continental N234 | 117 | 50 wt. % Diglyme/50 wt. % $H_2O$ | 74 |
| Continental N330 | 77 | 50 wt. % Diglyme/50 wt. % $H_2O$ | 74 |
| Orion Arosperse 5-183A | 42 | 50 wt. % Diglyme/50 wt. % $H_2O$ | 73 |
| Orion Lamp Black 101 | 20 | 50 wt. % Diglyme/50 wt. % $H_2O$ | 74 |
| Timcal Ensaco 250G | 56 | 50 wt. % Diglyme/50 wt. % $H_2O$ | 73 |

Example 18

Preparation and Testing of Carbon-Based Extrudate Catalysts in a Variety of Solvent Mixtures An aqueous solution (0.25 ml) containing 60 mg/ml Pt in the form of platinum nitrate was added to carbon extrudates (average 3 mm length and 0.75 mm diameter, 500 mg, prepared as described in WO 2015/168327, which is incorporated herein by reference), and the resultant material was agitated to impregnate the supports. The samples were then dried in an oven at 100° C. for 3 hours, and reduced at 350° C. under a forming gas (5% $H_2$ and 95% $N_2$) atmosphere for 3 hours with 5° C./min temperature ramp rate to produce catalyst with a composition of 3.0 wt. % Pt. By using other carbon-based extrudate supports, Pt precursors, and adjusting the amount of Pt in solution, different catalysts with various Pt loadings on a variety of carbon-based extrudate supports were prepared in a similar manner.

Above catalysts were tested for 5-(Hydroxymethyl)furfural (HMF) oxidation with a very similar testing protocol by using 15 mg 3.0 wt. % Pt on extrudates of average 3 mm length and 0.75 mm diameter in an HMF solution (250 μl of 6.0 wt. % or 0.50 M in a variety of solvent mixtures of water with DME, 1,4-dioxane, diglyme, triglyme, tetraglyme and higlyme). The glass vial insert was loaded into a reactor and the reactor was closed. The atmosphere in the reactor was replaced with oxygen and pressurized to 200 psig at ambient temperature. The reactor was heated to 120° C. and maintained at the respective temperature for 2 hours while the vial was shaken. After that, shaking was stopped and reactor was cooled to 40° C. Pressure in the reactor was then slowly released. The glass vial insert was removed from the reactor and centrifuged. The solution was diluted with dimethyl sulfoxide (DMSO) followed by 1,4-dioxane:water (2:1 v/v) and analyzed by HPLC with a UV detector to determine the yield of 2,5-furandicarboxylic acid (FDCA). The results are presented in Table 6.

TABLE 6

Extrudate Catalyst (average 3 mm length and 0.75 mm diameter) Performance in Various Solvent Mixtures.

| Carbon Support | BET Surface Area ($m^2/g$) | Solvent | FDCA Yield (mol %) |
|---|---|---|---|
| Timcal Ensaco 250G | 123 | 50 wt. % Dioxane/50 wt. % $H_2O$ | 65 |
| Orion Arosperse 5-183A | 91 | 50 wt. % Dioxane/50 wt. % $H_2O$ | 59 |
| Continental N120 | 98 | 50 wt. % Dioxane/50 wt. % $H_2O$ | 52 |
| Continental N234 | 137 | 50 wt. % Dioxane/50 wt. % $H_2O$ | 39 |
| Continental N330 | 115 | 50 wt. % Dioxane/50 wt. % $H_2O$ | 59 |
| Continental N550 | 88 | 50 wt. % Dioxane/50 wt. % $H_2O$ | 56 |
| Timcal Ensaco 250G | 123 | 50 wt. % Diglyme/50 wt. % $H_2O$ | 62 |
| Orion Arosperse 5-183A | 91 | 50 wt. % Diglyme/50 wt. % $H_2O$ | 24 |
| Continental N234 | 137 | 50 wt. % Diglyme/50 wt. % $H_2O$ | 24 |
| Continental N330 | 115 | 50 wt. % Diglyme/50 wt. % $H_2O$ | 43 |
| Timcal Ensaco 250G | 123 | 50 wt. % Triglyme/50 wt. % $H_2O$ | 38 |
| Timcal Ensaco 250G | 123 | 50 wt. % Tetraglyme/50 wt. % $H_2O$ | 18 |
| Timcal Ensaco 250G | 123 | 50 wt. % Higlyme/50 wt. % $H_2O$ | 16 |

Example 19

Testing of Carbon-Supported Powder Catalysts in a Variety of Solvent Mixtures 5, 10, 15, or 20 mg 3.0 wt. % Pt on Continental N234 carbon black powder (prepared from platinum nitrate) was tested for 5-(Hydroxymethyl)furfural (HMF) oxidation using a very similar testing protocol to Example 5 in an HMF solution (250 al of 6.0 wt. % or 0.50 M in a variety of solvent mixtures of water and 1,4-dioxane with different ratios). The glass vial insert was loaded into a reactor and the reactor was closed. The atmosphere in the reactor was replaced with oxygen and pressurized to 200 psig at ambient temperature. The reactor was heated to 110° C. and maintained at the respective temperature for 3 hours while the vial was shaken. After that, shaking was stopped and the reactor was cooled to 40° C. Pressure in the reactor was then slowly released. The glass vial insert was removed from the reactor and centrifuged. The solution was diluted with dimethyl sulfoxide (DMSO) followed by 1,4-dioxane:water (2:1 v/v) and analyzed by HPLC with a UV detector to determine the yield of 2,5-furandicarboxylic acid (FDCA). Results are presented in Table 7.

TABLE 7

Powder Catalyst Performance in Various Dioxane/$H_2O$ Solvent Mixtures.

| Catalyst (mg) | Solvent | FDCA Yield (%) |
|---|---|---|
| 5 | 100 wt. % Dioxane | 0 |
| 10 | 100 wt. % Dioxane | 3 |

TABLE 7-continued

Powder Catalyst Performance in Various Dioxane/H₂O Solvent Mixtures.

| Catalyst (mg) | Solvent | FDCA Yield (%) |
|---|---|---|
| 15 | 100 wt. % Dioxane | 7 |
| 20 | 100 wt. % Dioxane | 11 |
| 5 | 90 wt. % Dioxane/10 wt. % H₂O | 14 |
| 10 | 90 wt. % Dioxane/10 wt. % H₂O | 38 |
| 15 | 90 wt. % Dioxane/10 wt. % H₂O | 54 |
| 20 | 90 wt. % Dioxane/10 wt. % H₂O | 64 |
| 5 | 80 wt. % Dioxane/20 wt. % H₂O | 24 |
| 10 | 80 wt. % Dioxane/20 wt. % H₂O | 56 |
| 15 | 80 wt. % Dioxane/20 wt. % H₂O | 72 |
| 20 | 80 wt. % Dioxane/20 wt. % H₂O | 81 |
| 5 | 70 wt. % Dioxane/30 wt. % H₂O | 34 |
| 10 | 70 wt. % Dioxane/30 wt. % H₂O | 65 |
| 15 | 70 wt. % Dioxane/30 wt. % H₂O | 79 |
| 20 | 70 wt. % Dioxane/30 wt. % H₂O | 84 |
| 5 | 60 wt. % Dioxane/40 wt. % H₂O | 37 |
| 10 | 60 wt. % Dioxane/40 wt. % H₂O | 74 |
| 15 | 60 wt. % Dioxane/40 wt. % H₂O | 84 |
| 20 | 60 wt. % Dioxane/40 wt. % H₂O | 88 |
| 5 | 50 wt. % Dioxane/50 wt. % H₂O | 43 |
| 10 | 50 wt. % Dioxane/50 wt. % H₂O | 76 |
| 15 | 50 wt. % Dioxane/50 wt. % H₂O | 87 |
| 20 | 50 wt. % Dioxane/50 wt. % H₂O | 89 |
| 5 | 40 wt. % Dioxane/60 wt. % H₂O | 46 |
| 10 | 40 wt. % Dioxane/60 wt. % H₂O | 79 |
| 15 | 40 wt. % Dioxane/60 wt. % H₂O | 89 |
| 20 | 40 wt. % Dioxane/60 wt. % H₂O | 91 |
| 5 | 20 wt. % Dioxane/80 wt. % H₂O | 55 |
| 10 | 20 wt. % Dioxane/80 wt. % H₂O | 84 |
| 15 | 20 wt. % Dioxane/80 wt. % H₂O | 87 |
| 20 | 20 wt. % Dioxane/80 wt. % H₂O | 86 |
| 5 | 100 wt. % H₂O | 68 |
| 10 | 100 wt. % H₂O | 82 |
| 15 | 100 wt. % H₂O | 82 |
| 20 | 100 wt. % H₂O | 79 |

Example 20

Testing of Carbon-Supported Extrudate Catalysts 10 or 20 mg 2.0 wt. % Pt on Continental N234 carbon black extrudates (average length 3 mm and diameter 1.5 mm or 0.75 mm prepared from PtO(NO₃)) was tested for 5-(Hydroxymethyl)furfural (HMF) oxidation using a very similar testing protocol in an HMF solution (250 μl of 6.0 wt. % or 0.50 M in a 50 wt. % Dioxane/50 wt. % H₂O). The glass vial insert was loaded into a reactor and the reactor was closed. The atmosphere in the reactor was replaced with oxygen and pressurized to 100, 200, or 400 psig at ambient temperature. The reactor was heated to 120° C. and maintained at the respective temperature for 2 hours while the vial was shaken. After that, shaking was stopped and reactor was cooled to 40° C. Pressure in the reactor was then slowly released. The glass vial insert was removed from the reactor and centrifuged. The solution was diluted with dimethyl sulfoxide (DMSO) followed by 1,4-dioxane:water (2:1 v/v) and analyzed by HPLC with a UV detector to determine the yield of 2,5-furandicarboxylic acid (FDCA). The results are presented in Table 8.

TABLE 8

Extrudate Catalyst Performance in 50 wt. % Dioxane/50 wt. % H₂O Solvent Mixtures.

| Extrudate Diameter (mm) | O₂ Pressure (psig) | Catalyst (mg) | FDCA Yield (mol %) |
|---|---|---|---|
| 0.75 | 100 | 10 | 35 |
| 0.75 | 100 | 20 | 67 |
| 1.5 | 100 | 10 | 25 |
| 1.5 | 100 | 20 | 48 |
| 0.75 | 200 | 20 | 76 |
| 1.5 | 200 | 20 | 77 |
| 0.75 | 400 | 10 | 55 |
| 0.75 | 400 | 20 | 76 |
| 1.5 | 400 | 10 | 49 |
| 1.5 | 400 | 20 | 77 |

Example 21

Testing of Carbon-Supported Extrudate Catalysts 20 mg 2.0 wt. % or 3.0 wt. % Pt on carbon black extrudates (average length 3 mm and diameter 1.5 mm or 0.75 mm prepared from PtO(NO₃)) was tested for 5-(Hydroxymethyl)-furfural (HMF) oxidation using very similar testing protocol in an HMF solution (250 μl of 6.0 wt. % or 0.50 M in a 50 wt. % Dioxane/50 wt. % H₂O). The glass vial insert was loaded into a reactor and the reactor was closed. The atmosphere in the reactor was replaced with oxygen and pressurized to 200 psig at ambient temperature. The reactor was heated to 120° C. and maintained at the respective temperature for 2 hours while the vial was shaken. After that, shaking was stopped and the reactor was cooled to 40° C. The pressure in the reactor was then slowly released. The glass vial insert was removed from the reactor and centrifuged. The solution was diluted with dimethyl sulfoxide (DMSO) followed by 1,4-dioxane:water (2:1 v/v) and analyzed by HPLC with a UV detector to determine the yield of 2,5-furandicarboxylic acid (FDCA). The results are presented in Table 9.

TABLE 9

Extrudate Catalyst Performance in 50 wt. % Dioxane/50 wt. % H₂O Solvent Mixtures.

| Support | Carbon Black Surface Area (m²/g) | Extrudate Surface Area (m²/g) | Extrudate Diameter (mm) | Extrudate Mercury Porosimetry Pore Area (m²/g) | Pt Loading (wt. %) | FDCA Yield (mol %) |
|---|---|---|---|---|---|---|
| Orion Lamp Black 101 | 20 | 87 | 0.75 | 10 | 2.0 | 30 |
| Asbury 5365R | 34 | 92 | 0.75 | 18 | 2.0 | 12 |
| Continental N550 | 38 | 88 | 0.75 | 21 | 2.0 | 67 |
| Continental N120 | 39 | 98 | 0.75 | 19 | 2.0 | 68 |
| Orion Arosperse 5-183A | 42 | 91 | 0.75 | 20 | 2.0 | 69 |
| Continental N330 | 77 | 115 | 0.75 | 38 | 2.0 | 76 |
| Continental N234 | 117 | 137 | 0.75 | 54 | 2.0 | 75 |
| Cabot Monarch 700 | 181 | 177 | 0.75 | 53 | 2.0 | 75 |
| Norit ROX 0.8 (Activated Carbon) | 1323 | 1323 | 0.75 | 24 | 2.0 | 42 |
| Orion Lamp Black 101 | 20 | 87 | 0.75 | 10 | 3.0 | 37 |
| Asbury 5365R | 34 | 92 | 0.75 | 18 | 3.0 | 45 |
| Continental N550 | 38 | 88 | 0.75 | 21 | 3.0 | 61 |
| Continental N120 | 39 | 98 | 0.75 | 19 | 3.0 | 59 |

TABLE 9-continued

Extrudate Catalyst Performance in 50 wt. % Dioxane/50 wt. % $H_2O$ Solvent Mixtures.

| Support | Carbon Black Surface Area ($m^2/g$) | Extrudate Surface Area ($m^2/g$) | Extrudate Diameter (mm) | Extrudate Mercury Porosimetry Pore Area ($m^2/g$) | Pt Loading (wt. %) | FDCA Yield (mol %) |
|---|---|---|---|---|---|---|
| Orion Arosperse 5-183A | 42 | 91 | 0.75 | 20 | 3.0 | 66 |
| Continental N330 | 77 | 115 | 0.75 | 38 | 3.0 | 76 |
| Continental N234 | 117 | 137 | 0.75 | 54 | 3.0 | 79 |
| Cabot Monarch 700 | 181 | 177 | 0.75 | 53 | 3.0 | 77 |
| Norit ROX 0.8 (Activated Carbon) | 1323 | 1323 | 0.75 | 24 | 3.0 | 41 |

Example 22

Testing of Carbon-Supported Powder and Extrudate Catalysts in N-Methyl-2-Pyrrolidone/$H_2O$ Solvent Compositions 10 or 20 mg 3.0 wt. % Pt on Continental N234 carbon black powder (prepared from platinum nitrate) or extrudates (average length 3 mm and diameter 1.5 mm or 0.75 mm prepared from $PtO(NO_3)$) was tested for 5-(Hydroxymethyl) furfural (HMF) oxidation using very similar testing protocol in an HMF solution (250 μl of 6.0 wt. % or 0.50 M in a solvent mixture of N-Methyl-2-Pyrrolidone (NMP) and $H_2O$). The glass vial insert was loaded into a reactor and the reactor was closed. The atmosphere in the reactor was replaced with oxygen and pressurized to 200 psig at ambient temperature. The reactor was heated to 110° C. and maintained at the respective temperature for 3 hours while the vial was shaken. After that, shaking was stopped and the reactor was cooled to 40° C. The pressure in the reactor was then slowly released. The glass vial insert was removed from the reactor and centrifuged. The solution was diluted with dimethyl sulfoxide (DMSO) followed by 1,4-dioxane:water (2:1 v/v) and analyzed by HPLC with a UV detector to determine the yield of 2,5-furandicarboxylic acid (FDCA). The results are presented in Table 10.

TABLE 10

Powder and Extrudate Catalyst Performance in NMP/$H_2O$ Solvent Mixtures.

| Solvent Composition | Catalyst Size | Catalyst Amount (mg) | FDCA Yield (mol %) |
|---|---|---|---|
| 100 wt. % NMP | Powder | 10 | 1 |
| 98 wt. % NMP/2 wt. % $H_2O$ | Powder | 10 | 1 |
| 95 wt. % NMP/5 wt. % $H_2O$ | Powder | 10 | 1 |
| 90 wt. % NMP/10 wt. % $H_2O$ | Powder | 10 | 4 |
| 85 wt. % NMP/15 wt. % $H_2O$ | Powder | 10 | 7 |
| 80 wt. % NMP/20 wt. % $H_2O$ | Powder | 10 | 15 |
| 70 wt. % NMP/30 wt. % $H_2O$ | Powder | 10 | 23 |
| 60 wt. % NMP/40 wt. % $H_2O$ | Powder | 10 | 32 |
| 50 wt. % NMP/50 wt. % $H_2O$ | Powder | 10 | 42 |
| 40 wt. % NMP/60 wt. % $H_2O$ | Powder | 10 | 44 |
| 20 wt. % NMP/80 wt. % $H_2O$ | Powder | 10 | 44 |
| 100 wt. % $H_2O$ | Powder | 10 | 80 |
| 100 wt. % NMP | Powder | 20 | 1 |
| 98 wt. % NMP/2 wt. % $H_2O$ | Powder | 20 | 2 |
| 95 wt. % NMP/5 wt. % $H_2O$ | Powder | 20 | 4 |
| 90 wt. % NMP/10 wt. % $H_2O$ | Powder | 20 | 13 |
| 85 wt. % NMP/15 wt. % $H_2O$ | Powder | 20 | 22 |
| 80 wt. % NMP/20 wt. % $H_2O$ | Powder | 20 | 32 |
| 70 wt. % NMP/30 wt. % $H_2O$ | Powder | 20 | 51 |
| 60 wt. % NMP/40 wt. % $H_2O$ | Powder | 20 | 57 |
| 50 wt. % NMP/50 wt. % $H_2O$ | Powder | 20 | 66 |
| 40 wt. % NMP/60 wt. % $H_2O$ | Powder | 20 | 66 |
| 20 wt. % NMP/80 wt. % $H_2O$ | Powder | 20 | 71 |
| 100 wt. % $H_2O$ | Powder | 20 | 78 |
| 100 wt. % NMP | 0.75 mm × 3 mm | 20 | 10 |
| 98 wt. % NMP/2 wt. % $H_2O$ | 0.75 mm × 3 mm | 20 | 11 |
| 95 wt. % NMP/5 wt. % $H_2O$ | 0.75 mm × 3 mm | 20 | 11 |
| 90 wt. % NMP/10 wt. % $H_2O$ | 0.75 mm × 3 mm | 20 | 12 |
| 85 wt. % NMP/15 wt. % $H_2O$ | 0.75 mm × 3 mm | 20 | 14 |
| 80 wt. % NMP/20 wt. % $H_2O$ | 0.75 mm × 3 mm | 20 | 16 |
| 70 wt. % NMP/30 wt. % $H_2O$ | 0.75 mm × 3 mm | 20 | 22 |
| 60 wt. % NMP/40 wt. % $H_2O$ | 0.75 mm × 3 mm | 20 | 32 |
| 50 wt. % NMP/50 wt. % $H_2O$ | 0.75 mm × 3 mm | 20 | 36 |
| 40 wt. % NMP/60 wt. % $H_2O$ | 0.75 mm × 3 mm | 20 | 46 |
| 20 wt. % NMP/80 wt. % $H_2O$ | 0.75 mm × 3 mm | 20 | 51 |
| 100 wt. % $H_2O$ | 0.75 mm × 3 mm | 20 | 79 |

Example 23

FDCA Solubility Studies in Various Solvent Compositions

A series of samples containing various amounts of FDCA and mixed solvent compositions were prepared in sealed pressure ampules (typically containing 2-5 g material (FDCA and solvent composition)). For example, 200 mg FDCA, 900 mg NMP, and 900 mg de-ionized water were added to an 8 mL glass vial with a stir bar inside, corresponding to a mixture containing 10 wt % FDCA. Other samples corresponding to different wt % FDCA samples in various mixed solvent compositions were prepared in a similar manner. These vials were sealed and heated at a desired temperature for ca. 60 minutes with stirring, and samples were then visually inspected to determine if FDCA had totally dissolved (a clear solution represented dissolution of the FDCA, while a cloudy solution suggested incomplete dissolution). The reported FDCA solubility in Table 11 represents the maximum wt % FDCA that can be dissolved in the given solvent composition using this testing method.

TABLE 11

FDCA Solubilities in Various Solvent Compositions.

| Organic solvent | Solvent (wt. %) | $H_2O$ (wt. %) | Temperature (° C.) | FDCA solubility (wt. %) |
|---|---|---|---|---|
| NMP | 50 | 50 | 23 | 2.5 |
| NMP | 50 | 50 | 100 | 14.5 |
| NMP | 50 | 50 | 120 | 19.5 |
| NMP | 35 | 65 | 23 | 0.5 |
| NMP | 35 | 65 | 100 | 9.0 |
| NMP | 35 | 65 | 120 | 13.5 |
| NMP | 20 | 80 | 23 | 0.3 |
| NMP | 20 | 80 | 100 | 4.0 |
| NMP | 20 | 80 | 120 | 7.5 |
| ButOH | 50 | 50 | 100 | 7.0 |
| ButOH | 75 | 25 | 100 | 7.5 |
| MEK | 25 | 75 | 100 | 5.5 |

TABLE 11-continued

FDCA Solubilities in Various Solvent Compositions.

| Organic solvent | Solvent (wt. %) | $H_2O$ (wt. %) | Temperature (° C.) | FDCA solubility (wt. %) |
|---|---|---|---|---|
| MEK | 90 | 10 | 100 | 4.0 |
| gamma-valerolactone | 25 | 75 | 100 | 4.0 |
| gamma-valerolactone | 50 | 50 | 100 | 7.0 |
| gamma-valerolactone | 75 | 25 | 100 | 6.5 |

Example 24

Figure 12:
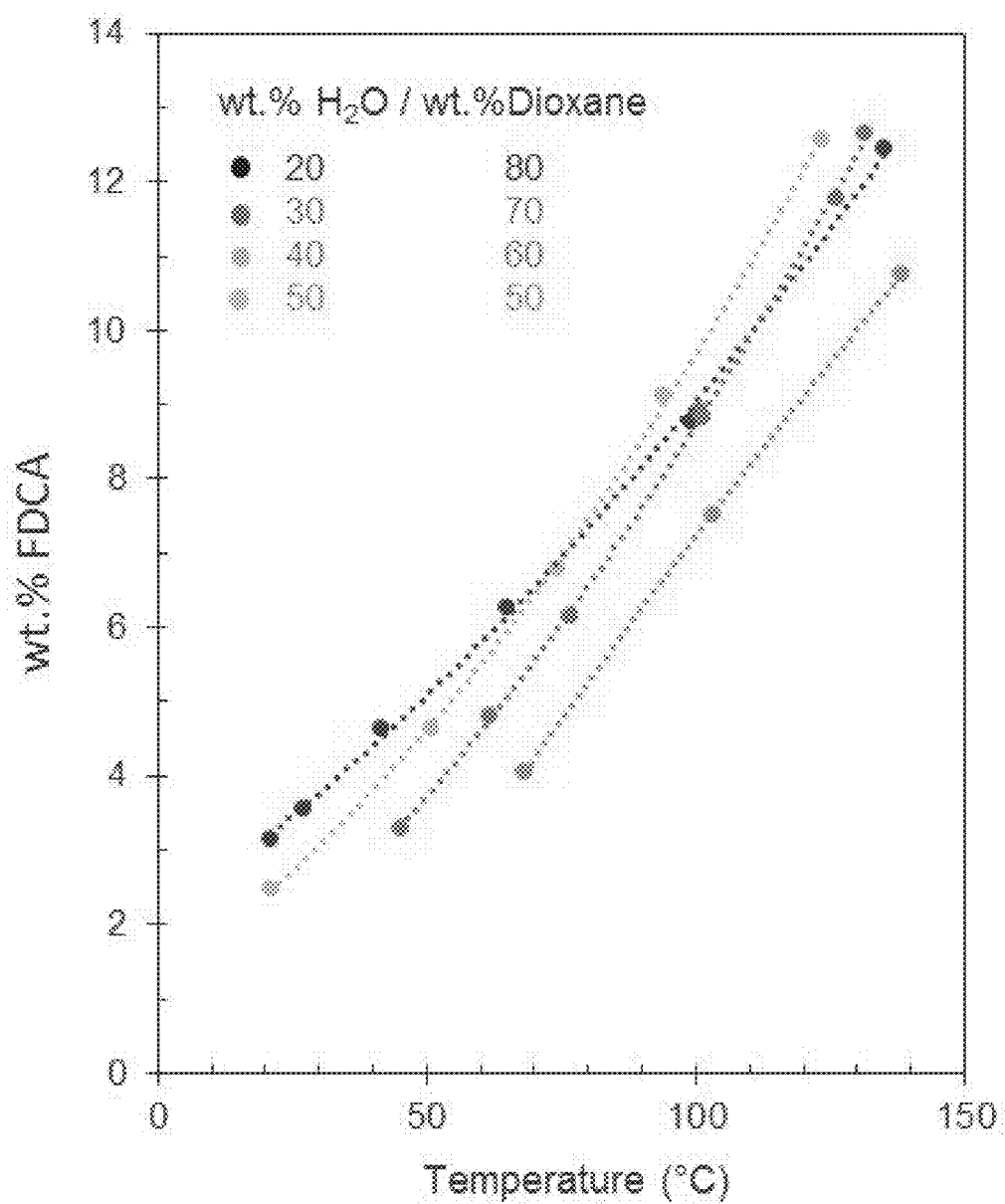
FIG. 12 depicts the temperature dependence of FDCA solubility in Dioxane/H$_2$O solvent compositions.
Figure 13:
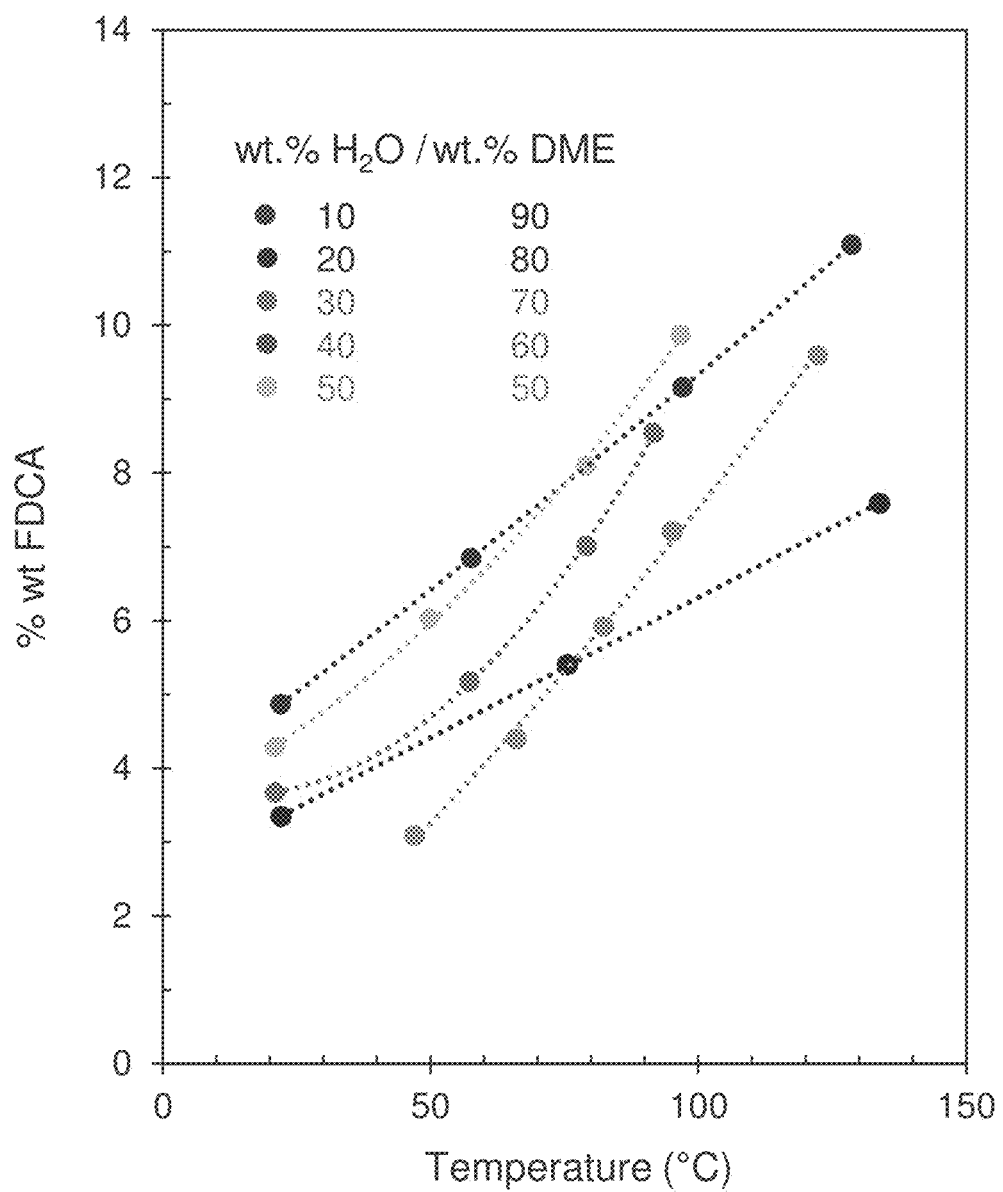
FIG. 13 depicts the temperature dependence of FDCA solubility in DME/H$_2$O solvent compositions.

FDCA Solubility in Various Dioxane/$H_2O$ and DME/$H_2O$ Solvent Compositions at Different Temperatures A protocol similar to that described in Example 23 was used to generate solubility data for FDCA in various Dioxane/$H_2O$ and DME/$H_2O$ solvent compositions. The results for Dioxane/$H_2O$ solvent compositions are shown in FIG. 12. The results for DME/$H_2O$ solvent compositions are shown in FIG. 13.

Example 25

Conversion of Fructose to HMF Using HBr in NMP

Analytical Conditions

Fructose remaining was quantified by HPLC using a Rezex RCU-USP column ($Ca^{+2}$ form, 4×250 mm, 8 m) and a refractive index detector (RID). Fructose was eluted isocratically with a mobile phase of $H_2O$.

Isomeric forms of difructose anhydrides, collectively referred to as intermediates, were quantified by HPLC using a Thermo Scientific Hypercarb column (3×50 mm, 3 μm) and a Charged Aerosol Detector (CAD). Intermediates were eluted by employing a mobile phase gradient of up to 15% $CH_3CN$ in $H_2O$ containing 0.1% TFA. 5-Hydroxymethylfurfural (HMF) was quantified by HPLC with UV detection at 254 nm using a Thermo Scientific Hypercarb column (3×50 mm, 3 μm). HMF was eluted by employing a mobile phase gradient of up to 15% $CH_3CN$ in $H_2O$ containing 0.1% TFA.

Fructose and HMF were quantified by fitting to calibration curves generated from pure standards. Intermediates were quantified by fitting to a calibration curve generated from di-D-fructofuranose-1,2':2,3'-dianhydride (DFA-III). DFA-III was purchased from Wako Chemicals.

Screening Conditions

General Procedure A. For Reactions Carried Out Using Microwave Heating.

Reaction stock solutions were prepared by first dissolving fructose in N-methyl-2-pyrrolidone (NMP) and $H_2O$. Acid catalyst was added last using either concentrated aqueous HBr (48 wt %) or concentrated $H_2SO_4$ (97 wt %). The final composition of each stock solution contained 0.6M fructose, 0.1M acid, and 2.0M $H_2O$.

Reactions were carried out using a Biotage Initiator Microwave reactor. The wattage output of the reactor was varied by the instrument in order to maintain a target temperature. Microwave vials, equipped with a magnetic stir bar, were charged with 3 g of stock solution and sealed.

General Procedure B. For Reactions Carried Out Using Conventional Heating.

Reaction stock solutions were prepared by first dissolving fructose in N-methyl-2-pyrrolidone (NMP) and $H_2O$. Acid catalyst was added last using either concentrated aqueous HBr (48 wt %) or concentrated HCl (37 wt %). Each stock solution prepared contained 0.6M fructose. Acid and $H_2O$ concentration was varied for these experiments. The concentrations tested are listed below in Tables 13 and 14.

Reactions were carried out in 8 mL glass vials using conventional heating with magnetic stirring. Reaction vials, equipped with a magnetic stir bar, were charged with 3 g of stock solution and sealed. Vials were placed in a pre-heated aluminum block set to the desired temperature.

Figure 14:
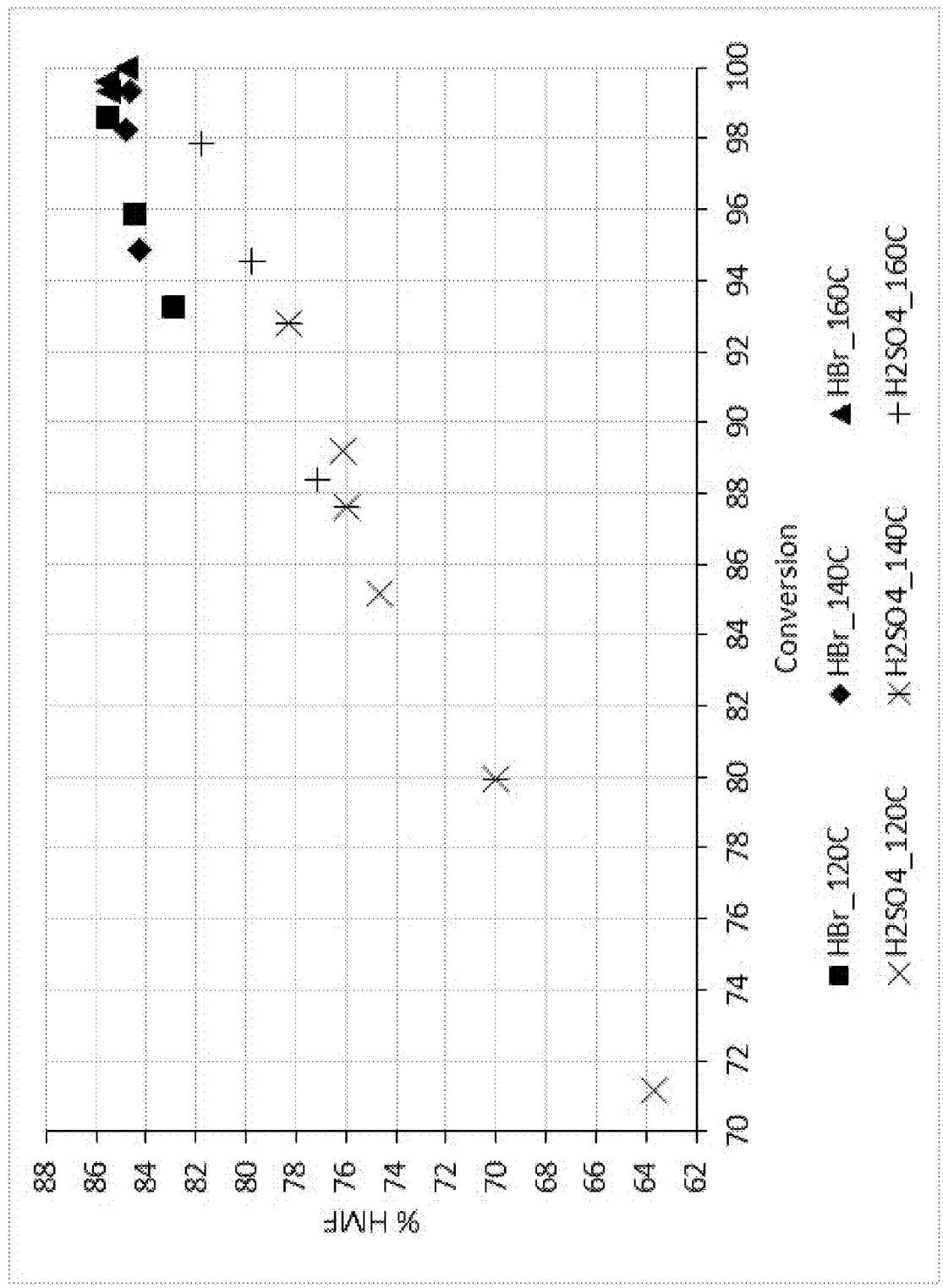
FIG. 14 depicts a plot of percent HMF yield versus percent conversion for the conversion of fructose to HMF using HBr and H$_2$SO$_4$ in NMP and H$_2$O.

Example 25.1: Comparison of HBr and $H_2SO_4$ as Catalyst Using General Procedure A Conditions tested along with results are listed in Table 12 and depicted graphically in FIG. 14. These results show that a higher yield of HMF can be achieved using HBr as catalyst compared to $H_2SO_4$. The yield of HMF was not sensitive to a change in reaction temperature within the range of 120-160° C.

TABLE 12

Conditions tested and results using General Procedure A.

| Entry | Catalyst | Temperature (° C.) | Heating Time (min)[1] | % Conversion[2] | % HMF | Selectivity[3] |
|---|---|---|---|---|---|---|
| 1 | HBr | 120 | 5 | 93.3 | 81.9 | 87.8 |
| 2 | HBr | 120 | 10 | 95.9 | 83.8 | 87.4 |
| 3 | HBr | 120 | 20 | 98.6 | 83.6 | 84.8 |
| 4 | HBr | 140 | 1 | 94.9 | 82.9 | 87.3 |
| 5 | HBr | 140 | 2 | 98.3 | 83.9 | 85.3 |
| 6 | HBr | 140 | 4 | 99.3 | 84.3 | 84.9 |
| 7 | HBr | 160 | 0.5 | 99.3 | 84.1 | 84.6 |
| 8 | HBr | 160 | 1 | 99.6 | 84.8 | 85.1 |
| 9 | HBr | 160 | 2 | 100 | 83.9 | 83.9 |
| 10 | $H_2SO_4$ | 120 | 10 | 71.2 | 63.6 | 89.4 |
| 11 | $H_2SO_4$ | 120 | 30 | 85.2 | 74.7 | 87.7 |
| 12 | $H_2SO_4$ | 120 | 50 | 89.2 | 76.1 | 85.4 |
| 13 | $H_2SO_4$ | 140 | 2 | 79.9 | 70 | 87.6 |
| 14 | $H_2SO_4$ | 140 | 5 | 87.6 | 76 | 86.7 |
| 15 | $H_2SO_4$ | 140 | 10 | 92.8 | 78.3 | 84.4 |
| 16 | $H_2SO_4$ | 160 | 1 | 88.4 | 77.1 | 87.2 |
| 17 | $H_2SO_4$ | 160 | 2 | 94.5 | 79.7 | 84.4 |
| 18 | $H_2SO_4$ | 160 | 4 | 97.8 | 81.8 | 83.6 |

[1]Does not include ramp time to target temperature.
[2]% Conversion = 100 − (% Fructose + % Intermediates).
[3]Selectivity = (% HMF/% Conversion) * 100.

Figure 15:
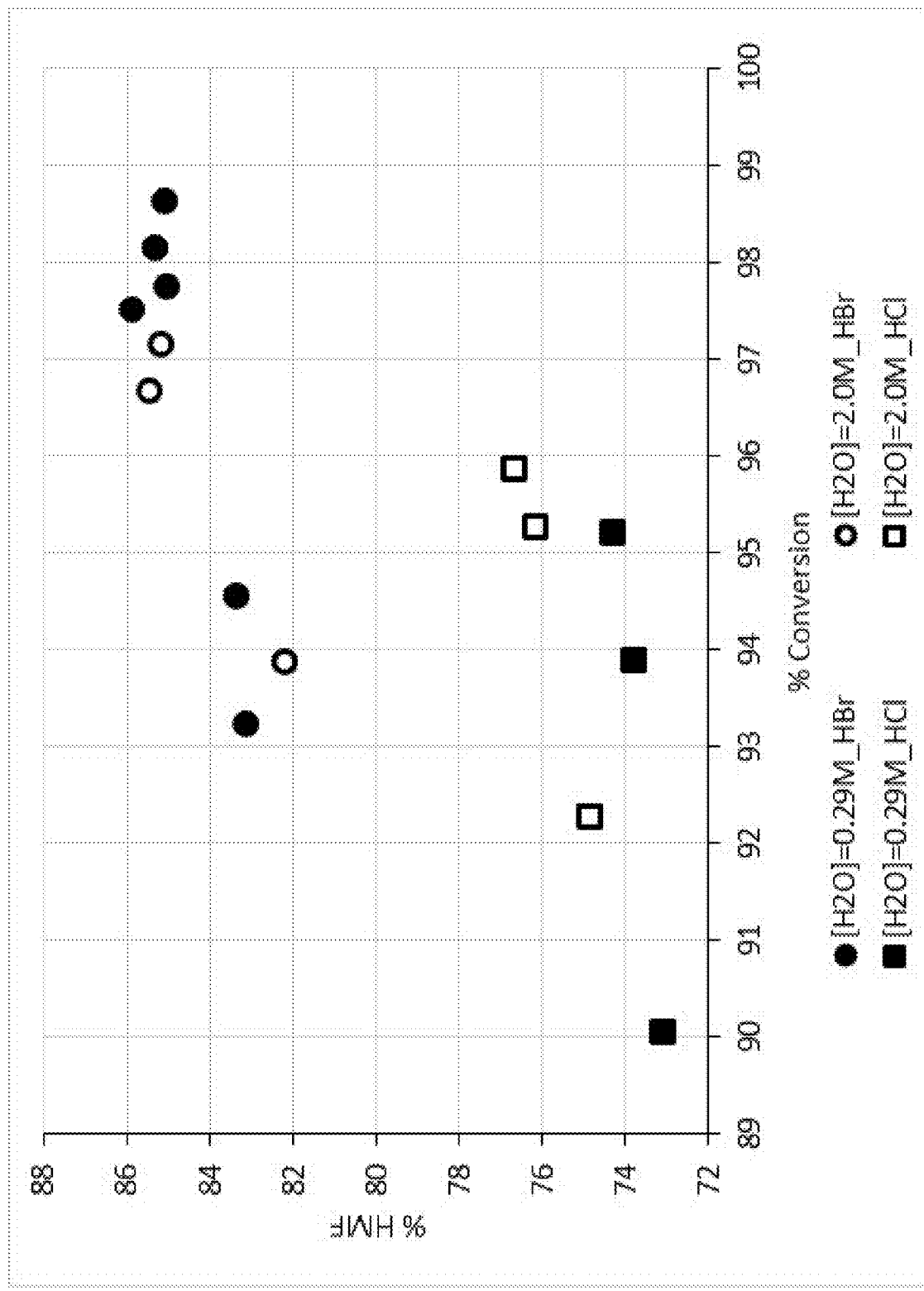
FIG. 15 depicts a plot of percent HMF yield versus percent conversion for the conversion of fructose to HMF using HBr and HCl in NMP and H$_2$O.

Example 25.2: Comparison of HBr and HCl as Catalyst at 120° C. Using General Procedure B Conditions tested along with results are listed in Table 13 and depicted graphically in FIG. 15. These results show that higher HMF yield can be achieved using HBr as catalyst compared to HCl.

TABLE 13

Results of conditions tested at 120° C. using General Procedure B.

| Entry | Catalyst | [Catalyst] (M) | H₂O (M) | Heating Time (min) | % Conversion[1] | % HMF | Selectivity[2] |
|---|---|---|---|---|---|---|---|
| 1 | HBr | 0.06 | 0.29 | 30 | 94.6 | 83.4 | 88.2 |
| 2 | HBr | 0.06 | 0.29 | 30 | 93.3 | 83.1 | 89.1 |
| 3 | HBr | 0.06 | 0.29 | 60 | 97.8 | 85.0 | 87.0 |
| 4 | HBr | 0.06 | 0.29 | 60 | 97.5 | 85.8 | 88.0 |
| 5 | HBr | 0.06 | 0.29 | 90 | 98.2 | 85.3 | 86.9 |
| 6 | HBr | 0.06 | 0.29 | 90 | 98.6 | 85.1 | 86.2 |
| 7 | HBr | 0.06 | 2 | 30 | 93.9 | 82.2 | 87.6 |
| 8 | HBr | 0.06 | 2 | 60 | 96.7 | 85.5 | 88.4 |
| 9 | HBr | 0.06 | 2 | 90 | 97.2 | 85.2 | 87.7 |
| 10 | HCl | 0.045 | 0.29 | 30 | 90.1 | 73.1 | 81.1 |
| 11 | HCl | 0.045 | 0.29 | 60 | 93.9 | 73.8 | 78.6 |
| 12 | HCl | 0.045 | 0.29 | 90 | 95.2 | 74.3 | 78.0 |
| 13 | HCl | 0.045 | 2 | 30 | 92.3 | 74.8 | 81.1 |
| 14 | HCl | 0.045 | 2 | 60 | 95.3 | 76.2 | 79.9 |
| 15 | HCl | 0.045 | 2 | 90 | 95.9 | 76.7 | 79.9 |

[1]% Conversion = 100 − (% Fructose + % Intermediates).
[2]Selectivity = (% HMF/% Conversion) * 100.

Figure 16:
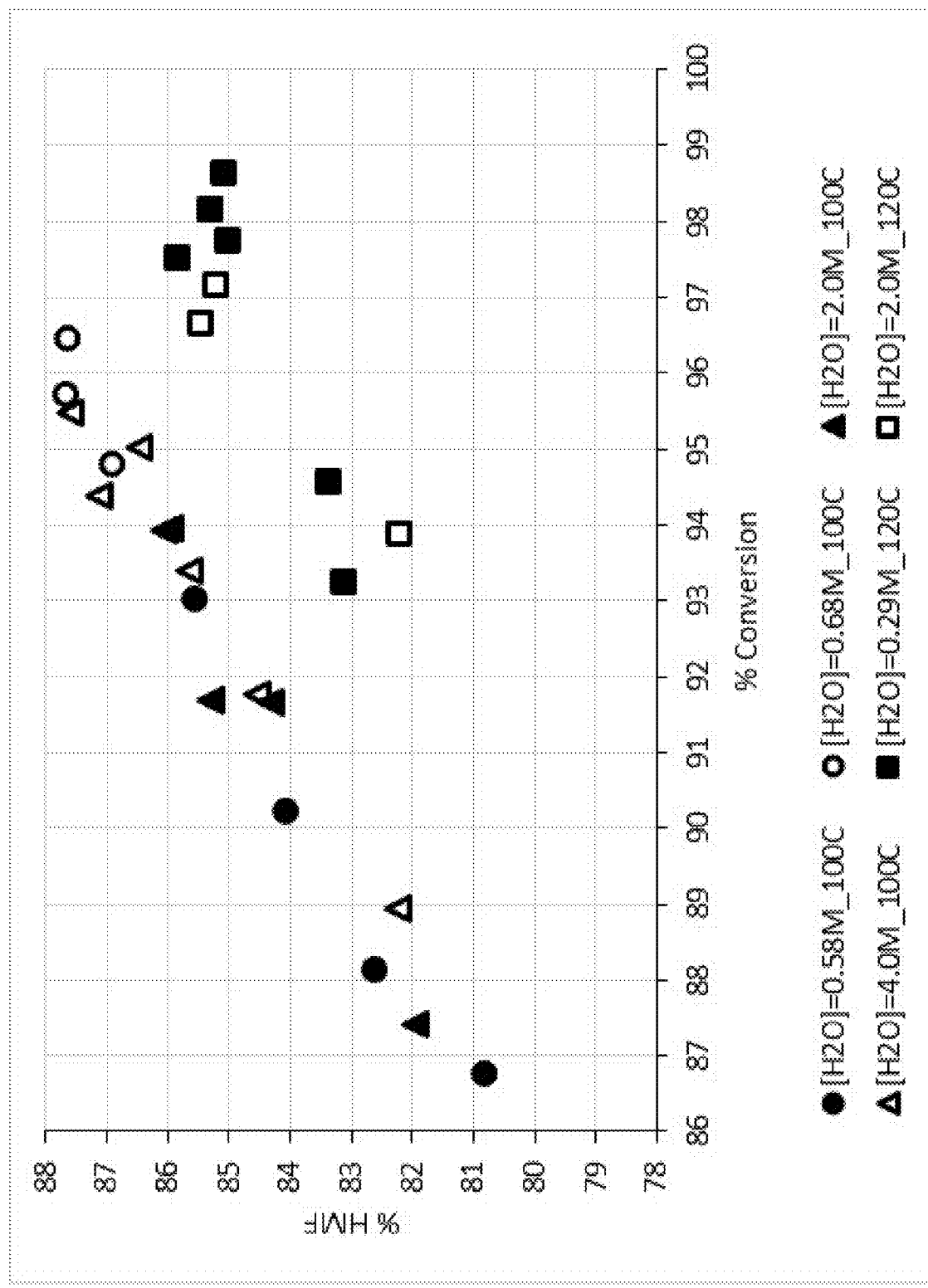
FIG. 16 depicts a plot of percent HMF yield versus percent conversion for the conversion of fructose to HMF using HBr in NMP and $H_2O$.

Example 25.3: Comparison of 100° C. and 120° C. Reaction Temperature Using General Procedure B Conditions tested along with results are listed in Table 14 and depicted graphically in FIG. 16. These results show an increase in HMF yield when the reaction temperature is reduced from 120° C. to 100° C.

TABLE 14

Results of conditions tested using General Procedure B.

| Entry | [HBr] (M) | H₂O (M) | Temperature (° C.) | Heating Time (min) | % Conversion[1] | % HMF | Selectivity[2] |
|---|---|---|---|---|---|---|---|
| 1 | 0.12 | 0.58 | 100 | 18 | 86.8 | 80.8 | 93.2 |
| 2 | 0.12 | 0.58 | 100 | 27 | 88.1 | 82.6 | 93.7 |
| 3 | 0.12 | 0.58 | 100 | 36 | 90.2 | 84.1 | 93.2 |
| 4 | 0.12 | 0.58 | 100 | 57 | 93.0 | 85.6 | 92.0 |
| 5 | 0.14 | 0.68 | 100 | 60 | 94.8 | 86.9 | 91.7 |
| 6 | 0.14 | 0.68 | 100 | 75 | 95.7 | 87.6 | 91.5 |
| 7 | 0.14 | 0.68 | 100 | 90 | 96.5 | 87.6 | 90.8 |
| 8 | 0.14 | 2 | 100 | 25 | 87.4 | 81.9 | 93.8 |
| 9 | 0.14 | 2 | 100 | 35 | 91.7 | 84.3 | 92.0 |
| 10 | 0.14 | 2 | 100 | 45 | 91.7 | 85.3 | 93.0 |
| 11 | 0.14 | 2 | 100 | 65 | 93.9 | 86.0 | 91.6 |
| 12 | 0.16 | 4 | 100 | 37 | 88.9 | 82.2 | 92.5 |
| 13 | 0.16 | 4 | 100 | 53 | 91.8 | 84.5 | 92.1 |
| 14 | 0.2 | 4 | 100 | 60 | 93.9 | 86.0 | 91.5 |
| 15 | 0.16 | 4 | 100 | 70 | 93.4 | 85.6 | 91.7 |
| 16 | 0.2 | 4 | 100 | 75 | 95.0 | 86.5 | 91.0 |
| 17 | 0.16 | 4 | 100 | 90 | 94.4 | 87.1 | 92.3 |
| 18 | 0.2 | 4 | 100 | 90 | 95.5 | 87.6 | 91.8 |
| 19 | 0.06 | 0.29 | 120 | 30 | 94.6 | 83.4 | 88.2 |
| 20 | 0.06 | 0.29 | 120 | 30 | 93.3 | 83.1 | 89.1 |
| 21 | 0.06 | 0.29 | 120 | 60 | 97.8 | 85.0 | 87.0 |
| 22 | 0.06 | 0.29 | 120 | 60 | 97.5 | 85.8 | 88.0 |
| 23 | 0.06 | 0.29 | 120 | 90 | 98.2 | 85.3 | 86.9 |
| 24 | 0.06 | 0.29 | 120 | 90 | 98.6 | 85.1 | 86.2 |
| 25 | 0.06 | 2 | 120 | 30 | 93.9 | 82.2 | 87.6 |
| 26 | 0.06 | 2 | 120 | 60 | 96.7 | 85.5 | 88.4 |
| 27 | 0.06 | 2 | 120 | 90 | 97.2 | 85.2 | 87.7 |

[1]% Conversion = 100 − (% Fructose + % Intermediates).
[2]Selectivity = (% HMF/% Conversion) * 100.

While preferred embodiments of the disclosure have been illustrated and described, it will be appreciated that various changes can be made therein without departing from the spirit and scope of the disclosure.

We claim:

1. A process for producing a first 2,5-furandicarboxylic acid (FDCA) pathway product from a first furanic oxidation substrate, the process comprising:
    (a) contacting a first oxidation feedstock comprising a first furanic oxidation substrate and a first oxidation solvent with oxygen in the presence of a first heterogeneous oxidation catalyst under conditions sufficient to form a reaction mixture for oxidizing the first furanic oxidation substrate to a first FDCA pathway product, and producing the first FDCA pathway product;
    wherein the first oxidation solvent is a multi-component solvent comprising water and a water-miscible aprotic organic solvent;
    wherein no base is added to the reaction mixture during (first) contacting step (a);
    wherein the first oxidation feedstock has a pH of less than about 6;
    wherein the first heterogeneous oxidation catalyst comprises a first solid support and a first noble metal, and
    wherein the first solid support comprises a specific surface area in the range of from or any number in between 20 m²/g to 100 m²/g.

2. The process of claim 1, wherein the first noble metal is selected from the group consisting of platinum, gold, and combinations thereof.

3. The process of claim 1, wherein the water-miscible aprotic organic solvent is selected from the group consisting of tetrahydrofuran, a glyme, dioxane, a dioxolane, dimethylformamide, dimethylsulfoxide, sulfolane, acetone, N-methyl-2-pyrrolidone ("NMP"), methyl ethyl ketone ("MEK"), and gamma-valerolactone;
    and, if the water-miscible aprotic organic solvent is a glyme, then the glyme is selected from the group consisting of a monoglyme (1,2-dimethoxyethane), ethyl glyme, diglyme (diethylene glycol dimethyl ether), ethyl diglyme, triglyme, butyl diglyme, tetraglyme, and a polyglyme.

4. The process of claim 3, wherein the water-miscible aprotic organic solvent is a glyme.

5. The process of claim 4, wherein the water-miscible aprotic organic solvent is 1,2-dimethoxyethane ("DME").

6. The process of claim 4, wherein the water-miscible aprotic organic solvent is diglyme.

7. The process of claim 3, wherein the water-miscible aprotic organic solvent is dioxane.

8. The process of claim 3, wherein the water-miscible aprotic organic solvent is NMP.

9. The process of claim 3, wherein the water-miscible aprotic organic solvent is MEK.

10. The process of claim 1, wherein the weight percent ratio of the water-miscible aprotic organic solvent:water is in the range of from or any number in between 70:30 to 20:80.

11. The process of claim 10, wherein the weight percent ratio of the water-miscible aprotic organic solvent:water is in the range of from or any number in between 60:40 to 40:60.

12. The process of claim 1, wherein the first oxidation feedstock comprises the first furanic oxidation substrate at a concentration of at least 5% by weight.

13. The process of claim 1, wherein the first heterogeneous oxidation catalyst comprises the first noble metal at a loading in the range of from or any number in between 0.3% to 5% by weight of the first heterogeneous oxidation catalyst.

14. The process of claim 1, wherein the first solid support comprises a material selected from the group consisting of a metal oxide, a carbonaceous material, a polymer, a metal silicate, a metal carbide, and any combination of two or more thereof.

15. The process of claim 1, wherein the first solid support comprises a plurality of pores.

16. The process of claim 15, wherein the first solid support comprises a pore volume wherein at least 50% of the pore volume is from pores having a pore diameter in the range of from or any number in between 5 nm to 100 nm.

17. The process of claim 1, wherein the first solid support comprises a specific surface area of about 25 $m^2/g$.

18. The process of claim 1, wherein the first solid support comprises a specific surface area of about 20 $m^2/g$.

19. The process of claim 1, wherein the first solid support comprises a specific surface area in the range of from or any number in between 20 $m^2/g$ to 30 $m^2/g$.

20. The process of claim 1, wherein oxygen is present at a molar ratio of oxygen:the first furanic oxidation substrate in the range of from or any number in between 2:1 to 10:1.

21. The process of claim 1, wherein (first) contacting step (a) is carried out at a temperature in the range of from or any number in between 50° C. to 200° C.

22. The process of claim 1, wherein the first FDCA pathway product is produced at a yield of at least 80%.

23. The process of claim 1, wherein the first FDCA pathway product is FDCA.

24. The process of claim 1, wherein the first oxidation feedstock has a pH of about 3-6.

25. The process of claim 1, further comprising a second oxidation step, wherein the second oxidation step comprises:
   (b) contacting a second oxidation feedstock comprising a second furanic oxidation substrate and a second oxidation solvent with oxygen in the presence of a second heterogeneous oxidation catalyst under conditions sufficient to form a second reaction mixture for oxidizing the second furanic oxidation substrate to produce a second FDCA pathway product, and producing the second FDCA pathway product;
   wherein the first FDCA pathway product is an FDCA pathway intermediate compound, either alone or together with FDCA;
   wherein the second furanic oxidation substrate is the first FDCA pathway product; and
   wherein the second heterogeneous oxidation catalyst comprises a second solid support and a second noble metal, that may be the same or different from the first noble metal.

26. The process of claim 25, wherein the second noble metal is selected from the group consisting of platinum, gold, and a combination thereof.

27. The process of claim 25, wherein the second solid support comprises a plurality of pores.

28. The process of claim 25, wherein the second solid support comprises a specific surface area in the range of from or any number in between 20 $m^2/g$ to 100 $m^2/g$.

29. The process of claim 25, wherein the second solid support comprises a specific surface area in the range of from or any number in between 20 $m^2/g$ to 30 $m^2/g$.

30. The process of claim 1, further comprising:
   (a°) prior to (first) contacting step (a), contacting a carbohydrate feedstock comprising a sugar and a dehydration solvent with a dehydration catalyst under conditions sufficient to form a dehydration reaction mixture for dehydrating the sugar to produce the first furanic oxidation substrate, wherein the first furanic oxidation substrate is present in a dehydration product solution that comprises the first furanic oxidation substrate and the dehydration solvent.

31. The process of claim 30, wherein the dehydration catalyst is an acid catalyst.

32. The process of claim 31, wherein the acid catalyst is an acid selected from the group consisting of HBr, $H_2SO_4$, $HNO_3$, HCl, HI, $H_3PO_4$, triflic acid, methansulfonic acid, benzenesulfonic acid, and p-toluene sulfonic acid.

33. The process of claim 32, wherein the acid catalyst is HCl.

34. The process of claim 30, wherein the dehydration solvent comprises 1,4-dioxane and water.

35. The process of claim 30, wherein the sugar is fructose and the first furanic oxidation substrate is HMF.

36. The process of claim 30, wherein the (prior) contacting step (a°) is carried out at a temperature between 150° C. to 180° C.

37. The process of claim 30, wherein the (prior) contacting step (a°) further comprises the addition of a base to the dehydration product solution.

* * * * *